(12) United States Patent
Morant

(10) Patent No.: US 8,629,325 B2
(45) Date of Patent: Jan. 14, 2014

(54) POLYPEPTIDES HAVING BETA-GLUCOSIDASE ACTIVITY AND POLYNUCLEOTIDES ENCODING SAME

(75) Inventor: Marc Morant, Copenhagen (DK)

(73) Assignees: Novozymes A/S, Bagsvaerd (DK); Novozymes, Inc., Davis, CA (US)

( * ) Notice: Subject to any disclaimer, the term of this patent is extended or adjusted under 35 U.S.C. 154(b) by 0 days.

(21) Appl. No.: 13/818,208

(22) PCT Filed: Aug. 30, 2011

(86) PCT No.: PCT/US2011/049767
§ 371 (c)(1),
(2), (4) Date: Mar. 25, 2013

(87) PCT Pub. No.: WO2012/030845
PCT Pub. Date: Mar. 8, 2012

(65) Prior Publication Data
US 2013/0183713 A1    Jul. 18, 2013

Related U.S. Application Data

(60) Provisional application No. 61/382,220, filed on Sep. 13, 2010.

(30) Foreign Application Priority Data

Aug. 30, 2010   (EP) .................................. 101745677

(51) Int. Cl.
*C12N 15/56*   (2006.01)
*C12N 15/82*   (2006.01)
*C12N 9/42*    (2006.01)
*C12P 21/02*   (2006.01)

(52) U.S. Cl.
USPC .......... 800/284; 800/298; 435/200; 435/71.1; 536/23.2; 424/93.2

(58) Field of Classification Search
None
See application file for complete search history.

(56) References Cited

U.S. PATENT DOCUMENTS

2006/0095279 A1   5/2006   Benco et al.
2008/0201805 A1*  8/2008   Krogh et al. ................ 800/298

FOREIGN PATENT DOCUMENTS

| | | | |
|---|---|---|---|
| EP | 1479765 | A2 | 11/2004 |
| WO | 9700962 | A1 | 1/1997 |
| WO | 9700964 | A1 | 1/1997 |
| WO | 9906574 | A1 | 2/1999 |
| WO | 2004018662 | A2 | 3/2004 |
| WO | 2004078919 | A2 | 9/2004 |
| WO | 2005074647 | A2 | 8/2005 |
| WO | 2006114095 | A1 | 11/2006 |
| WO | 2007109441 | A2 | 9/2007 |
| WO | 2008034648 | A1 | 3/2008 |
| WO | 2008037757 | A1 | 4/2008 |
| WO | 2009042871 | A1 | 4/2009 |
| WO | 2009085859 | A2 | 7/2009 |
| WO | 2009133034 | A1 | 11/2009 |
| WO | 2010022518 | A1 | 3/2010 |
| WO | 2010076387 | A1 | 7/2010 |
| WO | 2010088387 | A1 | 8/2010 |
| WO | 2010126772 | A1 | 11/2010 |
| WO | 2011041405 | A1 | 4/2011 |

OTHER PUBLICATIONS

Uniprot. 2007. Accession A1DMR8. p. 1.*
Pozzo et al. 2010. Structural and funcitonal analyses of beta-glucosidase 3B from Thermotoga neapolitana: A thermostable three-domain representative of Glycoside Hydrolase 3. J. Mol. Biol. 397:724-739.*
Guo et al. 2004. Protein tolerance to random amino acid change. PNAS. 101(25):9205-9210.*
Brux et al, 2006, J Mol Biol 359(1), 97-109.
Espagne et al, 2008—Uniprot Access No. B2ARI1.
Hamid et al, 2008, Biotechnol Lett 30(12), 2165-2172.
Harris et al, 2010, Biochem 49(15), 3305-3316.
Kanamasa et al, 2003, J Biosci Bioeng 95(6), 627-629.
Koseki et al, 2007, App Microbio and Biotech 77(6), 1279-1285.
Mahajan et al, 2010, Appl Microbiol Biotechnol 86 (6), 1903-1914.
Naika et al, 2007, J Agric Food Chem 55(18), 7566-7572.
Pauly et al, 1999, Glycobiol 9(1), 93-100.
Pel et al, 2007, Nature Biotech 25(2), 221-231.
Pel et al, 2008, NCBI Access No. XM_001396955.
Shallom et al, 2003, Curr Opinion Microbiol 6 (3), 219-228.
Skjoet et al, 2001, Mol Genet Geno 265(5), 913-921.
Takada et al, 1998—Uniprot Acces No. 059843.
Takada et al, 1998, Biosci Biotechnol Biochem 62(8), 1615-1618.
Takada et al, 2002, J Biosci Bioeng 94(5), 482-485.
Vuong et al, 2010, Biotech and Bioengi 107(2), 195-205.
Ito et al, 2007, J Mol Catalys 49(1-4), 92-97.

* cited by examiner

*Primary Examiner* — Anne Kubelik
*Assistant Examiner* — Jeffrey Bolland
(74) *Attorney, Agent, or Firm* — Robert L. Starnes

(57) ABSTRACT

The present invention relates to isolated polypeptides having beta-glucosidase activity, beta-xylosidase activity, or beta-glucosidase and beta-xylosidase activity and isolated polynucleotides encoding the polypeptides. The invention also relates to nucleic acid constructs, vectors, and host cells comprising the polynucleotides as well as methods of producing and using the polypeptides.

25 Claims, No Drawings

1

POLYPEPTIDES HAVING BETA-GLUCOSIDASE ACTIVITY AND POLYNUCLEOTIDES ENCODING SAME

CROSS-REFERENCE TO RELATED APPLICATIONS

This application is a 35 U.S.C. 371 national application of PCT/US2011/049767 filed on Aug. 30, 2011, which claims priority or the benefit under 35 U.S.C. 119 of U.S. Provisional. Application No. 61/382,220 filed on Sep. 13, 2010, and European Application No. 10174567.7 filed on Aug. 30, 2010, the contents of which are fully incorporated herein by reference.

STATEMENT AS TO RIGHTS TO INVENTIONS MADE UNDER FEDERALLY SPONSORED RESEARCH AND DEVELOPMENT

This invention was made with Government support under Cooperative Agreement DE-FC36-08G018080 awarded by the Department of Energy. The government has certain rights in this invention.

REFERENCE TO A SEQUENCE LISTING

This application contains a Sequence Listing in computer readable form, which is incorporated herein by reference.

BACKGROUND OF THE INVENTION

1. Field of the Invention

The present invention relates to polypeptides having beta-glucosidase activity, beta-xylosidase activity, or beta-glucosidase and beta-xylosidase activity and polynucleotides encoding the polypeptides. The invention also relates to nucleic acid constructs, vectors, and host cells comprising the polynucleotides as well as methods of producing and using the polypeptides.

2. Description of the Related Art

Cellulose is a polymer of the simple sugar glucose covalently linked by beta-1,4-bonds. Many microorganisms produce enzymes that hydrolyze beta-linked glucans. These enzymes include endoglucanases, cellobiohydrolases, and beta-glucosidases. Endoglucanases digest the cellulose polymer at random locations, opening it to attack by cellobiohydrolases. Cellobiohydrolases sequentially release molecules of cellobiose from the ends of the cellulose polymer. Cellobiose is a water-soluble beta-1,4-linked dimer of glucose. Beta-glucosidases hydrolyze cellobiose to glucose.

The conversion of lignocellulosic feedstocks into ethanol has the advantages of the ready availability of large amounts of feedstock, the desirability of avoiding burning or land filling the materials, and the cleanliness of the ethanol fuel. Wood, agricultural residues, herbaceous crops, and municipal solid wastes have been considered as feedstocks for ethanol production. These materials primarily consist of cellulose, hemicellulose, and lignin. Once the lignocellulose is converted to fermentable sugars, e.g., glucose, the fermentable sugars are easily fermented by yeast into ethanol.

There is a need in the art for polypeptides having beta-glucosidase activity, beta-xylosidase activity, or beta-glucosidase and beta-xylosidase activity with improved properties for use in the degradation of cellulosic and xylan-containing materials.

The present invention provides new polypeptides having beta-glucosidase activity, beta-xylosidase activity, or beta-glucosidase and beta-xylosidase activity and polynucleotides encoding the polypeptides.

SUMMARY OF THE INVENTION

The present invention relates to isolated polypeptides having beta-glucosidase activity, beta-xylosidase activity, or beta-glucosidase and beta-xylosidase activity selected from the group consisting of:

(a) a polypeptide having at least 75% sequence identity to the mature polypeptide of SEQ ID NO: 2 or SEQ ID NO: 12; at least 80% sequence identity to the mature polypeptide of SEQ ID NO: 6, SEQ ID NO: 8, or SEQ ID NO: 10; or at least 85% sequence identity to the mature polypeptide of SEQ ID NO: 4;

(b) a polypeptide encoded by a polynucleotide that hybridizes under at least high stringency conditions with (i) the mature polypeptide coding sequence of SEQ ID NO: 1 or the cDNA sequence thereof, SEQ ID NO: 3 or the cDNA sequence thereof, SEQ ID NO: 5 or the cDNA sequence thereof, SEQ ID NO: 7, SEQ ID NO: 9, or SEQ ID NO: 11, or (ii) the full-length complement of (i);

(c) a polypeptide encoded by a polynucleotide having at least 75% sequence identity to the mature polypeptide coding sequence of SEQ ID NO: 1, or the cDNA sequence thereof, or SEQ ID NO: 11; at least 80% sequence identity to the mature polypeptide coding sequence of SEQ ID NO: 5, or the cDNA sequence thereof, SEQ ID NO: 7, or SEQ ID NO: 9; or at least 85% sequence identity to the mature polypeptide coding sequence of SEQ ID NO: 3 or the cDNA sequence thereof;

(d) a variant of the mature polypeptide of SEQ ID NO: 2, SEQ ID NO: 4, SEQ ID NO: 6, SEQ ID NO: 8, SEQ ID NO: 10, or SEQ ID NO: 12 comprising a substitution, deletion, and/or insertion at one or more (e.g., several) positions; and (e) a fragment of the polypeptide of (a), (b), (c), or (d) that has beta-glucosidase activity, beta-xylosidase activity, or beta-glucosidase and beta-xylosidase activity.

The present invention also relates to isolated polynucleotides encoding the polypeptides of the present invention; nucleic acid constructs, recombinant expression vectors, and recombinant host cells comprising the polynucleotides; and methods of producing the polypeptides.

The present invention also relates to processes for degrading or converting a cellulosic material or xylan-containing material, comprising: treating the cellulosic material or xylan-containing material with an enzyme composition in the presence of a polypeptide having beta-glucosidase activity, beta-xylosidase activity, or beta-glucosidase and beta-xylosidase activity of the present invention.

The present invention also relates to processes of producing a fermentation product, comprising: (a) saccharifying a cellulosic material or xylan-containing material with an enzyme composition in the presence of a polypeptide having beta-glucosidase activity, beta-xylosidase activity, or beta-glucosidase and beta-xylosidase activity of the present invention; (b) fermenting the saccharified cellulosic material or xylan-containing material with one or more (e.g., several) fermenting microorganisms to produce the fermentation product; and (c) recovering the fermentation product from the fermentation.

The present invention also relates to processes of fermenting a cellulosic material or xylan-containing material, comprising: fermenting the cellulosic material or xylan-containing material with one or more (e.g., several) fermenting microorganisms, wherein the cellulosic material or xylan-containing material is saccharified with an enzyme composition in the presence of a polypeptide having beta-glucosidase activity, beta-xylosidase activity, or beta-glucosidase and beta-xylosidase activity of the present invention.

The present invention also relates to a polynucleotide encoding a signal peptide comprising or consisting of amino acids 1 to 21 of SEQ ID NO: 2, amino acids 1 to 18 of SEQ ID NO: 4, amino acids 1 to 19 of SEQ ID NO: 6, amino acids 1 to 21 of SEQ ID NO: 8, amino acids 1 to 17 of SEQ ID NO: 10, or amino acids 1 to 17 of SEQ ID NO: 12, which is operably linked to a gene encoding a protein, wherein the gene is foreign to the polynucleotide encoding the signal peptide; nucleic acid constructs, expression vectors, and recombinant host cells comprising the polynucleotides; and methods of producing a protein.

Definitions

Acetylxylan esterase: The term "acetylxylan esterase" means a carboxylesterase (EC 3.1.1.72) that catalyzes the hydrolysis of acetyl groups from polymeric xylan, acetylated xylose, acetylated glucose, alpha-napthyl acetate, and p-nitrophenyl acetate. For purposes of the present invention, acetylxylan esterase activity is determined using 0.5 mM p-nitrophenylacetate as substrate in 50 mM sodium acetate pH 5.0 containing 0.01% TWEEN™ 20 (polyoxyethylene sorbitan monolaurate). One unit of acetylxylan esterase is defined as the amount of enzyme capable of releasing 1 pmole of p-nitrophenolate anion per minute at pH 5, 25° C.

Allelic variant: The term "allelic variant" means any of two or more alternative forms of a gene occupying the same chromosomal locus. Allelic variation arises naturally through mutation, and may result in polymorphism within populations. Gene mutations can be silent (no change in the encoded polypeptide) or may encode polypeptides having altered amino acid sequences. An allelic variant of a polypeptide is a polypeptide encoded by an allelic variant of a gene.

Alpha-L-arabinofuranosidase: The term "alpha-L-arabinofuranosidase" means an alpha-L-arabinofuranoside arabinofuranohydrolase (EC 3.2.1.55) that catalyzes the hydrolysis of terminal non-reducing alpha-L-arabinofuranoside residues in alpha-L-arabinosides. The enzyme acts on alpha-L-arabinofuranosides, alpha-L-arabinans containing (1,3)- and/or (1,5)-linkages, arabinoxylans, and arabinogalactans. Alpha-L-arabinofuranosidase is also known as ara-binosidase, alpha-arabinosidase, alpha-L-arabinosidase, alpha-arabinofuranosidase, polysaccharide alpha-L-arabinofuranosidase, alpha-L-arabinofuranoside hydrolase, L-arabinosidase, or alpha-L-arabinanase. For purposes of the present invention, alpha-L-arabinofuranosidase activity is determined using 5 mg of medium viscosity wheat arabinoxylan (Megazyme International Ireland, Ltd., Bray, Co. Wicklow, Ireland) per ml of 100 mM sodium acetate pH 5 in a total volume of 200 μl for 30 minutes at 40° C. followed by arabinose analysis by AMINEX® HPX-87H column chromatography (Bio-Rad Laboratories, Inc., Hercules, Calif., USA).

Alpha-glucuronidase: The term "alpha-glucuronidase" means an alpha-D-glucosiduronate glucuronohydrolase (EC 3.2.1.139) that catalyzes the hydrolysis of an alpha-D-glucuronoside to D-glucuronate and an alcohol. For purposes of the present invention, alpha-glucuronidase activity is determined according to de Vries, 1998, J. Bacteriol. 180: 243-249. One unit of alpha-glucuronidase equals the amount of enzyme capable of releasing 1 pmole of glucuronic or 4-O-methyl-glucuronic acid per minute at pH 5, 40° C.

Beta-glucosidase: The term "beta-glucosidase" means a beta-D-glucoside glucohydrolase (E.C. 3.2.1.21) that catalyzes the hydrolysis of terminal non-reducing beta-D-glucose residues with the release of beta-D-glucose. For purposes of the present invention, beta-glucosidase activity is determined using p-nitrophenyl-beta-D-glucopyranoside as substrate according to the procedure of Venturi et al., 2002, Extracellular beta-D-glucosidase from Chaetomium thermophilum var. coprophilum: production, purification and some biochemical properties, J. Basic Microbiol. 42: 55-66. One unit of beta-glucosidase is defined as 1.0 pmole of p-nitrophenolate anion produced per minute at 25° C., pH 4.8 from 1 mM p-nitrophenyl-beta-D-glucopyranoside as substrate in 50 mM sodium citrate containing 0.01% TWEEN® 20.

The polypeptides of the present invention have at least 20%, e.g., at least 40%, at least 50%, at least 60%, at least 70%, at least 80%, at least 90%, at least 95%, and at least 100% of the beta-glucosidase activity of the mature polypeptide of SEQ ID NO: 2, SEQ ID NO: 4, SEQ ID NO: 6, SEQ ID NO: 8, SEQ ID NO: 10, or SEQ ID NO: 12.

Beta-xylosidase: The term "beta-xylosidase" means a beta-D-xyloside xylohydrolase (E.C. 3.2.1.37) that catalyzes the exo-hydrolysis of short beta-(4)-xylooligosaccharides to remove successive D-xylose residues from non-reducing termini. For purposes of the present invention, one unit of beta-xylosidase is defined as 1.0 pmole of p-nitrophenolate anion produced per minute at 40° C., pH 5 from 1 mM p-nitrophenyl-beta-D-xyloside as substrate in 100 mM sodium citrate containing 0.01% TWEEN® 20.

The polypeptides of the present invention have at least 20%, e.g., at least 40%, at least 50%, at least 60%, at least 70%, at least 80%, at least 90%, at least 95%, and at least 100% of the beta-xylosidase activity of the mature polypeptide of SEQ ID NO: 2, SEQ ID NO: 4, SEQ ID NO: 6, SEQ ID NO: 8, SEQ ID NO: 10, or SEQ ID NO: 12.

cDNA: The term "cDNA" means a DNA molecule that can be prepared by reverse transcription from a mature, spliced, mRNA molecule obtained from a eukaryotic or prokaryotic cell. cDNA lacks intron sequences that may be present in the corresponding genomic DNA. The initial, primary RNA transcript is a precursor to mRNA that is processed through a series of steps, including splicing, before appearing as mature spliced mRNA.

Cellobiohydrolase: The term "cellobiohydrolase" means a 1,4-beta-D-glucan cellobiohydrolase (E.C. 3.2.1.91) that catalyzes the hydrolysis of 1,4-beta-D-glucosidic linkages in cellulose, cellooligosaccharides, or any beta-1,4-linked glucose containing polymer, releasing cellobiose from the reducing or non-reducing ends of the chain (Teeri, 1997, Crystalline cellulose degradation: New insight into the function of cellobiohydrolases, Trends in Biotechnology 15: 160-167; Teeri et al., 1998, Trichoderma reesei cellobiohydrolases: why so efficient on crystalline cellulose?, Biochem. Soc. Trans. 26: 173-178). For purposes of the present invention, cellobiohydrolase activity is determined according to the procedures described by Lever et al., 1972, Anal. Biochem. 47: 273-279; van Tilbeurgh et al., 1982, FEBS Letters, 149: 152-156; van Tilbeurgh and Claeyssens, 1985, FEBS Letters, 187: 283-288; and Tomme et al., 1988, Eur. J. Biochem. 170: 575-581. In the present invention, the Lever et al. method can be employed to assess hydrolysis of cellulose in corn stover, while the methods of van Tilbeurgh et al. and Tomme et al. can be used to determine the cellobiohydrolase activity on a fluorescent disaccharide derivative, 4-methylumbelliferyl-beta-D-lactoside.

Cellulosic material: The term "cellulosic material" means any material containing cellulose. The predominant polysaccharide in the primary cell wall of biomass is cellulose, the second most abundant is hemicellulose, and the third is pectin. The secondary cell wall, produced after the cell has stopped growing, also contains polysaccharides and is strengthened by polymeric lignin covalently cross-linked to hemicellulose. Cellulose is a homopolymer of anhydrocellobiose and thus a linear beta-(1-4)-D-glucan, while hemicelluloses include a variety of compounds, such as xylans, xyloglucans, arabinoxylans, and mannans in complex branched structures with a spectrum of substituents. Although generally polymorphous, cellulose is found in plant tissue primarily as an insoluble crystalline matrix of parallel glucan chains. Hemicelluloses usually hydrogen bond to cellulose, as well as to other hemicelluloses, which help stabilize the cell wall matrix.

Cellulose is generally found, for example, in the stems, leaves, hulls, husks, and cobs of plants or leaves, branches, and wood of trees. The cellulosic material can be, but is not limited to, agricultural residue, herbaceous material (including energy crops), municipal solid waste, pulp and paper mill residue, waste paper, and wood (including forestry residue) (see, for example, Wiselogel et al., 1995, in Handbook on Bioethanol (Charles E. Wyman, editor), pp. 105-118, Taylor & Francis, Washington D.C.; Wyman, 1994, *Bioresource Technology* 50: 3-16; Lynd, 1990, *Applied Biochemistry and Biotechnology* 24/25: 695-719; Mosier et al., 1999, Recent Progress in Bioconversion of Lignocellulosics, in *Advances in Biochemical Engineering/Biotechnology*, T. Scheper, managing editor, Volume 65, pp. 23-40, Springer-Verlag, New York). It is understood herein that the cellulose may be in the form of lignocellulose, a plant cell wall material containing lignin, cellulose, and hemicellulose in a mixed matrix. In a preferred aspect, the cellulosic material is any biomass material. In another preferred aspect, the cellulosic material is lignocellulose, which comprises cellulose, hemicelluloses, and lignin.

In one aspect, the cellulosic material is agricultural residue. In another aspect, the cellulosic material is herbaceous material (including energy crops). In another aspect, the cellulosic material is municipal solid waste. In another aspect, the cellulosic material is pulp and paper mill residue. In another aspect, the cellulosic material is waste paper. In another aspect, the cellulosic material is wood (including forestry residue).

In another aspect, the cellulosic material is arundo. In another aspect, the cellulosic material is bagasse. In another aspect, the cellulosic material is bamboo. In another aspect, the cellulosic material is corn cob. In another aspect, the cellulosic material is corn fiber. In another aspect, the cellulosic material is corn stover. In another aspect, the cellulosic material is miscanthus. In another aspect, the cellulosic material is orange peel. In another aspect, the cellulosic material is rice straw. In another aspect, the cellulosic material is switchgrass. In another aspect, the cellulosic material is wheat straw.

In another aspect, the cellulosic material is aspen. In another aspect, the cellulosic material is eucalyptus. In another aspect, the cellulosic material is fir. In another aspect, the cellulosic material is pine. In another aspect, the cellulosic material is poplar. In another aspect, the cellulosic material is spruce. In another aspect, the cellulosic material is willow.

In another aspect, the cellulosic material is algal cellulose. In another aspect, the cellulosic material is bacterial cellulose. In another aspect, the cellulosic material is cotton linter. In another aspect, the cellulosic material is filter paper. In another aspect, the cellulosic material is microcrystalline cellulose. In another aspect, the cellulosic material is phosphoric-acid treated cellulose.

In another aspect, the cellulosic material is an aquatic biomass. As used herein the term "aquatic biomass" means biomass produced in an aquatic environment by a photosynthesis process. The aquatic biomass can be algae, emergent plants, floating-leaf plants, or submerged plants.

The cellulosic material may be used as is or may be subjected to pretreatment, using conventional methods known in the art, as described herein. In a preferred aspect, the cellulosic material is pretreated.

Cellulolytic enzyme or cellulase: The term "cellulolytic enzyme" or "cellulase" means one or more (e.g., several) enzymes that hydrolyze a cellulosic material. Such enzymes include endoglucanase(s), cellobiohydrolase(s), beta-glucosidase(s), or combinations thereof. The two basic approaches for measuring cellulolytic activity include: (1) measuring the total cellulolytic activity, and (2) measuring the individual cellulolytic activities (endoglucanases, cellobiohydrolases, and beta-glucosidases) as reviewed in Zhang et al., Outlook for cellulase improvement: Screening and selection strategies, 2006, *Biotechnology Advances* 24: 452-481. Total cellulolytic activity is usually measured using insoluble substrates, including Whatman No 1 filter paper, microcrystalline cellulose, bacterial cellulose, algal cellulose, cotton, pretreated lignocellulose, etc. The most common total cellulolytic activity assay is the filter paper assay using Whatman No 1 filter paper as the substrate. The assay was established by the International Union of Pure and Applied Chemistry (IUPAC) (Ghose, 1987, Measurement of cellulase activities, *Pure Appl. Chem.* 59: 257-68).

For purposes of the present invention, cellulolytic enzyme activity is determined by measuring the increase in hydrolysis of a cellulosic material by cellulolytic enzyme(s) under the following conditions: 1-50 mg of cellulolytic enzyme protein/g of cellulose in PCS (or other pretreated cellulosic material) for 3-7 days at a suitable temperature, e.g., 50° C., 55° C., or 60° C., compared to a control hydrolysis without addition of cellulolytic enzyme protein. Typical conditions are 1 ml reactions, washed or unwashed PCS, 5% insoluble solids, 50 mM sodium acetate pH 5, 1 mM $MnSO_4$, 50° C., 55° C., or 60° C., 72 hours, sugar analysis by AMINEX® HPX-87H column (Bio-Rad Laboratories, Inc., Hercules, Calif., USA).

Coding sequence: The term "coding sequence" means a polynucleotide, which directly specifies the amino acid sequence of a polypeptide. The boundaries of the coding sequence are generally determined by an open reading frame, which begins with a start codon such as ATG, GTG, or TTG and ends with a stop codon such as TAA, TAG, or TGA. The coding sequence may be a genomic DNA, cDNA, synthetic DNA, or a combination thereof.

Control sequences: The term "control sequences" means nucleic acid sequences necessary for expression of a polynucleotide encoding a mature polypeptide of the present invention. Each control sequence may be native (i.e., from the same gene) or foreign (i.e., from a different gene) to the polynucleotide encoding the polypeptide or native or foreign to each other. Such control sequences include, but are not limited to, a leader, polyadenylation sequence, propeptide sequence, promoter, signal peptide sequence, and transcription terminator. At a minimum, the control sequences include a promoter, and transcriptional and translational stop signals. The control sequences may be provided with linkers for the purpose of introducing specific restriction sites facilitating ligation of the control sequences with the coding region of the polynucleotide encoding a polypeptide.

Endoglucanase: The term "endoglucanase" means an endo-1,4-(1,3;1,4)-beta-D-glucan 4-glucanohydrolase (E.C. 3.2.1.4) that catalyzes endohydrolysis of 1,4-beta-D-glycosidic linkages in cellulose, cellulose derivatives (such as carboxymethyl cellulose and hydroxyethyl cellulose), lichenin, beta-1,4 bonds in mixed beta-1,3 glucans such as cereal beta-D-glucans or xyloglucans, and other plant material containing cellulosic components. Endoglucanase activity can be determined by measuring reduction in substrate viscosity or increase in reducing ends determined by a reducing sugar assay (Zhang et al., 2006, *Biotechnology Advances* 24: 452-481). For purposes of the present invention, endoglucanase activity is determined using carboxymethyl cellulose (CMC) as substrate according to the procedure of Ghose, 1987, *Pure and Appl. Chem.* 59: 257-268, at pH 5, 40° C.

Expression: The term "expression" includes any step involved in the production of a polypeptide including, but not limited to, transcription, post-transcriptional modification, translation, post-translational modification, and secretion.

Expression vector: The term "expression vector" means a linear or circular DNA molecule that comprises a polynucleotide encoding a polypeptide and is operably linked to control sequences that provide for its expression.

Family 61 glycoside hydrolase: The term "Family 61 glycoside hydrolase" or "Family GH61" or "GH61" means a polypeptide falling into the glycoside hydrolase Family 61 according to Henrissat B., 1991, A classification of glycosyl hydrolases based on amino-acid sequence similarities, *Biochem. J.* 280: 309-316, and Henrissat B., and Bairoch A., 1996, Updating the sequence-based classification of glycosyl hydrolases, *Biochem. J.* 316: 695-696. The enzymes in this family were originally classified as a glycoside hydrolase family based on measurement of very weak endo-1,4-beta-D-glucanase activity in one family member. The structure and mode of action of these enzymes are non-canonical and they cannot be considered as bona fide glycosidases. However, they are kept in the CAZy classification on the basis of their capacity to enhance the breakdown of lignocellulose when used in conjunction with a cellulase or a mixture of cellulases.

Feruloyl esterase: The term "feruloyl esterase" means a 4-hydroxy-3-methoxycinnamoyl-sugar hydrolase (EC 3.1.1.73) that catalyzes the hydrolysis of 4-hydroxy-3-methoxycinnamoyl (feruloyl) groups from esterified sugar, which is usually arabinose in "natural" substrates, to produce ferulate (4-hydroxy-3-methoxycinnamate). Feruloyl esterase is also known as ferulic acid esterase, hydroxycinnamoyl esterase, FAE-III, cinnamoyl ester hydrolase, FAEA, cinnAE, FAE-I, or FAE-II. For purposes of the present invention, feruloyl esterase activity is determined using 0.5 mM p-nitrophenylferulate as substrate in 50 mM sodium acetate pH 5.0. One unit of feruloyl esterase equals the amount of enzyme capable of releasing 1 pmole of p-nitrophenolate anion per minute at pH 5, 25° C.

Fragment: The term "fragment" means a polypeptide having one or more (e.g., several) amino acids deleted from the amino and/or carboxyl terminus of a mature polypeptide; wherein the fragment has beta-glucosidase activity, beta-xylosidase activity, or beta-glucosidase and beta-xylosidase activity. In one aspect, a fragment contains at least 640 amino acid residues, e.g., at least 680 amino acid residues or at least 720 amino acid residues of SEQ ID NO: 2. In another aspect, a fragment contains at least 640 amino acid residues, e.g., at least 680 amino acid residues or at least 720 amino acid residues of SEQ ID NO: 4. In another aspect, a fragment contains at least 660 amino acid residues, e.g., at least 695 amino acid residues or at least 730 amino acid residues of SEQ ID NO: 6. In another aspect, a fragment contains at least 650 amino acid residues, e.g., at least 685 amino acid residues or at least 720 amino acid residues of SEQ ID NO: 8. In another aspect, a fragment contains at least 670 amino acid residues, e.g., at least 710 amino acid residues or at least 750 amino acid residues of SEQ ID NO: 10. In another aspect, a fragment contains at least 670 amino acid residues, e.g., at least 710 amino acid residues or at least 750 amino acid residues of SEQ ID NO: 12.

Hemicellulolytic enzyme or hemicellulase: The term "hemicellulolytic enzyme" or "hemicellulase" means one or more (e.g., several) enzymes that hydrolyze a hemicellulosic material. See, for example, Shallom, D. and Shoham, Y. Microbial hemicellulases. *Current Opinion In Microbiology*, 2003, 6(3): 219-228). Hemicellulases are key components in the degradation of plant biomass. Examples of hemicellulases include, but are not limited to, an acetylmannan esterase, an acetylxylan esterase, an arabinanase, an arabinofuranosidase, a coumaric acid esterase, a feruloyl esterase, a galactosidase, a glucuronidase, a glucuronoyl esterase, a mannanase, a mannosidase, a xylanase, and a xylosidase. The substrates of these enzymes, the hemicelluloses, are a heterogeneous group of branched and linear polysaccharides that are bound via hydrogen bonds to the cellulose microfibrils in the plant cell wall, crosslinking them into a robust network. Hemicelluloses are also covalently attached to lignin, forming together with cellulose a highly complex structure. The variable structure and organization of hemicelluloses require the concerted action of many enzymes for its complete degradation. The catalytic modules of hemicellulases are either glycoside hydrolases (GHs) that hydrolyze glycosidic bonds, or carbohydrate esterases (CEs), which hydrolyze ester linkages of acetate or ferulic acid side groups. These catalytic modules, based on homology of their primary sequence, can be assigned into GH and CE families. Some families, with an overall similar fold, can be further grouped into clans, marked alphabetically (e.g., GH-A). A most informative and updated classification of these and other carbohydrate active enzymes is available in the Carbohydrate-Active Enzymes (CAZy) database. Hemicellulolytic enzyme activities can be measured according to Ghose and Bisaria, 1987, *Pure & Appl. Chem.* 59: 1739-1752, at a suitable temperature, e.g., 50° C., 55° C., or 60° C., and pH, e.g., 5.0 or 5.5.

High stringency conditions: The term "high stringency conditions" means for probes of at least 100 nucleotides in length, prehybridization and hybridization at 42° C. in 5×SSPE, 0.3% SDS, 200 micrograms/ml sheared and denatured salmon sperm DNA, and 50% formamide, following standard Southern blotting procedures for 12 to 24 hours. The carrier material is finally washed three times each for 15 minutes using 2×SSC, 0.2% SDS at 65° C.

Host cell: The term "host cell" means any cell type that is susceptible to transformation, transfection, transduction, or the like with a nucleic acid construct or expression vector comprising a polynucleotide of the present invention. The term "host cell" encompasses any progeny of a parent cell that is not identical to the parent cell due to mutations that occur during replication.

Isolated: The term "isolated" means a substance in a form or environment that does not occur in nature. Non-limiting examples of isolated substances include (1) any non-naturally occurring substance, (2) any substance including, but not limited to, any enzyme, variant, nucleic acid, protein, peptide or cofactor, that is at least partially removed from one or more or all of the naturally occurring constituents with which it is associated in nature; (3) any substance modified by the hand of man relative to that substance found in nature; or (4) any substance modified by increasing the amount of the substance relative to other components with which it is naturally associated (e.g., multiple copies of a gene encoding the substance; use of a stronger promoter than the promoter naturally associated with the gene encoding the substance). The polypeptide of the present invention may be used in industrial applications in the form of a fermentation broth product, that is, the polypeptide of the present invention is a component of a fermentation broth used as a product in industrial applications (e.g., ethanol production). The fermentation broth product will in addition to the polypeptide of the present invention comprise additional ingredients used in the fermentation process, such as, for example, cells (including, the host cells containing the gene encoding the polypeptide of the present invention which are used to produce the polypeptide of interest), cell debris, biomass, fermentation media and/or fermentation products. The fermentation broth may optionally be subjected to one or more purification (including filtration) steps to remove or reduce one more components of a fermentation process. Accordingly, an isolated substance may be present in such a fermentation broth product.

Low stringency conditions: The term "low stringency conditions" means for probes of at least 100 nucleotides in length, prehybridization and hybridization at 42° C. in 5×SSPE, 0.3% SDS, 200 micrograms/ml sheared and denatured salmon sperm DNA, and 25% formamide, following standard Southern blotting procedures for 12 to 24 hours. The carrier material is finally washed three times each for 15 minutes using 2×SSC, 0.2% SDS at 50° C.

Mature polypeptide: The term "mature polypeptide" means a polypeptide in its final form following translation and any post-translational modifications, such as N-terminal processing, C-terminal truncation, glycosylation, phosphorylation, etc. In one aspect, the mature polypeptide is amino acids 22 to 782 of SEQ ID NO: 2 based on the SignalP program (Nielsen et al., 1997, *Protein Engineering* 10:1-6) that predicts amino acids 1 to 21 of SEQ ID NO: 2 are a signal peptide. In another aspect, the mature polypeptide is amino acids 19 to 776 of SEQ ID NO: 4 based on the SignalP program that predicts amino acids 1 to 18 of SEQ ID NO: 4 are a signal peptide. In another aspect, the mature polypeptide is amino acids 20 to 768 of SEQ ID NO: 6 based on the SignalP program that predicts amino acids 1 to 19 of SEQ ID NO: 6 are a signal peptide. In another aspect, the mature polypeptide is amino acids 22 to 781 of SEQ ID NO: 8 based on the SignalP program that predicts amino acids 1 to 21 of SEQ ID NO: 8 are a signal peptide. In another aspect, the mature polypeptide is amino acids 18 to 811 of SEQ ID NO: 10 based on the SignalP program that predicts amino acids 1 to 17 of SEQ ID NO: 10 are a signal peptide. In another aspect, the mature polypeptide is amino acids 18 to 803 of SEQ ID NO: 12 based on the SignalP program that predicts amino acids 1 to 17 of SEQ ID NO: 12 are a signal peptide. It is known in the art that a host cell may produce a mixture of two of more different mature polypeptides (i.e., with a different C-terminal and/or N-terminal amino acid) expressed by the same polynucleotide.

Mature polypeptide coding sequence: The term "mature polypeptide coding sequence" means a polynucleotide that encodes a mature polypeptide having beta-glucosidase activity, beta-xylosidase activity, or beta-glucosidase and beta-xylosidase activity. In one aspect, the mature polypeptide coding sequence is nucleotides 64 to 2707 of SEQ ID NO: 1 based on the SignalP program (Nielsen et al., 1997, supra) that predicts nucleotides 1 to 63 of SEQ ID NO: 1 encode a signal peptide. In another aspect, the mature polypeptide coding sequence is the cDNA sequence contained in nucleotides 64 to 2707 of SEQ ID NO: 1. In another aspect, the mature polypeptide coding sequence is nucleotides 55 to 2557 of SEQ ID NO: 3 based on the SignalP program that predicts nucleotides 1 to 54 of SEQ ID NO: 3 encode a signal peptide. In another aspect, the mature polypeptide coding sequence is the cDNA sequence contained in nucleotides 55 to 2557 of SEQ ID NO: 3. In another aspect, the mature polypeptide coding sequence is nucleotides 58 to 2630 of SEQ ID NO: 5 based on the SignalP program that predicts nucleotides 1 to 57 of SEQ ID NO: 5 encode a signal peptide. In another aspect, the mature polypeptide coding sequence is the cDNA sequence contained in nucleotides 58 to 2630 of SEQ ID NO: 5. In another aspect, the mature polypeptide coding sequence is nucleotides 64 to 2343 of SEQ ID NO: 7 based on the SignalP program that predicts nucleotides 1 to 63 of SEQ ID NO: 7 encode a signal peptide. In another aspect, the mature polypeptide coding sequence is nucleotides 52 to 2433 of SEQ ID NO: 9 based on the SignalP program that predicts nucleotides 1 to 51 of SEQ ID NO: 9 encode a signal peptide. In another aspect, the mature polypeptide coding sequence is nucleotides 52 to 2409 of SEQ ID NO: 11 based on the SignalP program that predicts nucleotides 1 to 51 of SEQ ID NO: 11 encode a signal peptide.

Medium stringency conditions: The term "medium stringency conditions" means for probes of at least 100 nucleotides in length, prehybridization and hybridization at 42° C. in 5×SSPE, 0.3% SDS, 200 micrograms/ml sheared and denatured salmon sperm DNA, and 35% formamide, following standard Southern blotting procedures for 12 to 24 hours. The carrier material is finally washed three times each for 15 minutes using 2×SSC, 0.2% SDS at 55° C.

Medium-high stringency conditions: The term "medium-high stringency conditions" means for probes of at least 100 nucleotides in length, prehybridization and hybridization at 42° C. in 5×SSPE, 0.3% SDS, 200 micrograms/ml sheared and denatured salmon sperm DNA, and 35% formamide, following standard Southern blotting procedures for 12 to 24 hours. The carrier material is finally washed three times each for 15 minutes using 2×SSC, 0.2% SDS at 60° C.

Nucleic acid construct: The term "nucleic acid construct" means a nucleic acid molecule, either single- or double-stranded, which is isolated from a naturally occurring gene or is modified to contain segments of nucleic acids in a manner that would not otherwise exist in nature or which is synthetic, which comprises one or more control sequences.

Operably linked: The term "operably linked" means a configuration in which a control sequence is placed at an appropriate position relative to the coding sequence of a polynucleotide such that the control sequence directs expression of the coding sequence.

Polypeptide having cellulolytic enhancing activity: The term "polypeptide having cellulolytic enhancing activity" means a GH61 polypeptide that catalyzes the enhancement of the hydrolysis of a cellulosic material by enzyme having cellulolytic activity. For purposes of the present invention, cellulolytic enhancing activity is determined by measuring the increase in reducing sugars or the increase of the total of cellobiose and glucose from the hydrolysis of a cellulosic material by cellulolytic enzyme under the following conditions: 1-50 mg of total protein/g of cellulose in PCS, wherein total protein is comprised of 50-99.5% w/w cellulolytic enzyme protein and 0.5-50% w/w protein of a GH61 polypeptide having cellulolytic enhancing activity for 1-7 days at a suitable temperature, e.g., 50° C., 55° C., or 60° C., and pH, e.g., 5.0 or 5.5, compared to a control hydrolysis with equal total protein loading without cellulolytic enhancing activity (1-50 mg of cellulolytic protein/g of cellulose in PCS). In a preferred aspect, a mixture of CELLUCLAST® 1.5L (Novozymes A/S, Bagsværd, Denmark) in the presence of 2-3% of total protein weight *Aspergillus oryzae* beta-glucosidase (recombinantly produced in *Aspergillus oryzae* according to WO 02/095014) or 2-3% of total protein weight *Aspergillus fumigatus* beta-glucosidase (recombinantly produced in

*Aspergillus oryzae* as described in WO 2002/095014) of cellulase protein loading is used as the source of the cellulolytic activity.

The GH61 polypeptides having cellulolytic enhancing activity enhance the hydrolysis of a cellulosic material catalyzed by enzyme having cellulolytic activity by reducing the amount of cellulolytic enzyme required to reach the same degree of hydrolysis preferably at least 1.01-fold, e.g., at least 1.05-fold, at least 1.10-fold, at least 1.25-fold, at least 1.5-fold, at least 2-fold, at least 3-fold, at least 4-fold, at least 5-fold, at least 10-fold, or at least 20-fold.

Pretreated corn stover: The term "PCS" or "Pretreated Corn Stover" means a cellulosic material derived from corn stover by treatment with heat and dilute sulfuric acid.

Sequence identity: The relatedness between two amino acid sequences or between two nucleotide sequences is described by the parameter "sequence identity".

For purposes of the present invention, the sequence identity between two amino acid sequences is determined using the Needleman-Wunsch algorithm (Needleman and Wunsch, 1970, *J. Mol. Biol.* 48: 443-453) as implemented in the Needle program of the EMBOSS package (EMBOSS: The European Molecular Biology Open Software Suite, Rice et al., 2000, *Trends Genet.* 16: 276-277), preferably version 3.0.0, 5.0.0, or later. The parameters used are gap open penalty of 10, gap extension penalty of 0.5, and the EBLOSUM62 (EMBOSS version of BLOSUM62) substitution matrix. The output of Needle labeled "longest identity" (obtained using the -nobrief option) is used as the percent identity and is calculated as follows:

$$(\text{Identical Residues} \times 100)/(\text{Length of Alignment} - \text{Total Number of Gaps in Alignment})$$

For purposes of the present invention, the sequence identity between two deoxyribonucleotide sequences is determined using the Needleman-Wunsch algorithm (Needleman and Wunsch, 1970, supra) as implemented in the Needle program of the EMBOSS package (EMBOSS: The European Molecular Biology Open Software Suite, Rice et al., 2000, supra), preferably version 5.0.0 or later. The parameters used are gap open penalty of 10, gap extension penalty of 0.5, and the EDNAFULL (EMBOSS version of NCBI NUC4.4) substitution matrix. The output of Needle labeled "longest identity" (obtained using the -nobrief option) is used as the percent identity and is calculated as follows:

$$(\text{Identical Deoxyribonucleotides} \times 100)/(\text{Length of Alignment} - \text{Total Number of Gaps in Alignment})$$

Subsequence: The term "subsequence" means a polynucleotide having one or more (e.g., several) nucleotides absent from the 5' and/or 3' end of a mature polypeptide coding sequence; wherein the subsequence encodes a fragment having beta-glucosidase activity, beta-xylosidase activity, or beta-glucosidase and beta-xylosidase activity. In one aspect, a subsequence contains at least 1920 nucleotides, e.g., at least 2040 nucleotides or at least 2160 nucleotides of SEQ ID NO: 1. In another aspect, a subsequence contains at least 1920 nucleotides, e.g., at least 2040 nucleotides or at least 2160 nucleotides of SEQ ID NO: 3. In another aspect, a subsequence contains at least 1980 nucleotides, e.g., at least 2085 nucleotides or at least 2190 nucleotides of SEQ ID NO: 5. In another aspect, a subsequence contains at least 1950 nucleotides, e.g., at least 2055 nucleotides or at least 2160 nucleotides of SEQ ID NO: 7. In another aspect, a subsequence contains at least 2010 nucleotides, e.g., at least 2130 nucleotides or at least 2250 nucleotides of SEQ ID NO: 9. In another aspect, a subsequence contains at least 2010 nucleotides, e.g., at least 2130 nucleotides or at least 2250 nucleotides of SEQ ID NO: 11.

Variant: The term "variant" means a polypeptide having beta-glucosidase activity, beta-xylosidase activity, or beta-glucosidase and beta-xylosidase activity comprising an alteration, i.e., a substitution, insertion, and/or deletion, at one or more (e.g., several) positions. A substitution means replacement of the amino acid occupying a position with a different amino acid; a deletion means removal of the amino acid occupying a position; and an insertion means adding an amino acid adjacent to and immediately following the amino acid occupying a position.

Xylan-containing material: The term "xylan-containing material" means any material comprising a plant cell wall polysaccharide containing a backbone of beta-(1-4)-linked xylose residues. Xylans of terrestrial plants are heteropolymers possessing a beta-(1-4)-D-xylopyranose backbone, which is branched by short carbohydrate chains. They comprise D-glucuronic acid or its 4-O-methyl ether, L-arabinose, and/or various oligosaccharides, composed of D-xylose, L-arabinose, D- or L-galactose, and D-glucose. Xylan-type polysaccharides can be divided into homoxylans and heteroxylans, which include glucuronoxylans, (arabino)glucuronoxylans, (glucurono)arabinoxylans, arabinoxylans, and complex heteroxylans. See, for example, Ebringerova et al., 2005, *Adv. Polym. Sci.* 186: 1-67. In the methods of the present invention, any material containing xylan may be used. In a preferred aspect, the xylan-containing material is lignocellulose.

Xylan degrading activity or xylanolytic activity: The term "xylan degrading activity" or "xylanolytic activity" means a biological activity that hydrolyzes xylan-containing material. The two basic approaches for measuring xylanolytic activity include: (1) measuring the total xylanolytic activity, and (2) measuring the individual xylanolytic activities (e.g., endoxylanases, beta-xylosidases, arabinofuranosidases, alpha-glucuronidases, acetylxylan esterases, feruloyl esterases, and alpha-glucuronyl esterases). Recent progress in assays of xylanolytic enzymes was summarized in several publications including Biely and Puchard, Recent progress in the assays of xylanolytic enzymes, 2006, *Journal of the Science of Food and Agriculture* 86(11): 1636-1647; Spanikova and Biely, 2006, Glucuronoyl esterase—Novel carbohydrate esterase produced by Schizophyllum commune, *FEBS Letters* 580 (19): 4597-4601; Herrmann, Vrsanska, Jurickova, Hirsch, Biely, and Kubicek, 1997, The beta-D-xylosidase of *Trichoderma reesei* is a multifunctional beta-D-xylan xylohydrolase, *Biochemical Journal* 321: 375-381.

Total xylan degrading activity can be measured by determining the reducing sugars formed from various types of xylan, including, for example, oat spelt, beechwood, and larchwood xylans, or by photometric determination of dyed xylan fragments released from various covalently dyed xylans. The most common total xylanolytic activity assay is based on production of reducing sugars from polymeric 4-O-methyl glucuronoxylan as described in Bailey, Biely, Poutanen, 1992, Interlaboratory testing of methods for assay of xylanase activity, *Journal of Biotechnology* 23(3): 257-270. Xylanase activity can also be determined with 0.2% AZCL-arabinoxylan as substrate in 0.01% TRITON® X-100 (4-(1,1,3,3-tetramethylbutyl)phenyl-polyethylene glycol) and 200 mM sodium phosphate buffer pH 6 at 37° C. One unit of xylanase activity is defined as 1.0 mmole of azurine produced per minute at 37° C., pH 6 from 0.2% AZCL-arabinoxylan as substrate in 200 mM sodium phosphate pH 6 buffer.

For purposes of the present invention, xylan degrading activity is determined by measuring the increase in hydrolysis of birchwood xylan (Sigma Chemical Co., Inc., St. Louis, Mo., USA) by xylan-degrading enzyme(s) under the following typical conditions: 1 ml reactions, 5 mg/ml substrate (total solids), 5 mg of xylanolytic protein/g of substrate, 50 mM sodium acetate pH 5, 50° C., 24 hours, sugar analysis using p-hydroxybenzoic acid hydrazide (PHBAH) assay as described by Lever, 1972, A new reaction for colorimetric determination of carbohydrates, *Anal. Biochem* 47: 273-279.

Xylanase: The term "xylanase" means a 1,4-beta-D-xylan-xylohydrolase (E.C. 3.2.1.8) that catalyzes the endohydrolysis of 1,4-beta-D-xylosidic linkages in xylans. For purposes of the present invention, xylanase activity is determined with 0.2% AZCL-arabinoxylan as substrate in 0.01% TRITON® X-100 and 200 mM sodium phosphate buffer pH 6 at 37° C. One unit of xylanase activity is defined as 1.0 μmole of azurine produced per minute at 37° C., pH 6 from 0.2% AZCL-arabinoxylan as substrate in 200 mM sodium phosphate pH 6 buffer.

DETAILED DESCRIPTION OF THE INVENTION

Polypeptides Having Beta-Glucosidase Activity, Beta-Xylosidase Activity, or Beta-Glucosidase and Beta-Xylosidase Activity In an embodiment, the present invention relates to isolated polypeptides having a sequence identity to the mature polypeptide of SEQ ID NO: 2 or SEQ ID NO: 12 of at least 75%, e.g., at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100%; the mature polypeptide of SEQ ID NO: 6, SEQ ID NO: 8, or SEQ ID NO: 10 of at least 80%, e.g., at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100%; or the mature polypeptide of SEQ ID NO: 4 of at least 85%, e.g., at least 86%, at least 87%, at least 88%, at least 89%, at least 90%, at least 91%, at least 92%, at least 93%, at least 94%, at least 95%, at least 96%, at least 97%, at least 98%, at least 99%, or 100%; which have beta-glucosidase activity, beta-xylosidase activity, or beta-glucosidase and beta-xylosidase activity. In one aspect, the polypeptides differ by up to 10 amino acids, e.g., 1, 2, 3, 4, 5, 6, 7, 8, 9, or 10, from the mature polypeptide of SEQ ID NO: 2, SEQ ID NO: 4, SEQ ID NO: 6, SEQ ID NO: 8, SEQ ID NO: 10, or SEQ ID NO: 12.

A polypeptide of the present invention preferably comprises or consists of the amino acid sequence of SEQ ID NO: 2, SEQ ID NO: 4, SEQ ID NO: 6, SEQ ID NO: 8, SEQ ID NO: 10, or SEQ ID NO: 12; or an allelic variant thereof; or is a fragment thereof having beta-glucosidase activity, beta-xylosidase activity, or beta-glucosidase and beta-xylosidase activity. In another aspect, the polypeptide comprises or consists of the mature polypeptide of SEQ ID NO: 2, SEQ ID NO: 4, SEQ ID NO: 6, SEQ ID NO: 8, SEQ ID NO: 10, or SEQ ID NO: 12. In another aspect, the polypeptide comprises or consists of amino acids 22 to 782 of SEQ ID NO: 2. In another aspect, the polypeptide comprises or consists of amino acids 19 to 776 of SEQ ID NO: 4. In another aspect, the polypeptide comprises or consists of amino acids 20 to 768 of SEQ ID NO: 6. In another aspect, the polypeptide comprises or consists of amino acids 22 to 781 of SEQ ID NO: 8. In another aspect, the polypeptide comprises or consists of amino acids 18 to 811 of SEQ ID NO: 10. In another aspect, the polypeptide comprises or consists of amino acids 18 to 803 of SEQ ID NO: 12.

In another embodiment, the present invention relates to isolated polypeptides having beta-glucosidase activity, beta-xylosidase activity, or beta-glucosidase and beta-xylosidase activity that are encoded by polynucleotides that hybridize under very low stringency conditions, low stringency conditions, medium stringency conditions, medium-high stringency conditions, high stringency conditions, or very high stringency conditions with (i) the mature polypeptide coding sequence of SEQ ID NO: 1 or the cDNA sequence thereof, SEQ ID NO: 3 or the cDNA sequence thereof, SEQ ID NO: 5 or the cDNA sequence thereof, SEQ ID NO: 7, SEQ ID NO: 9, or SEQ ID NO: 11, or (ii) the full-length complement of (i) (J. Sambrook, E. F. Fritsch, and T. Maniatis, 1989, *Molecular Cloning, A Laboratory Manual*, 2d edition, Cold Spring Harbor, N.Y.).

The polynucleotide of SEQ ID NO: 1, SEQ ID NO: 3, SEQ ID NO: 5, SEQ ID NO: 7, SEQ ID NO: 9, or SEQ ID NO: 11, or a subsequence thereof, as well as the amino acid sequence of SEQ ID NO: 2, SEQ ID NO: 4, SEQ ID NO: 6, SEQ ID NO: 8, SEQ ID NO: 10, or SEQ ID NO: 12, or a fragment thereof, may be used to design nucleic acid probes to identify and clone DNA encoding polypeptides having beta-glucosidase activity, beta-xylosidase activity, or beta-glucosidase and beta-xylosidase activity from strains of different genera or species according to methods well known in the art. In particular, such probes can be used for hybridization with the genomic DNA or cDNA of a cell of interest, following standard Southern blotting procedures, in order to identify and isolate the corresponding gene therein. Such probes can be considerably shorter than the entire sequence, but should be at least 15, e.g., at least 25, at least 35, or at least 70 nucleotides in length. Preferably, the nucleic acid probe is at least 100 nucleotides in length, e.g., at least 200 nucleotides, at least 300 nucleotides, at least 400 nucleotides, at least 500 nucleotides, at least 600 nucleotides, at least 700 nucleotides, at least 800 nucleotides, or at least 900 nucleotides in length. Both DNA and RNA probes can be used. The probes are typically labeled for detecting the corresponding gene (for example, with $^{32}P$, $^{3}H$, $^{35}S$, biotin, or avidin). Such probes are encompassed by the present invention.

A genomic DNA or cDNA library prepared from such other strains may be screened for DNA that hybridizes with the probes described above and encodes a polypeptide having beta-glucosidase activity, beta-xylosidase activity, or beta-glucosidase and beta-xylosidase activity. Genomic or other DNA from such other strains may be separated by agarose or polyacrylamide gel electrophoresis, or other separation techniques. DNA from the libraries or the separated DNA may be transferred to and immobilized on nitrocellulose or other suitable carrier material. In order to identify a clone or DNA that is homologous with SEQ ID NO: 1, SEQ ID NO: 3, SEQ ID NO: 5, SEQ ID NO: 7, SEQ ID NO: 9, or SEQ ID NO: 11, or a subsequence thereof, the carrier material is used in a Southern blot.

For purposes of the present invention, hybridization indicates that the polynucleotide hybridizes to a labeled nucleic acid probe corresponding to SEQ ID NO: 1 or the cDNA sequence thereof, SEQ ID NO: 3 or the cDNA sequence thereof, SEQ ID NO: 5 or the cDNA sequence thereof, SEQ ID NO: 7, SEQ ID NO: 9, or SEQ ID NO: 11; the mature polypeptide coding sequence of SEQ ID NO: 1, SEQ ID NO: 3, SEQ ID NO: 5, SEQ ID NO: 7, SEQ ID NO: 9, or SEQ ID NO: 11; the full-length complement thereof; or a subsequence thereof; under very low to very high stringency conditions. Molecules to which the nucleic acid probe hybridizes under these conditions can be detected using, for example, X-ray film or any other detection means known in the art.

In one aspect, the nucleic acid probe is the mature polypeptide coding sequence of SEQ ID NO: 1 or the cDNA sequence thereof, SEQ ID NO: 3 or the cDNA sequence thereof, SEQ ID NO: 5 or the cDNA sequence thereof, SEQ ID NO: 7, SEQ ID NO: 9, or SEQ ID NO: 11. In another aspect, the nucleic acid probe is nucleotides 64 to 2707 of SEQ ID NO: 1, nucleotides 55 to 2557 of SEQ ID NO: 3, nucleotides 58 to 2630 of SEQ ID NO: 5, nucleotides 64 to 2343 of SEQ ID NO: 7, nucleotides 52 to 2433 of SEQ ID NO: 9, or nucleotides 52 to 2409 of SEQ ID NO: 11. In another aspect, the nucleic acid probe is a polynucleotide that encodes the polypeptide of SEQ ID NO: 2, SEQ ID NO: 4, SEQ ID NO: 6, SEQ ID NO: 8, SEQ ID NO: 10, or SEQ ID NO: 12, or the mature polypeptide thereof; or a fragment thereof. In another aspect, the nucleic acid probe is SEQ ID NO: 1 or the cDNA sequence thereof, SEQ ID NO: 3 or the cDNA sequence thereof, SEQ ID NO: 5 or the cDNA sequence thereof, SEQ ID NO: 7, SEQ ID NO: 9, or SEQ ID NO: 11.

In another embodiment, the present invention relates to isolated polypeptides having beta-glucosidase activity, beta-xylosidase activity, or beta-glucosidase and beta-xylosidase activity encoded by polynucleotides having a sequence identity to the mature polypeptide coding sequence of SEQ ID NO: 1, or the cDNA sequence thereof, or SEQ ID NO: 11 of at least 75%, e.g., at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100%; the mature polypeptide coding sequence of SEQ ID NO: 5 or the cDNA sequence thereof, SEQ ID NO: 7, or SEQ ID NO: 9 of at least 80%, e.g., at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100%; or the mature polypeptide coding sequence of SEQ ID NO: 3, or the cDNA sequence thereof, of at least 85%, e.g., at least 86%, at least 87%, at least 88%, at least 89%, at least 90%, at least 91%, at least 92%, at least 93%, at least 94%, at least 95%, at least 96%, at least 97%, at least 98%, at least 99%, or 100%.

In another embodiment, the present invention relates to variants of the mature polypeptide of SEQ ID NO: 2, SEQ ID NO: 4, SEQ ID NO: 6, SEQ ID NO: 8, SEQ ID NO: 10, or SEQ ID NO: 12 comprising a substitution, deletion, and/or insertion at one or more (e.g., several) positions. In an embodiment, the number of amino acid substitutions, deletions and/or insertions introduced into the mature polypeptide of SEQ ID NO: 2, SEQ ID NO: 4, SEQ ID NO: 6, SEQ ID NO: 8, SEQ ID NO: 10, or SEQ ID NO: 12 is not more than 10, e.g., 1, 2, 3, 4, 5, 6, 7, 8, 9, or 10. The, amino acid changes may be of a minor nature, that is conservative amino acid substitutions or insertions that do not significantly affect the folding and/or activity of the protein; small deletions, typically of 1-30 amino acids; small amino- or carboxyl-terminal extensions, such as an amino-terminal methionine residue; a small linker peptide of up to 20-25 residues; or a small extension that facilitates purification by changing net charge or another function, such as a poly-histidine tract, an antigenic epitope or a binding domain.

Examples of conservative substitutions are within the groups of basic amino acids (arginine, lysine and histidine), acidic amino acids (glutamic acid and aspartic acid), polar amino acids (glutamine and asparagine), hydrophobic amino acids (leucine, isoleucine and valine), aromatic amino acids (phenylalanine, tryptophan and tyrosine), and small amino acids (glycine, alanine, serine, threonine and methionine). Amino acid substitutions that do not generally alter specific activity are known in the art and are described, for example, by H. Neurath and R. L. Hill, 1979, In, *The Proteins*, Academic Press, New York. Common substitutions are Ala/Ser, Val/Ile, Asp/Glu, Thr/Ser, Ala/Gly, Ala/Thr, Ser/Asn, Ala/Val, Ser/Gly, Tyr/Phe, Ala/Pro, Lys/Arg, Asp/Asn, Leu/Ile, Leu/Val, Ala/Glu, and Asp/Gly.

Alternatively, the amino acid changes are of such a nature that the physico-chemical properties of the polypeptides are altered. For example, amino acid changes may improve the thermal stability of the polypeptide, alter the substrate specificity, change the pH optimum, and the like.

Essential amino acids in a polypeptide can be identified according to procedures known in the art, such as site-directed mutagenesis or alanine-scanning mutagenesis (Cunningham and Wells, 1989, *Science* 244: 1081-1085). In the latter technique, single alanine mutations are introduced at every residue in the molecule, and the resultant mutant molecules are tested for beta-glucosidase activity, beta-xylosidase activity, or beta-glucosidase and beta-xylosidase activity to identify amino acid residues that are critical to the activity of the molecule. See also, Hilton et al., 1996, *J. Biol. Chem.* 271: 4699-4708. The active site of the enzyme or other biological interaction can also be determined by physical analysis of structure, as determined by such techniques as nuclear magnetic resonance, crystallography, electron diffraction, or photoaffinity labeling, in conjunction with mutation of putative contact site amino acids. See, for example, de Vos et al., 1992, *Science* 255: 306-312; Smith et al., 1992, *J. Mol. Biol.* 224: 899-904; Wlodaver et al., 1992, *FEBS Lett.* 309: 59-64. The identity of essential amino acids can also be inferred from an alignment with a related polypeptide.

Single or multiple amino acid substitutions, deletions, and/or insertions can be made and tested using known methods of mutagenesis, recombination, and/or shuffling, followed by a relevant screening procedure, such as those disclosed by Reidhaar-Olson and Sauer, 1988, *Science* 241: 53-57; Bowie and Sauer, 1989, *Proc. Natl. Acad. Sci. USA* 86: 2152-2156; WO 95/17413; or WO 95/22625. Other methods that can be used include error-prone PCR, phage display (e.g., Lowman et al., 1991, *Biochemistry* 30: 10832-10837; U.S. Pat. No. 5,223,409; WO 92/06204), and region-directed mutagenesis (Derbyshire et al., 1986, *Gene* 46: 145; Ner et al., 1988, *DNA* 7: 127).

Mutagenesis/shuffling methods can be combined with high-throughput, automated screening methods to detect activity of cloned, mutagenized polypeptides expressed by host cells (Ness et al., 1999, *Nature Biotechnology* 17: 893-896). Mutagenized DNA molecules that encode active polypeptides can be recovered from the host cells and rapidly sequenced using standard methods in the art. These methods allow the rapid determination of the importance of individual amino acid residues in a polypeptide.

The polypeptide may be a hybrid polypeptide in which a region of one polypeptide is fused at the N-terminus or the C-terminus of a region of another polypeptide.

The polypeptide may be a fusion polypeptide or cleavable fusion polypeptide in which another polypeptide is fused at the N-terminus or the C-terminus of the polypeptide of the present invention. A fusion polypeptide is produced by fusing a polynucleotide encoding another polypeptide to a polynucleotide of the present invention. Techniques for producing fusion polypeptides are known in the art, and include ligating the coding sequences encoding the polypeptides so that they are in frame and that expression of the fusion polypeptide is under control of the same promoter(s) and terminator. Fusion polypeptides may also be constructed using intein technology in which fusion polypeptides are created post-translationally (Cooper et al., 1993, *EMBO J.* 12: 2575-2583; Dawson et al., 1994, *Science* 266: 776-779).

A fusion polypeptide can further comprise a cleavage site between the two polypeptides. Upon secretion of the fusion protein, the site is cleaved releasing the two polypeptides. Examples of cleavage sites include, but are not limited to, the sites disclosed in Martin et al., 2003, *J. Ind. Microbiol. Biotechnol.* 3: 568-576; Svetina et al., 2000, *J. Biotechnol.* 76: 245-251; Rasmussen-Wilson et al., 1997, *Appl. Environ. Microbiol.* 63: 3488-3493; Ward et al., 1995, *Biotechnology* 13: 498-503; and Contreras et al., 1991, *Biotechnology* 9: 378-381; Eaton et al., 1986, *Biochemistry* 25: 505-512; Collins-Racie et al., 1995, *Biotechnology* 13: 982-987; Carter et al., 1989, *Proteins: Structure, Function, and Genetics* 6: 240-248; and Stevens, 2003, *Drug Discovery World* 4: 35-48.

Sources of Polypeptides Having Beta-Glucosidase Activity, Beta-Xylosidase Activity, or Beta-Glucosidase and Beta-Xylosidase Activity A polypeptide having beta-glucosidase activity, beta-xylosidase activity, or beta-glucosidase and beta-xylosidase activity of the present invention may be obtained from microorganisms of any genus. For purposes of the present invention, the term "obtained from" as used herein in connection with a given source shall mean that the polypeptide encoded by a polynucleotide is produced by the source or by a strain in which the polynucleotide from the source has been inserted. In one aspect, the polypeptide obtained from a given source is secreted extracellularly.

The polypeptide may be a fungal polypeptide. For example, the polypeptide may be a yeast polypeptide such as a *Candida*, *Kluyveromyces*, *Pichia*, *Saccharomyces*, *Schizosaccharomyces*, or *Yarrowia* polypeptide; or a filamentous fungal polypeptide such as an *Acremonium*, *Agaricus*, *Alternaria*, *Aspergillus*, *Aureobasidium*, *Botryospaeria*, *Ceriporiopsis*, *Chaetomidium*, *Chrysosporium*, *Claviceps*, *Cochliobolus*, *Coprinopsis*, *Coptotermes*, *Corynascus*, *Cryphonectria*, *Cryptococcus*, *Diplodia*, *Exidia*, *Filibasidium*, *Fusarium*, *Gibberella*, *Holomastigotoides*, *Humicola*, *Irpex*, *Lentinula*, *Leptospaeria*, *Magnaporthe*, *Melanocarpus*, *Meripilus*, *Mucor*, *Myceliophthora*, *Neocallimastix*, *Neurospora*, *Paecilomyces*, *Penicillium*, *Phanerochaete*, *Piromyces*, *Poitrasia*, *Pseudoplectania*, *Pseudotrichonympha*, *Rhizomucor*, *Schizophyllum*, *Scytalidium*, *Talaromyces*, *Thermoascus*, *Thielavia*, *Tolypocladium*, *Trichoderma*, *Trichophaea*, *Verticillium*, *Volvariella*, or *Xylaria* polypeptide.

In another aspect, the polypeptide is a *Saccharomyces carlsbergensis*, *Saccharomyces cerevisiae*, *Saccharomyces diastaticus*, *Saccharomyces douglasii*, *Saccharomyces kluyveri*, *Saccharomyces norbensis*, or *Saccharomyces oviformis* polypeptide.

In another aspect, the polypeptide is an *Acremonium cellulolyticus*, *Aspergillus aculeatus*, *Aspergillus awamori*, *Aspergillus foetidus*, *Aspergillus fumigatus*, *Aspergillus japonicus*, *Aspergillus nidulans*, *Aspergillus niger*, *Aspergillus oryzae*, *Chrysosporium inops*, *Chrysosporium keratinophilum*, *Chrysosporium lucknowense*, *Chrysosporium merdarium*, *Chrysosporium pannicola*, *Chrysosporium queenslandicum*, *Chrysosporium tropicum*, *Chrysosporium zonatum*, *Fusarium bactridioides*, *Fusarium cerealis*, *Fusarium crookwellense*, *Fusarium culmorum*, *Fusarium graminearum*, *Fusarium graminum*, *Fusarium heterosporum*, *Fusarium negundi*, *Fusarium oxysporum*, *Fusarium reticulatum*, *Fusarium roseum*, *Fusarium sambucinum*, *Fusarium sarcochroum*, *Fusarium sporotrichioides*, *Fusarium sulphureum*, *Fusarium torulosum*, *Fusarium trichothecioides*, *Fusarium venenatum*, *Humicola grisea*, *Humicola insolens*, *Humicola lanuginosa*, *Irpex lacteus*, *Mucor miehei*, *Myceliophthora thermophila*, *Neurospora crassa*, *Penicillium funiculosum*, *Penicillium purpurogenum*, *Phanerochaete chrysosporium*, *Thielavia achromatica*, *Thielavia albomyces*, *Thielavia albopilosa*, *Thielavia australeinsis*, *Thielavia fimeti*, *Thielavia microspora*, *Thielavia ovispora*, *Thielavia peruviana*, *Thielavia setosa*, *Thielavia spededonium*, *Thielavia subthermophila*, *Thielavia terrestris*, *Trichoderma harzianum*, *Trichoderma koningii*, *Trichoderma longibrachiatum*, *Trichoderma reesei*, or *Trichoderma viride* polypeptide.

In another aspect, the polypeptide is an *Aspergillus aculeatus* polypeptide, e.g., a polypeptide obtained from *Aspergillus aculeatus* CBS 172.66.

It will be understood that for the aforementioned species the invention encompasses both the perfect and imperfect states, and other taxonomic equivalents, e.g., anamorphs, regardless of the species name by which they are known. Those skilled in the art will readily recognize the identity of appropriate equivalents.

Strains of these species are readily accessible to the public in a number of culture collections, such as the American Type Culture Collection (ATCC), Deutsche Sammlung von Mikroorganismen and Zellkulturen GmbH (DSMZ), Centraalbureau Voor Schimmelcultures (CBS), and Agricultural Research Service Patent Culture Collection, Northern Regional Research Center (NRRL).

The polypeptide may be identified and obtained from other sources including microorganisms isolated from nature (e.g., soil, composts, water, etc.) or DNA samples obtained directly from natural materials (e.g., soil, composts, water, etc.) using the above-mentioned probes. Techniques for isolating microorganisms and DNA directly from natural habitats are well known in the art. A polynucleotide encoding the polypeptide may then be obtained by similarly screening a genomic DNA or cDNA library of another microorganism or mixed DNA sample. Once a polynucleotide encoding a polypeptide has been detected with the probe(s), the polynucleotide can be isolated or cloned by utilizing techniques that are known to those of ordinary skill in the art (see, e.g., Sambrook et al., 1989, supra).

Polynucleotides

The present invention also relates to isolated polynucleotides encoding a polypeptide of the present invention.

The techniques used to isolate or clone a polynucleotide encoding a polypeptide are known in the art and include isolation from genomic DNA or cDNA, or a combination thereof. The cloning of the polynucleotides from genomic DNA can be effected, e.g., by using the well known polymerase chain reaction (PCR) or antibody screening of expression libraries to detect cloned DNA fragments with shared structural features. See, e.g., Innis et al., 1990, *PCR: A Guide to Methods and Application*, Academic Press, New York. Other nucleic acid amplification procedures such as ligase chain reaction (LCR), ligation activated transcription (LAT) and polynucleotide-based amplification (NASBA) may be used. The polynucleotides may be cloned from a strain of *Aspergillus aculeatus*, or a related organism and thus, for example, may be an allelic or species variant of the polypeptide encoding region of the polynucleotide.

In another embodiment, the present invention relates to isolated polynucleotides comprising or consisting of polynucleotides having a degree of sequence identity to the mature polypeptide coding sequence of SEQ ID NO: 1 or the cDNA sequence thereof, or SEQ ID NO: 11 of at least 75%, e.g., at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100%; the mature polypeptide coding sequence of SEQ ID NO: 5 or the cDNA sequence thereof, SEQ ID NO: 7, or SEQ ID NO: 9 of at least 80%, e.g., at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100%; or the mature polypeptide coding sequence of SEQ ID NO: 3 or the cDNA sequence thereof of at least 85%, e.g., at least 86%, at least 87%, at least 88%, at least 89%, at least 90%, at least 91%, at least 92%, at least 93%, at least 94%, at least 95%, at least 96%, at least 97%, at least 98%, at least 99%, or 100%; which encode polypeptides having beta-glucosidase activity, beta-xylosidase activity, or beta-glucosidase and beta-xylosidase activity.

Modification of a polynucleotide encoding a polypeptide of the present invention may be necessary for synthesizing polypeptides substantially similar to the polypeptide. The term "substantially similar" to the polypeptide refers to non-naturally occurring forms of the polypeptide. These polypeptides may differ in some engineered way from the polypeptide isolated from its native source, e.g., variants that differ in specific activity, thermostability, pH optimum, or the like. The variants may be constructed on the basis of the polynucleotide presented as the mature polypeptide coding sequence of SEQ ID NO: 1 or the cDNA sequence thereof, SEQ ID NO: 3 or the cDNA sequence thereof, SEQ ID NO: 5 or the cDNA sequence thereof, SEQ ID NO: 7, SEQ ID NO: 9, or SEQ ID NO: 11, e.g., a subsequence thereof, and/or by introduction of nucleotide substitutions that do not result in a change in the amino acid sequence of the polypeptide, but which correspond to the codon usage of the host organism intended for production of the enzyme, or by introduction of nucleotide substitutions that may give rise to a different amino acid sequence. For a general description of nucleotide substitution, see, e.g., Ford et al., 1991, *Protein Expression and Purification* 2: 95-107.

In another embodiment, the present invention relates to isolated polynucleotides encoding polypeptides of the present invention, which hybridize under low stringency conditions, medium stringency conditions, medium-high stringency conditions, high stringency conditions, or very high stringency conditions with (i) the mature polypeptide coding sequence of SEQ ID NO: 1 or the cDNA sequence thereof, SEQ ID NO: 3 or the cDNA sequence thereof, SEQ ID NO: 5 or the cDNA sequence thereof, SEQ ID NO: 7, SEQ ID NO: 9, or SEQ ID NO: 11, or (ii) the full-length complement of (i); or allelic variants and subsequences thereof (Sambrook et al., 1989, supra), as defined herein.

In one aspect, the polynucleotide comprises or consists of SEQ ID NO: 1, SEQ ID NO: 3, SEQ ID NO: 5, SEQ ID NO: 7, SEQ ID NO: 9, or SEQ ID NO: 11; or the mature polypeptide coding sequence thereof; or a subsequence thereof that encodes a fragment having beta-glucosidase activity, beta-xylosidase activity, or beta-glucosidase and beta-xylosidase activity.

Nucleic Acid Constructs

The present invention also relates to nucleic acid constructs comprising a polynucleotide of the present invention operably linked to one or more control sequences that direct the expression of the coding sequence in a suitable host cell under conditions compatible with the control sequences.

A polynucleotide may be manipulated in a variety of ways to provide for expression of the polypeptide. Manipulation of the polynucleotide prior to its insertion into a vector may be desirable or necessary depending on the expression vector. The techniques for modifying polynucleotides utilizing recombinant DNA methods are well known in the art.

The control sequence may be a promoter, a polynucleotide that is recognized by a host cell for expression of a polynucleotide encoding a polypeptide of the present invention. The promoter contains transcriptional control sequences that mediate the expression of the polypeptide. The promoter may be any polynucleotide that shows transcriptional activity in the host cell including mutant, truncated, and hybrid promoters, and may be obtained from genes encoding extracellular or intracellular polypeptides either homologous or heterologous to the host cell.

Examples of suitable promoters for directing transcription of the nucleic acid constructs of the present invention in a bacterial host cell are the promoters obtained from the *Bacillus amyloliquefaciens* alpha-amylase gene (amyQ), *Bacillus licheniformis* alpha-amylase gene (amyL), *Bacillus licheniformis* penicillinase gene (penP), *Bacillus stearothermophilus* maltogenic amylase gene (amyM), *Bacillus subtilis* levansucrase gene (sacB), *Bacillus subtilis* xylA and xylB genes, *Bacillus thuringiensis* cryIIIA gene (Agaisse and Lereclus, 1994, *Molecular Microbiology* 13: 97-107), *E. coli* lac operon, *E. coli* trc promoter (Egon et al., 1988, *Gene* 69: 301-315), *Streptomyces coelicolor* agarase gene (dagA), and prokaryotic beta-lactamase gene (VIIIa-Kamaroff et al., 1978, *Proc. Natl. Acad. Sci. USA* 75: 3727-3731), as well as the tac promoter (DeBoer et al., 1983, *Proc. Natl. Acad. Sci. USA* 80: 21-25). Further promoters are described in "Useful proteins from recombinant bacteria" in Gilbert et al., 1980, *Scientific American* 242: 74-94; and in Sambrook et al., 1989, supra. Examples of tandem promoters are disclosed in WO 99/43835.

Examples of suitable promoters for directing transcription of the nucleic acid constructs of the present invention in a filamentous fungal host cell are promoters obtained from the genes for *Aspergillus nidulans* acetamidase, *Aspergillus niger* neutral alpha-amylase, *Aspergillus niger* acid stable alpha-amylase, *Aspergillus niger* or *Aspergillus awamori* glucoamylase (glaA), *Aspergillus oryzae* TAKA amylase, *Aspergillus oryzae* alkaline protease, *Aspergillus oryzae* triose phosphate isomerase, *Fusarium oxysporum* trypsin-like protease (WO 96/00787), *Fusarium venenatum* amyloglucosidase (WO 00/56900), *Fusarium venenatum* Dania (WO 00/56900), *Fusarium venenatum* Quinn (WO 00/56900), *Rhizomucor miehei* lipase, *Rhizomucor miehei* aspartic proteinase, *Trichoderma reesei* beta-glucosidase, *Trichoderma reesei* cellobiohydrolase I, *Trichoderma reesei* cellobiohydrolase II, *Trichoderma reesei* endoglucanase I, *Trichoderma reesei* endoglucanase II, *Trichoderma reesei* endoglucanase III, *Trichoderma reesei* endoglucanase V, *Trichoderma reesei* xylanase I, *Trichoderma reesei* xylanase II, *Trichoderma reesei* xylanase III, *Trichoderma reesei* beta-xylosidase, and *Trichoderma reesei* translation elongation factor, as well as the NA2-tpi promoter (a modified promoter from an *Aspergillus neutral* alpha-amylase gene in which the untranslated leader has been replaced by an untranslated leader from an *Aspergillus* triose phosphate isomerase gene; non-limiting examples include modified promoters from an *Aspergillus niger* neutral alpha-amylase gene in which the untranslated leader has been replaced by an untranslated leader from an *Aspergillus nidulans* or *Aspergillus oryzae* triose phosphate isomerase gene); and mutant, truncated, and hybrid promoters thereof. Other promoters are described in U.S. Pat. No. 6,011,147.

In a yeast host, useful promoters are obtained from the genes for *Saccharomyces cerevisiae* enolase (ENO-1), *Saccharomyces cerevisiae* galactokinase (GAL1), *Saccharomyces cerevisiae* alcohol dehydrogenase/glyceraldehyde-3-phosphate dehydrogenase (ADH1, ADH2/GAP), *Saccharomyces cerevisiae* triose phosphate isomerase (TPI), *Saccharomyces cerevisiae* metallothionein (CUP1), and *Saccharomyces cerevisiae* 3-phosphoglycerate kinase. Other useful promoters for yeast host cells are described by Romanos et al., 1992, *Yeast* 8: 423-488.

The control sequence may also be a transcription terminator, which is recognized by a host cell to terminate transcription. The terminator is operably linked to the 3'-terminus of the polynucleotide encoding the polypeptide. Any terminator that is functional in the host cell may be used in the present invention.

Preferred terminators for bacterial host cells are obtained from the genes for *Bacillus clausii* alkaline protease (aprH), *Bacillus licheniformis* alpha-amylase (amyL), and *Escherichia coli* ribosomal RNA (rrnB).

Preferred terminators for filamentous fungal host cells are obtained from the genes for *Aspergillus nidulans* acetamidase, *Aspergillus nidulans* anthranilate synthase, *Aspergillus niger* glucoamylase, *Aspergillus niger* alpha-glucosidase, *Aspergillus oryzae* TAKA amylase, *Fusarium oxysporum* trypsin-like protease, *Trichoderma reesei* beta-glucosidase, *Trichoderma reesei* cellobiohydrolase I, *Trichoderma reesei* cellobiohydrolase II, *Trichoderma reesei* endoglucanase I, *Trichoderma reesei* endoglucanase II, *Trichoderma reesei* endoglucanase III, *Trichoderma reesei* endoglucanase V, *Trichoderma reesei* xylanase I, *Trichoderma reesei* xylanase II, *Trichoderma reesei* xylanase III, *Trichoderma reesei* beta-xylosidase, and *Trichoderma reesei* translation elongation factor.

Preferred terminators for yeast host cells are obtained from the genes for *Saccharomyces cerevisiae* enolase, *Saccharomyces cerevisiae* cytochrome C (CYC1), and *Saccharomyces cerevisiae* glyceraldehyde-3-phosphate dehydrogenase. Other useful terminators for yeast host cells are described by Romanos et al., 1992, supra.

The control sequence may also be an mRNA stabilizer region downstream of a promoter and upstream of the coding sequence of a gene which increases expression of the gene.

Examples of suitable mRNA stabilizer regions are obtained from a *Bacillus thuringiensis* cryIIIA gene (WO 94/25612) and a *Bacillus subtilis* SP82 gene (Hue et al., 1995, *Journal of Bacteriology* 177: 3465-3471).

The control sequence may also be a leader, a nontranslated region of an mRNA that is important for translation by the host cell. The leader is operably linked to the 5'-terminus of the polynucleotide encoding the polypeptide. Any leader that is functional in the host cell may be used.

Preferred leaders for filamentous fungal host cells are obtained from the genes for *Aspergillus oryzae* TAKA amylase and *Aspergillus nidulans* triose phosphate isomerase.

Suitable leaders for yeast host cells are obtained from the genes for *Saccharomyces cerevisiae* enolase (ENO-1), *Saccharomyces cerevisiae* 3-phosphoglycerate kinase, *Saccharomyces cerevisiae* alpha-factor, and *Saccharomyces cerevisiae* alcohol dehydrogenase/glyceraldehyde-3-phosphate dehydrogenase (ADH2/GAP).

The control sequence may also be a polyadenylation sequence, a sequence operably linked to the 3'-terminus of the polynucleotide and, when transcribed, is recognized by the host cell as a signal to add polyadenosine residues to transcribed mRNA. Any polyadenylation sequence that is functional in the host cell may be used.

Preferred polyadenylation sequences for filamentous fungal host cells are obtained from the genes for *Aspergillus nidulans* anthranilate synthase, *Aspergillus niger* glucoamylase, *Aspergillus niger* alpha-glucosidase *Aspergillus oryzae* TAKA amylase, and *Fusarium oxysporum* trypsin-like protease.

Useful polyadenylation sequences for yeast host cells are described by Guo and Sherman, 1995, *Mol. Cellular. Biol.* 15: 5983-5990.

The control sequence may also be a signal peptide coding region that encodes a signal peptide linked to the N-terminus of a polypeptide and directs the polypeptide into the cell's secretory pathway. The 5'-end of the coding sequence of the polynucleotide may inherently contain a signal peptide coding sequence naturally linked in translation reading frame with the segment of the coding sequence that encodes the polypeptide. Alternatively, the 5'-end of the coding sequence may contain a signal peptide coding sequence that is foreign to the coding sequence. A foreign signal peptide coding sequence may be required where the coding sequence does not naturally contain a signal peptide coding sequence.

Alternatively, a foreign signal peptide coding sequence may simply replace the natural signal peptide coding sequence in order to enhance secretion of the polypeptide. However, any signal peptide coding sequence that directs the expressed polypeptide into the secretory pathway of a host cell may be used.

Effective signal peptide coding sequences for bacterial host cells are the signal peptide coding sequences obtained from the genes for *Bacillus* NCIB 11837 maltogenic amylase, *Bacillus licheniformis* subtilisin, *Bacillus licheniformis* beta-lactamase, *Bacillus stearothermophilus* alpha-amylase, *Bacillus stearothermophilus* neutral proteases (nprT, nprS, nprM), and *Bacillus subtilis* prsA. Further signal peptides are described by Simonen and Palva, 1993, *Microbiological Reviews* 57: 109-137.

Effective signal peptide coding sequences for filamentous fungal host cells are the signal peptide coding sequences obtained from the genes for *Aspergillus niger* neutral amylase, *Aspergillus niger* glucoamylase, *Aspergillus oryzae* TAKA amylase, *Humicola insolens* cellulase, *Humicola insolens* endoglucanase V, *Humicola lanuginosa* lipase, and *Rhizomucor miehei* aspartic proteinase.

Useful signal peptides for yeast host cells are obtained from the genes for *Saccharomyces cerevisiae* alpha-factor and *Saccharomyces cerevisiae* invertase. Other useful signal peptide coding sequences are described by Romanos et al., 1992, supra.

The control sequence may also be a propeptide coding sequence that encodes a propeptide positioned at the N-terminus of a polypeptide. The resultant polypeptide is known as a proenzyme or propolypeptide (or a zymogen in some cases). A propolypeptide is generally inactive and can be converted to an active polypeptide by catalytic or autocatalytic cleavage of the propeptide from the propolypeptide. The propeptide coding sequence may be obtained from the genes for *Bacillus subtilis* alkaline protease (aprE), *Bacillus subtilis* neutral protease (nprT), *Myceliophthora thermophila* laccase (WO 95/33836), *Rhizomucor miehei* aspartic proteinase, and *Saccharomyces cerevisiae* alpha-factor.

Where both signal peptide and propeptide sequences are present, the propeptide sequence is positioned next to the N-terminus of a polypeptide and the signal peptide sequence is positioned next to the N-terminus of the propeptide sequence.

It may also be desirable to add regulatory sequences that regulate expression of the polypeptide relative to the growth of the host cell. Examples of regulatory sequences are those that cause expression of the gene to be turned on or off in response to a chemical or physical stimulus, including the presence of a regulatory compound. Regulatory sequences in prokaryotic systems include the lac, tac, and trp operator systems. In yeast, the ADH2 system or GAL1 system may be used. In filamentous fungi, the *Aspergillus niger* glucoamylase promoter, *Aspergillus oryzae* TAKA alpha-amylase promoter, and *Aspergillus oryzae* glucoamylase promoter, *Trichoderma reesei* cellobiohydrolase I promoter, and *Trichoderma reesei* cellobiohydrolase II promoter may be used. Other examples of regulatory sequences are those that allow for gene amplification. In eukaryotic systems, these regulatory sequences include the dihydrofolate reductase gene that is amplified in the presence of methotrexate, and the metallothionein genes that are amplified with heavy metals. In these cases, the polynucleotide encoding the polypeptide would be operably linked to the regulatory sequence.

Expression Vectors

The present invention also relates to recombinant expression vectors comprising a polynucleotide of the present invention, a promoter, and transcriptional and translational stop signals. The various nucleotide and control sequences may be joined together to produce a recombinant expression vector that may include one or more convenient restriction sites to allow for insertion or substitution of the polynucleotide encoding the polypeptide at such sites. Alternatively, the polynucleotide may be expressed by inserting the polynucleotide or a nucleic acid construct comprising the polynucleotide into an appropriate vector for expression. In creating the expression vector, the coding sequence is located in the vector so that the coding sequence is operably linked with the appropriate control sequences for expression.

The recombinant expression vector may be any vector (e.g., a plasmid or virus) that can be conveniently subjected to recombinant DNA procedures and can bring about expression of the polynucleotide. The choice of the vector will typically depend on the compatibility of the vector with the host cell into which the vector is to be introduced. The vector may be a linear or closed circular plasmid.

The vector may be an autonomously replicating vector, i.e., a vector that exists as an extrachromosomal entity, the replication of which is independent of chromosomal replication, e.g., a plasmid, an extrachromosomal element, a minichromosome, or an artificial chromosome. The vector may contain any means for assuring self-replication. Alternatively, the vector may be one that, when introduced into the host cell, is integrated into the genome and replicated together with the chromosome(s) into which it has been integrated. Furthermore, a single vector or plasmid or two or more vectors or plasmids that together contain the total DNA to be introduced into the genome of the host cell, or a transposon, may be used.

The vector preferably contains one or more selectable markers that permit easy selection of transformed, transfected, transduced, or the like cells. A selectable marker is a gene the product of which provides for biocide or viral resistance, resistance to heavy metals, prototrophy to auxotrophs, and the like.

Examples of bacterial selectable markers are *Bacillus licheniformis* or *Bacillus subtilis* dal genes, or markers that confer antibiotic resistance such as ampicillin, chloramphenicol, kanamycin, neomycin, spectinomycin, or tetracycline resistance. Suitable markers for yeast host cells include, but are not limited to, ADE2, HIS3, LEU2, LYS2, MET3, TRP1, and URA3. Selectable markers for use in a filamentous fungal host cell include, but are not limited to, adeA (phosphoribosylaminoimidazole-succinocarboxamide synthase), adeB (phospho-ribosylaminoimidazole synthase), amdS (acetamidase), argB (ornithine carbamoyltransferase), bar (phosphinothricin acetyltransferase), hph (hygromycin phosphotransferase), niaD (nitrate reductase), pyrG (orotidine-5'-phosphate decarboxylase), sC (sulfate adenyltransferase), and trpC (anthranilate synthase), as well as equivalents thereof. Preferred for use in an *Aspergillus* cell are *Aspergillus nidulans* or *Aspergillus oryzae* amdS and pyrG genes and a *Streptomyces hygroscopicus* bar gene. Preferred for use in a *Trichoderma* cell are adeA, adeB, amdS, hph, and pyrG genes.

The selectable marker may be a dual selectable marker system as described in WO 2010/039889. In one aspect, the dual selectable marker is a hph-tk dual selectable marker system.

The vector preferably contains an element(s) that permits integration of the vector into the host cell's genome or autonomous replication of the vector in the cell independent of the genome.

For integration into the host cell genome, the vector may rely on the polynucleotide's sequence encoding the polypeptide or any other element of the vector for integration into the genome by homologous or non-homologous recombination. Alternatively, the vector may contain additional polynucleotides for directing integration by homologous recombination into the genome of the host cell at a precise location(s) in the chromosome(s). To increase the likelihood of integration at a precise location, the integrational elements should contain a sufficient number of nucleic acids, such as 100 to 10,000 base pairs, 400 to 10,000 base pairs, and 800 to 10,000 base pairs, which have a high degree of sequence identity to the corresponding target sequence to enhance the probability of homologous recombination. The integrational elements may be any sequence that is homologous with the target sequence in the genome of the host cell. Furthermore, the integrational elements may be non-encoding or encoding polynucleotides. On the other hand, the vector may be integrated into the genome of the host cell by non-homologous recombination.

For autonomous replication, the vector may further comprise an origin of replication enabling the vector to replicate autonomously in the host cell in question. The origin of replication may be any plasmid replicator mediating autonomous replication that functions in a cell. The term "origin of replication" or "plasmid replicator" means a polynucleotide that enables a plasmid or vector to replicate in vivo.

Examples of bacterial origins of replication are the origins of replication of plasmids pBR322, pUC19, pACYC177, and pACYC184 permitting replication in *E. coli*, and pUB110, pE194, pTA1060, and pAMR1 permitting replication in *Bacillus*.

Examples of origins of replication for use in a yeast host cell are the 2 micron origin of replication, ARS1, ARS4, the combination of ARS1 and CEN3, and the combination of ARS4 and CEN6.

Examples of origins of replication useful in a filamentous fungal cell are AMA1 and ANSI (Gems et al., 1991, *Gene* 98: 61-67; Cullen et al., 1987, *Nucleic Acids Res.* 15: 9163-9175; WO 00/24883). Isolation of the AMA1 gene and construction of plasmids or vectors comprising the gene can be accomplished according to the methods disclosed in WO 00/24883.

More than one copy of a polynucleotide of the present invention may be inserted into a host cell to increase production of a polypeptide. An increase in the copy number of the polynucleotide can be obtained by integrating at least one additional copy of the sequence into the host cell genome or by including an amplifiable selectable marker gene with the polynucleotide where cells containing amplified copies of the selectable marker gene, and thereby additional copies of the polynucleotide, can be selected for by cultivating the cells in the presence of the appropriate selectable agent.

The procedures used to ligate the elements described above to construct the recombinant expression vectors of the present invention are well known to one skilled in the art (see, e.g., Sambrook et al., 1989, supra).

Host Cells

The present invention also relates to recombinant host cells, comprising a polynucleotide of the present invention operably linked to one or more control sequences that direct the production of a polypeptide of the present invention. A construct or vector comprising a polynucleotide is introduced into a host cell so that the construct or vector is maintained as a chromosomal integrant or as a self-replicating extra-chromosomal vector as described earlier. The term "host cell" encompasses any progeny of a parent cell that is not identical to the parent cell due to mutations that occur during replication. The choice of a host cell will to a large extent depend upon the gene encoding the polypeptide and its source.

The host cell may be any cell useful in the recombinant production of a polypeptide of the present invention, e.g., a prokaryote or a eukaryote.

The prokaryotic host cell may be any Gram-positive or Gram-negative bacterium. Gram-positive bacteria include, but are not limited to, Bacillus, Clostridium, Enterococcus, Geobacillus, Lactobacillus, Lactococcus, Oceanobacillus, Staphylococcus, Streptococcus, and Streptomyces. Gram-negative bacteria include, but are not limited to, Campylobacter, E. coli, Flavobacterium, Fusobacterium, Helicobacter, Ilyobacter, Neisseria, Pseudomonas, Salmonella, and Ureaplasma.

The bacterial host cell may be any Bacillus cell including, but not limited to, Bacillus alkalophilus, Bacillus amyloliquefaciens, Bacillus brevis, Bacillus circulans, Bacillus clausii, Bacillus coagulans, Bacillus firmus, Bacillus lautus, Bacillus lentus, Bacillus licheniformis, Bacillus megaterium, Bacillus pumilus, Bacillus stearothermophilus, Bacillus subtilis, and Bacillus thuringiensis cells.

The bacterial host cell may also be any Streptococcus cell including, but not limited to, Streptococcus equisimilis, Streptococcus pyogenes, Streptococcus uberis, and Streptococcus equi subsp. Zooepidemicus cells.

The bacterial host cell may also be any Streptomyces cell including, but not limited to, Streptomyces achromogenes, Streptomyces avermitilis, Streptomyces coelicolor, Streptomyces griseus, and Streptomyces lividans cells.

The introduction of DNA into a Bacillus cell may be effected by protoplast transformation (see, e.g., Chang and Cohen, 1979, Mol. Gen. Genet. 168: 111-115), competent cell transformation (see, e.g., Young and Spizizen, 1961, J. Bacteriol. 81: 823-829, or Dubnau and Davidoff-Abelson, 1971, J. Mol. Biol. 56: 209-221), electroporation (see, e.g., Shigekawa and Dower, 1988, Biotechniques 6: 742-751), or conjugation (see, e.g., Koehler and Thorne, 1987, J. Bacteriol. 169: 5271-5278). The introduction of DNA into an E. coli cell may be effected by protoplast transformation (see, e.g., Hanahan, 1983, J. Mol. Biol. 166: 557-580) or electroporation (see, e.g., Dower et al., 1988, Nucleic Acids Res. 16: 6127-6145). The introduction of DNA into a Streptomyces cell may be effected by protoplast transformation, electroporation (see, e.g., Gong et al., 2004, Folia Microbiol. (Praha) 49: 399-405), conjugation (see, e.g., Mazodier et al., 1989, J. Bacteriol. 171: 3583-3585), or transduction (see, e.g., Burke et al., 2001, Proc. Natl. Acad. Sci. USA 98: 6289-6294). The introduction of DNA into a Pseudomonas cell may be effected by electroporation (see, e.g., Choi et al., 2006, J. Microbiol. Methods 64: 391-397) or conjugation (see, e.g., Pinedo and Smets, 2005, Appl. Environ. Microbiol. 71: 51-57). The introduction of DNA into a Streptococcus cell may be effected by natural competence (see, e.g., Perry and Kuramitsu, 1981, Infect. Immun. 32: 1295-1297), protoplast transformation (see, e.g., Catt and Jollick, 1991, Microbios 68: 189-207), electroporation (see, e.g., Buckley et al., 1999, Appl. Environ. Microbiol. 65: 3800-3804), or conjugation (see, e.g., Clewell, 1981, Microbiol. Rev. 45: 409-436). However, any method known in the art for introducing DNA into a host cell can be used.

The host cell may also be a eukaryote, such as a mammalian, insect, plant, or fungal cell.

The host cell may be a fungal cell. "Fungi" as used herein includes the phyla Ascomycota, Basidiomycota, Chytridiomycota, and Zygomycota as well as the Oomycota and all mitosporic fungi (as defined by Hawksworth et al., In, Ainsworth and Bisby's Dictionary of The Fungi, 8th edition, 1995, CAB International, University Press, Cambridge, UK).

The fungal host cell may be a yeast cell. "Yeast" as used herein includes ascosporogenous yeast (Endomycetales), basidiosporogenous yeast, and yeast belonging to the Fungi Imperfecti (Blastomycetes). Since the classification of yeast may change in the future, for the purposes of this invention, yeast shall be defined as described in Biology and Activities of Yeast (Skinner, Passmore, and Davenport, editors, Soc. App. Bacteriol. Symposium Series No. 9, 1980).

The yeast host cell may be a Candida, Hansenula, Kluyveromyces, Pichia, Saccharomyces, Schizosaccharomyces, or Yarrowia cell, such as a Kluyveromyces lactis, Saccharomyces carlsbergensis, Saccharomyces cerevisiae, Saccharomyces diastaticus, Saccharomyces douglasii, Saccharomyces kluyveri, Saccharomyces norbensis, Saccharomyces oviformis, or Yarrowia lipolytica cell.

The fungal host cell may be a filamentous fungal cell. "Filamentous fungi" include all filamentous forms of the subdivision Eumycota and Oomycota (as defined by Hawksworth et al., 1995, supra). The filamentous fungi are generally characterized by a mycelial wall composed of chitin, cellulose, glucan, chitosan, mannan, and other complex polysaccharides. Vegetative growth is by hyphal elongation and carbon catabolism is obligately aerobic. In contrast, vegetative growth by yeasts such as Saccharomyces cerevisiae is by budding of a unicellular thallus and carbon catabolism may be fermentative.

The filamentous fungal host cell may be an Acremonium, Aspergillus, Aureobasidium, Bjerkandera, Ceriporiopsis, Chrysosporium, Coprinus, Coriolus, Cryptococcus, Filibasidium, Fusarium, Humicola, Magnaporthe, Mucor, Myceliophthora, Neocallimastix, Neurospora, Paecilomyces, Penicillium, Phanerochaete, Phlebia, Piromyces, Pleurotus, Schizophyllum, Talaromyces, Thermoascus, Thielavia, Tolypocladium, Trametes, or Trichoderma cell.

For example, the filamentous fungal host cell may be an Aspergillus awamori, Aspergillus foetidus, Aspergillus fumigatus, Aspergillus japonicus, Aspergillus nidulans, Aspergillus niger, Aspergillus oryzae, Bjerkandera adusta, Ceriporiopsis aneirina, Ceriporiopsis caregiea, Ceriporiopsis gilvescens, Ceriporiopsis pannocinta, Ceriporiopsis rivulosa, Ceriporiopsis subrufa, Ceriporiopsis subvermispora,

*Chrysosporium inops, Chrysosporium keratinophilum, Chrysosporium lucknowense, Chrysosporium merdarium, Chrysosporium pannicola, Chrysosporium queenslandicum, Chrysosporium tropicum, Chrysosporium zonatum, Coprinus cinereus, Coriolus hirsutus, Fusarium bactridioides, Fusarium cerealis, Fusarium crookwellense, Fusarium culmorum, Fusarium graminearum, Fusarium graminum, Fusarium heterosporum, Fusarium negundi, Fusarium oxysporum, Fusarium reticulatum, Fusarium roseum, Fusarium sambucinum, Fusarium sarcochroum, Fusarium sporotrichioides, Fusarium sulphureum, Fusarium torulosum, Fusarium trichothecioides, Fusarium venenatum, Humicola insolens, Humicola lanuginosa, Mucor miehei, Myceliophthora thermophila, Neurospora crassa, Penicillium purpurogenum, Phanerochaete chrysosporium, Phlebia radiata, Pleurotus eryngii, Thielavia terrestris, Trametes villosa, Trametes versicolor, Trichoderma harzianum, Trichoderma koningii, Trichoderma longibrachiatum, Trichoderma reesei*, or *Trichoderma viride* cell.

Fungal cells may be transformed by a process involving protoplast formation, transformation of the protoplasts, and regeneration of the cell wall in a manner known per se. Suitable procedures for transformation of *Aspergillus* and *Trichoderma* host cells are described in EP 238023, Yelton et al., 1984, *Proc. Natl. Acad. Sci. USA* 81: 1470-1474, and Christensen et al., 1988, *Bio/Technology* 6: 1419-1422. Suitable methods for transforming *Fusarium* species are described by Malardier et al., 1989, *Gene* 78: 147-156, and WO 96/00787. Yeast may be transformed using the procedures described by Becker and Guarente, In Abelson, J. N. and Simon, M. I., editors, *Guide to Yeast Genetics and Molecular Biology, Methods in Enzymology*, Volume 194, pp 182-187, Academic Press, Inc., New York; Ito et al., 1983, *J. Bacteriol.* 153: 163; and Hinnen et al., 1978, *Proc. Natl. Acad. Sci. USA* 75: 1920.

Methods of Production

The present invention also relates to methods of producing a polypeptide of the present invention, comprising: (a) cultivating a cell, which in its wild-type form produces the polypeptide, under conditions conducive for production of the polypeptide; and (b) recovering the polypeptide. In one aspect, the cell is of the genus *Aspergillus*. In another aspect, the cell is *Aspergillus* aculeatus. In another aspect, the cell is *Aspergillus aculeatus* CBS 172.66.

The present invention also relates to methods of producing a polypeptide of the present invention, comprising: (a) cultivating a recombinant host cell of the present invention under conditions conducive for production of the polypeptide; and (b) recovering the polypeptide.

The cells are cultivated in a nutrient medium suitable for production of the polypeptide using methods known in the art. For example, the cells may be cultivated by shake flask cultivation, or small-scale or large-scale fermentation (including continuous, batch, fed-batch, or solid state fermentations) in laboratory or industrial fermentors in a suitable medium and under conditions allowing the polypeptide to be expressed and/or isolated. The cultivation takes place in a suitable nutrient medium comprising carbon and nitrogen sources and inorganic salts, using procedures known in the art. Suitable media are available from commercial suppliers or may be prepared according to published compositions (e.g., in catalogues of the American Type Culture Collection). If the polypeptide is secreted into the nutrient medium, the polypeptide can be recovered directly from the medium. If the polypeptide is not secreted, it can be recovered from cell lysates.

The polypeptide may be detected using methods known in the art that are specific for the polypeptides. These detection methods include, but are not limited to, use of specific antibodies, formation of an enzyme product, or disappearance of an enzyme substrate. For example, an enzyme assay may be used to determine the activity of the polypeptide.

The polypeptide may be recovered using methods known in the art. For example, the polypeptide may be recovered from the nutrient medium by conventional procedures including, but not limited to, collection, centrifugation, filtration, extraction, spray-drying, evaporation, or precipitation. In one aspect, the whole fermentation broth is recovered.

The polypeptide may be purified by a variety of procedures known in the art including, but not limited to, chromatography (e.g., ion exchange, affinity, hydrophobic, chromatofocusing, and size exclusion), electrophoretic procedures (e.g., preparative isoelectric focusing), differential solubility (e.g., ammonium sulfate precipitation), SDS-PAGE, or extraction (see, e.g., *Protein Purification*, Janson and Ryden, editors, VCH Publishers, New York, 1989) to obtain substantially pure polypeptides.

Plants

The present invention also relates to isolated plants, e.g., a transgenic plant, plant part, or plant cell, comprising a polynucleotide of the present invention so as to express and produce a polypeptide in recoverable quantities. The polypeptide may be recovered from the plant or plant part. Alternatively, the plant or plant part containing the polypeptide may be used as such for improving the quality of a food or feed, e.g., improving nutritional value, palatability, and rheological properties, or to destroy an antinutritive factor.

The transgenic plant can be dicotyledonous (a dicot) or monocotyledonous (a monocot). Examples of monocot plants are grasses, such as meadow grass (blue grass, Poa), forage grass such as Festuca, Lolium, temperate grass, such as Agrostis, and cereals, e.g., wheat, oats, rye, barley, rice, sorghum, and maize (corn).

Examples of dicot plants are tobacco, legumes, such as lupins, potato, sugar beet, pea, bean and soybean, and cruciferous plants (family Brassicaceae), such as cauliflower, rape seed, and the closely related model organism *Arabidopsis thaliana*.

Examples of plant parts are stem, callus, leaves, root, fruits, seeds, and tubers as well as the individual tissues comprising these parts, e.g., epidermis, mesophyll, parenchyme, vascular tissues, meristems. Specific plant cell compartments, such as chloroplasts, apoplasts, mitochondria, vacuoles, peroxisomes and cytoplasm are also considered to be a plant part. Furthermore, any plant cell, whatever the tissue origin, is considered to be a plant part. Likewise, plant parts such as specific tissues and cells isolated to facilitate the utilization of the invention are also considered plant parts, e.g., embryos, endosperms, aleurone and seed coats.

Also included within the scope of the present invention are the progeny of such plants, plant parts, and plant cells.

The transgenic plant or plant cell expressing the polypeptide may be constructed in accordance with methods known in the art. In short, the plant or plant cell is constructed by incorporating one or more expression constructs encoding the polypeptide into the plant host genome or chloroplast genome and propagating the resulting modified plant or plant cell into a transgenic plant or plant cell.

The expression construct is conveniently a nucleic acid construct that comprises a polynucleotide encoding a polypeptide operably linked with appropriate regulatory sequences required for expression of the polynucleotide in the plant or plant part of choice. Furthermore, the expression construct may comprise a selectable marker useful for identifying plant cells into which the expression construct has been integrated and DNA sequences necessary for introduction of the construct into the plant in question (the latter depends on the DNA introduction method to be used).

The choice of regulatory sequences, such as promoter and terminator sequences and optionally signal or transit sequences, is determined, for example, on the basis of when, where, and how the polypeptide is desired to be expressed. For instance, the expression of the gene encoding a polypeptide may be constitutive or inducible, or may be developmental, stage or tissue specific, and the gene product may be targeted to a specific tissue or plant part such as seeds or leaves. Regulatory sequences are, for example, described by Tague et al., 1988, *Plant Physiology* 86: 506.

For constitutive expression, the 35S-CaMV, the maize ubiquitin 1, or the rice actin 1 promoter may be used (Franck et al., 1980, *Cell* 21: 285-294; Christensen et al., 1992, *Plant Mol. Biol.* 18: 675-689; Zhang et al., 1991, *Plant Cell* 3: 1155-1165). Organ-specific promoters may be, for example, a promoter from storage sink tissues such as seeds, potato tubers, and fruits (Edwards and Coruzzi, 1990, *Ann. Rev. Genet.* 24: 275-303), or from metabolic sink tissues such as meristems (Ito et al., 1994, *Plant Mol. Biol.* 24: 863-878), a seed specific promoter such as the glutelin, prolamin, globulin, or albumin promoter from rice (Wu et al., 1998, *Plant Cell Physiol.* 39: 885-889), a *Vicia faba* promoter from the legumin B4 and the unknown seed protein gene from *Vicia faba* (Conrad et al., 1998, *J. Plant Physiol.* 152: 708-711), a promoter from a seed oil body protein (Chen et al., 1998, *Plant Cell Physiol.* 39: 935-941), the storage protein napA promoter from *Brassica napus*, or any other seed specific promoter known in the art, e.g., as described in WO 91/14772. Furthermore, the promoter may be a leaf specific promoter such as the rbcs promoter from rice or tomato (Kyozuka et al., 1993, *Plant Physiol.* 102: 991-1000), the chlorella virus adenine methyltransferase gene promoter (Mitra and Higgins, 1994, *Plant Mol. Biol.* 26: 85-93), the aldP gene promoter from rice (Kagaya et al., 1995, *Mol. Gen. Genet.* 248: 668-674), or a wound inducible promoter such as the potato pin2 promoter (Xu et al., 1993, *Plant Mol. Biol.* 22: 573-588). Likewise, the promoter may be induced by abiotic treatments such as temperature, drought, or alterations in salinity or induced by exogenously applied substances that activate the promoter, e.g., ethanol, oestrogens, plant hormones such as ethylene, abscisic acid, and gibberellic acid, and heavy metals.

A promoter enhancer element may also be used to achieve higher expression of a polypeptide in the plant. For instance, the promoter enhancer element may be an intron that is placed between the promoter and the polynucleotide encoding a polypeptide or domain. For instance, Xu et al., 1993, supra, disclose the use of the first intron of the rice actin 1 gene to enhance expression.

The selectable marker gene and any other parts of the expression construct may be chosen from those available in the art.

The nucleic acid construct is incorporated into the plant genome according to conventional techniques known in the art, including *Agrobacterium*-mediated transformation, virus-mediated transformation, microinjection, particle bombardment, biolistic transformation, and electroporation (Gasser et al., 1990, *Science* 244: 1293; Potrykus, 1990, *Bio/Technology* 8: 535; Shimamoto et al., 1989, *Nature* 338: 274).

*Agrobacterium tumefaciens*-mediated gene transfer is a method for generating transgenic dicots (for a review, see Hooykas and Schilperoort, 1992, *Plant Mol. Biol.* 19: 15-38) and for transforming monocots, although other transformation methods may be used for these plants. A method for generating transgenic monocots is particle bombardment (microscopic gold or tungsten particles coated with the transforming DNA) of embryonic calli or developing embryos (Christou, 1992, *Plant J.* 2: 275-281; Shimamoto, 1994, *Curr. Opin. Biotechnol.* 5: 158-162; Vasil et al., 1992, *Bio/Technology* 10: 667-674). An alternative method for transformation of monocots is based on protoplast transformation as described by Omirulleh et al., 1993, *Plant Mol. Biol.* 21: 415-428. Additional transformation methods include those described in U.S. Pat. Nos. 6,395,966 and 7,151,204 (both of which are herein incorporated by reference in their entirety).

Following transformation, the transformants having incorporated the expression construct are selected and regenerated into whole plants according to methods well known in the art. Often the transformation procedure is designed for the selective elimination of selection genes either during regeneration or in the following generations by using, for example, co-transformation with two separate T-DNA constructs or site specific excision of the selection gene by a specific recombinase.

In addition to direct transformation of a particular plant genotype with a construct of the present invention, transgenic plants may be made by crossing a plant having the construct to a second plant lacking the construct. For example, a construct encoding a polypeptide can be introduced into a particular plant variety by crossing, without the need for ever directly transforming a plant of that given variety. Therefore, the present invention encompasses not only a plant directly regenerated from cells which have been transformed in accordance with the present invention, but also the progeny of such plants. As used herein, progeny may refer to the offspring of any generation of a parent plant prepared in accordance with the present invention. Such progeny may include a DNA construct prepared in accordance with the present invention. Crossing results in the introduction of a transgene into a plant line by cross pollinating a starting line with a donor plant line. Non-limiting examples of such steps are described in U.S. Pat. No. 7,151,204.

Plants may be generated through a process of backcross conversion. For example, plants include plants referred to as a backcross converted genotype, line, inbred, or hybrid.

Genetic markers may be used to assist in the introgression of one or more transgenes of the invention from one genetic background into another. Marker assisted selection offers advantages relative to conventional breeding in that it can be used to avoid errors caused by phenotypic variations. Further, genetic markers may provide data regarding the relative degree of elite germplasm in the individual progeny of a particular cross. For example, when a plant with a desired trait which otherwise has a non-agronomically desirable genetic background is crossed to an elite parent, genetic markers may be used to select progeny which not only possess the trait of interest, but also have a relatively large proportion of the desired germplasm. In this way, the number of generations required to introgress one or more traits into a particular genetic background is minimized.

The present invention also relates to methods of producing a polypeptide of the present invention comprising: (a) cultivating a transgenic plant or a plant cell comprising a polynucleotide encoding the polypeptide under conditions conducive for production of the polypeptide; and (b) recovering the polypeptide.

Removal or Reduction of Beta-Glucosidase Activity, Beta-Xylosidase Activity, or Beta-Glucosidase and Beta-Xylosidase Activity The present invention also relates to methods of producing a mutant of a parent cell, which comprises disrupting or deleting a polynucleotide, or a portion thereof, encoding a polypeptide of the present invention, which results in the mutant cell producing less of the polypeptide than the parent cell when cultivated under the same conditions.

The mutant cell may be constructed by reducing or eliminating expression of the polynucleotide using methods well known in the art, for example, insertions, disruptions, replacements, or deletions. In a preferred aspect, the polynucleotide is inactivated. The polynucleotide to be modified or inactivated may be, for example, the coding region or a part thereof essential for activity, or a regulatory element required for expression of the coding region. An example of such a regulatory or control sequence may be a promoter sequence or a functional part thereof, i.e., a part that is sufficient for affecting expression of the polynucleotide. Other control sequences for possible modification include, but are not limited to, a leader, polyadenylation sequence, propeptide sequence, signal peptide sequence, transcription terminator, and transcriptional activator.

Modification or inactivation of the polynucleotide may be performed by subjecting the parent cell to mutagenesis and selecting for mutant cells in which expression of the polynucleotide has been reduced or eliminated. The mutagenesis, which may be specific or random, may be performed, for example, by use of a suitable physical or chemical mutagenizing agent, by use of a suitable oligonucleotide, or by subjecting the DNA sequence to PCR generated mutagenesis. Furthermore, the mutagenesis may be performed by use of any combination of these mutagenizing agents.

Examples of a physical or chemical mutagenizing agent suitable for the present purpose include ultraviolet (UV) irradiation, hydroxylamine, N-methyl-N'-nitro-N-nitrosoguanidine (MNNG), O-methyl hydroxylamine, nitrous acid, ethyl methane sulphonate (EMS), sodium bisulphite, formic acid, and nucleotide analogues.

When such agents are used, the mutagenesis is typically performed by incubating the parent cell to be mutagenized in the presence of the mutagenizing agent of choice under suitable conditions, and screening and/or selecting for mutant cells exhibiting reduced or no expression of the gene.

Modification or inactivation of the polynucleotide may also be accomplished by insertion, substitution, or deletion of one or more nucleotides in the gene or a regulatory element required for transcription or translation thereof. For example, nucleotides may be inserted or removed so as to result in the introduction of a stop codon, the removal of the start codon, or a change in the open reading frame. Such modification or inactivation may be accomplished by site-directed mutagenesis or PCR generated mutagenesis in accordance with methods known in the art. Although, in principle, the modification may be performed in vivo, i.e., directly on the cell expressing the polynucleotide to be modified, it is preferred that the modification be performed in vitro as exemplified below.

An example of a convenient way to eliminate or reduce expression of a polynucleotide is based on techniques of gene replacement, gene deletion, or gene disruption. For example, in the gene disruption method, a nucleic acid sequence corresponding to the endogenous polynucleotide is mutagenized in vitro to produce a defective nucleic acid sequence that is then transformed into the parent cell to produce a defective gene. By homologous recombination, the defective nucleic acid sequence replaces the endogenous polynucleotide. It may be desirable that the defective polynucleotide also encodes a marker that may be used for selection of transformants in which the polynucleotide has been modified or destroyed. In an aspect, the polynucleotide is disrupted with a selectable marker such as those described herein.

The present invention also relates to methods of inhibiting the expression of a polypeptide having beta-glucosidase activity, beta-xylosidase activity, or beta-glucosidase and beta-xylosidase activity in a cell, comprising administering to the cell or expressing in the cell a double-stranded RNA (dsRNA) molecule, wherein the dsRNA comprises a subsequence of a polynucleotide of the present invention. In a preferred aspect, the dsRNA is about 15, 16, 17, 18, 19, 20, 21, 22, 23, 24, 25 or more duplex nucleotides in length.

The dsRNA is preferably a small interfering RNA (siRNA) or a micro RNA (miRNA). In a preferred aspect, the dsRNA is small interfering RNA for inhibiting transcription. In another preferred aspect, the dsRNA is micro RNA for inhibiting translation.

The present invention also relates to such double-stranded RNA (dsRNA) molecules, comprising a portion of the mature polypeptide coding sequence of SEQ ID NO: 1, SEQ ID NO: 3, SEQ ID NO: 5, SEQ ID NO: 7, SEQ ID NO: 9, or SEQ ID NO: 11 for inhibiting expression of the polypeptide in a cell. While the present invention is not limited by any particular mechanism of action, the dsRNA can enter a cell and cause the degradation of a single-stranded RNA (ssRNA) of similar or identical sequences, including endogenous mRNAs. When a cell is exposed to dsRNA, mRNA from the homologous gene is selectively degraded by a process called RNA interference (RNAi).

The dsRNAs of the present invention can be used in gene-silencing. In one aspect, the invention provides methods to selectively degrade RNA using a dsRNAi of the present invention. The process may be practiced in vitro, ex vivo or in vivo. In one aspect, the dsRNA molecules can be used to generate a loss-of-function mutation in a cell, an organ or an animal. Methods for making and using dsRNA molecules to selectively degrade RNA are well known in the art; see, for example, U.S. Pat. Nos. 6,489,127; 6,506,559; 6,511,824; and 6,515,109.

The present invention further relates to a mutant cell of a parent cell that comprises a disruption or deletion of a polynucleotide encoding the polypeptide or a control sequence thereof or a silenced gene encoding the polypeptide, which results in the mutant cell producing less of the polypeptide or no polypeptide compared to the parent cell.

The polypeptide-deficient mutant cells are particularly useful as host cells for expression of native and heterologous polypeptides. Therefore, the present invention further relates to methods of producing a native or heterologous polypeptide, comprising: (a) cultivating the mutant cell under conditions conducive for production of the polypeptide; and (b) recovering the polypeptide. The term "heterologous polypeptides" means polypeptides that are not native to the host cell, e.g., a variant of a native protein. The host cell may comprise more than one copy of a polynucleotide encoding the native or heterologous polypeptide.

The methods used for cultivation and purification of the product of interest may be performed by methods known in the art.

The methods of the present invention for producing an essentially beta-glucosidase-beta-xylosidase-, or beta-glucosidase and beta-xylosidase-free product is of particular interest in the production of eukaryotic polypeptides, in particular fungal proteins such as enzymes. The beta-glucosidase-beta-xylosidase-, or beta-glucosidase and beta-xylosidase-deficient cells may also be used to express heterologous proteins of pharmaceutical interest such as hormones, growth factors, receptors, and the like. The term "eukaryotic polypeptides" includes not only native polypeptides, but also those polypeptides, e.g., enzymes, which have been modified by amino acid substitutions, deletions or additions, or other such modifications to enhance activity, thermostability, pH tolerance and the like.

In a further aspect, the present invention relates to a protein product essentially free from beta-glucosidase activity, beta-xylosidase activity, or beta-glucosidase and beta-xylosidase activity that is produced by a method of the present invention.

Compositions

The present invention also relates to compositions comprising a polypeptide of the present invention. Preferably, the compositions are enriched in such a polypeptide. The term "enriched" indicates that the beta-glucosidase activity, beta-xylosidase activity, or beta-glucosidase and beta-xylosidase activity of the composition has been increased, e.g., with an enrichment factor of at least 1.1.

The compositions may comprise a polypeptide of the present invention as the major enzymatic component, e.g., a mono-component composition. Alternatively, the compositions may comprise multiple enzymatic activities, such as one or more (several) enzymes selected from the group consisting of a cellulase, a hemicellulase, an expansin, an esterase, a laccase, a ligninolytic enzyme, a pectinase, a peroxidase, a protease, and a swollenin.

The compositions may be prepared in accordance with methods known in the art and may be in the form of a liquid or a dry composition. The polypeptide to be included in the composition may be stabilized in accordance with methods known in the art.

The compositions may be a fermentation broth formulation or a cell composition, as described herein. Consequently, the present invention also relates to fermentation broth formulations and cell compositions comprising a polypeptide having beta-glucosidase activity, beta-xylosidase activity, or beta-glucosidase and beta-xylosidase activity of the present invention. In some embodiments, the composition is a cell-killed whole broth containing organic acid(s), killed cells and/or cell debris, and culture medium.

The term "fermentation broth" as used herein refers to a preparation produced by cellular fermentation that undergoes no or minimal recovery and/or purification. For example, fermentation broths are produced when microbial cultures are grown to saturation, incubated under carbon-limiting conditions to allow protein synthesis (e.g., expression of enzymes by host cells) and secretion into cell culture medium. The fermentation broth can contain unfractionated or fractionated contents of the fermentation materials derived at the end of the fermentation. Typically, the fermentation broth is unfractionated and comprises the spent culture medium and cell debris present after the microbial cells (e.g., filamentous fungal cells) are removed, e.g., by centrifugation. In some embodiments, the fermentation broth contains spent cell culture medium, extracellular enzymes, and viable and/or non-viable microbial cells.

In an embodiment, the fermentation broth formulation and cell compositions comprise a first organic acid component comprising at least one 1-5 carbon organic acid and/or a salt thereof and a second organic acid component comprising at least one 6 or more carbon organic acid and/or a salt thereof. In a specific embodiment, the first organic acid component is acetic acid, formic acid, propionic acid, a salt thereof, or a mixture of two or more of the foregoing and the second organic acid component is benzoic acid, cyclohexanecarboxylic acid, 4-methylvaleric acid, phenylacetic acid, a salt thereof, or a mixture of two or more of the foregoing.

In one aspect, the composition contains an organic acid(s), and optionally further contains killed cells and/or cell debris. In one embodiment, the killed cells and/or cell debris are removed from a cell-killed whole broth to provide a composition that is free of these components.

The fermentation broth formulations or cell compostions may further comprise a preservative and/or anti-microbial (e.g., bacteriostatic) agent, including, but not limited to, sorbitol, sodium chloride, potassium sorbate, and others known in the art.

The cell-killed whole broth or composition may further comprise one or more enzyme activities such as cellobiohydrolase, endoglucanase, beta-glucosidase, endo-beta-1,3(4)-glucanase, glucohydrolase, xyloglucanase, xylanase, xylosidase, arabinofuranosidase, alpha-glucuronidase, acetyl xylan esterase, mannanase, mannosidase, alpha-galactosidase, mannan acetyl esterase, galactanase, arabinanase, pectate lyase, pectinase lyase, pectate lyase, polygalacturonase, pectin acetyl esterase, pectin methyl esterase, beta-galactosidase, galactanase, arabinanase, alpha-arabinofuranosidase, rhamnogalacturonase, ferrulic acid esterases rhamnogalacturonan lyase, rhamnogalacturonan acetyl esterase, xylogalacturonosidase, xylogalacturonase, rhamnogalacturonan lyase, lignin peroxidases, manganese-dependent peroxidases, hybrid peroxidases, with combined properties of lignin peroxidases and manganese-dependent peroxidases, glucoamylase, amylase, protease, and laccase.

In some embodiments, the cell-killed whole broth or composition includes cellulolytic enzymes including, but not limited to, (i) endoglucanases (EG) or 1,4-D-glucan-4-glucanohydrolases (EC 3.2.1.4), (ii) exoglucanases, including 1,4-D-glucan glucanohydrolases (also known as cellodextrinases) (EC 3.2.1.74) and 1,4-D-glucan cellobiohydrolases (exo-cellobiohydrolases, CBH) (EC 3.2.1.91), and (iii) beta-glucosidase (BG) or beta-glucoside glucohydrolases (EC 3.2.1.21).

The cell-killed whole broth or composition may contain the unfractionated contents of the fermentation materials derived at the end of the fermentation. Typically, the cell-killed whole broth or composition contains the spent culture medium and cell debris present after the microbial cells (e.g., filamentous fungal cells) are grown to saturation, incubated under carbon-limiting conditions to allow protein synthesis (e.g., expression of cellulase and/or glucosidase enzyme(s)). In some embodiments, the cell-killed whole broth or composition contains the spent cell culture medium, extracellular enzymes, and killed filamentous fungal cells. In some embodiments, the microbial cells present in the cell-killed whole broth or composition can be permeabilized and/or lysed using methods known in the art.

A whole broth or cell composition as described herein is typically a liquid, but may contain insoluble components, such as killed cells, cell debris, culture media components, and/or insoluble enzyme(s). In some embodiments, insoluble components may be removed to provide a clarified liquid composition.

The whole broth formulations and cell compositions of the present invention may be produced by a method described in WO 90/15861 or WO 2010/096673.

Examples are given below of preferred uses of the compositions of the present invention. The dosage of the composition and other conditions under which the composition is used may be determined on the basis of methods known in the art.

Uses

The present invention is also directed to the following processes for using the polypeptides having beta-glucosidase activity, beta-xylosidase activity, or beta-glucosidase and beta-xylosidase activity, or compositions thereof.

The present invention also relates to processes for degrading a cellulosic material or xylan-containing material, comprising: treating the cellulosic material or xylan-containing material with an enzyme composition in the presence of a polypeptide having beta-glucosidase activity, beta-xylosidase activity, or beta-glucosidase and beta-xylosidase activity of the present invention. In one aspect, the processes further comprise recovering the degraded or converted cellulosic material or xylan-containing material. Soluble products of degradation or conversion of the cellulosic material or xylan-containing material can be separated from insoluble cellulosic material or xylan-containing material using a method known in the art such as, for example, centrifugation, filtration, or gravity settling.

The present invention also relates to processes of producing a fermentation product, comprising: (a) saccharifying a cellulosic material or xylan-containing material with an enzyme composition in the presence of a polypeptide having beta-glucosidase activity, beta-xylosidase activity, or beta-glucosidase and beta-xylosidase activity of the present invention; (b) fermenting the saccharified cellulosic material or xylan-containing material with one or more (e.g., several) fermenting microorganisms to produce the fermentation product; and (c) recovering the fermentation product from the fermentation.

The present invention also relates to processes of fermenting a cellulosic material or xylan-containing material, comprising: fermenting the cellulosic material or xylan-containing material with one or more (e.g., several) fermenting microorganisms, wherein the cellulosic material or xylan-containing material is saccharified with an enzyme composition in the presence of a polypeptide having beta-glucosidase activity, beta-xylosidase activity, or beta-glucosidase and beta-xylosidase activity of the present invention. In one aspect, the fermenting of the cellulosic material or xylan-containing material produces a fermentation product. In another aspect, the processes further comprise recovering the fermentation product from the fermentation.

The processes of the present invention can be used to saccharify the cellulosic material or xylan-containing material to fermentable sugars and to convert the fermentable sugars to many useful fermentation products, e.g., fuel, potable ethanol, and/or platform chemicals (e.g., acids, alcohols, ketones, gases, and the like). The production of a desired fermentation product from the cellulosic material or xylan-containing material typically involves pretreatment, enzymatic hydrolysis (saccharification), and fermentation.

The processing of the cellulosic material or xylan-containing material according to the present invention can be accomplished using methods conventional in the art. Moreover, the processes of the present invention can be implemented using any conventional biomass processing apparatus configured to operate in accordance with the invention.

Hydrolysis (saccharification) and fermentation, separate or simultaneous, include, but are not limited to, separate hydrolysis and fermentation (SHF); simultaneous saccharification and fermentation (SSF); simultaneous saccharification and co-fermentation (SSCF); hybrid hydrolysis and fermentation (HHF); separate hydrolysis and co-fermentation (SHCF); hybrid hydrolysis and co-fermentation (HHCF); and direct microbial conversion (DMC), also sometimes called consolidated bioprocessing (CBP). SHF uses separate process steps to first enzymatically hydrolyze the cellulosic material or xylan-containing material to fermentable sugars, e.g., glucose, cellobiose, and pentose monomers, and then ferment the fermentable sugars to ethanol. In SSF, the enzymatic hydrolysis of the cellulosic material or xylan-containing material and the fermentation of sugars to ethanol are combined in one step (Philippidis, G. P., 1996, Cellulose bioconversion technology, in *Handbook on Bioethanol: Production and Utilization*, Wyman, C. E., ed., Taylor & Francis, Washington, D.C., 179-212). SSCF involves the co-fermentation of multiple sugars (Sheehan, J., and Himmel, M., 1999, Enzymes, energy and the environment: A strategic perspective on the U.S. Department of Energy's research and development activities for bioethanol, *Biotechnol. Prog.* 15: 817-827). HHF involves a separate hydrolysis step, and in addition a simultaneous saccharification and hydrolysis step, which can be carried out in the same reactor. The steps in an HHF process can be carried out at different temperatures, i.e., high temperature enzymatic saccharification followed by SSF at a lower temperature that the fermentation strain can tolerate. DMC combines all three processes (enzyme production, hydrolysis, and fermentation) in one or more (e.g., several) steps where the same organism is used to produce the enzymes for conversion of the cellulosic material or xylan-containing material to fermentable sugars and to convert the fermentable sugars into a final product (Lynd, L. R., Weimer, P. J., van Zyl, W. H., and Pretorius, I. S., 2002, Microbial cellulose utilization: Fundamentals and biotechnology, *Microbiol. Mol. Biol. Reviews* 66: 506-577). It is understood herein that any method known in the art comprising pretreatment, enzymatic hydrolysis (saccharification), fermentation, or a combination thereof, can be used in the practicing the processes of the present invention.

A conventional apparatus can include a fed-batch stirred reactor, a batch stirred reactor, a continuous flow stirred reactor with ultrafiltration, and/or a continuous plug-flow column reactor (Fernanda de Castilhos Corazza, Flávio Faria de Moraes, Gisella Maria Zanin and Ivo Neitzel, 2003, Optimal control in fed-batch reactor for the cellobiose hydrolysis, *Acta Scientiarum. Technology* 25: 33-38; Gusakov, A. V., and Sinitsyn, A. P., 1985, Kinetics of the enzymatic hydrolysis of cellulose: 1. A mathematical model for a batch reactor process, *Enz. Microb. Technol.* 7: 346-352), an attrition reactor (Ryu, S. K., and Lee, J. M., 1983, Bioconversion of waste cellulose by using an attrition bioreactor, *Biotechnol. Bioeng.* 25: 53-65), or a reactor with intensive stirring induced by an electromagnetic field (Gusakov, A. V., Sinitsyn, A. P., Davydkin, I. Y., Davydkin, V. Y., Protas, O. V., 1996, Enhancement of enzymatic cellulose hydrolysis using a novel type of bioreactor with intensive stirring induced by electromagnetic field, *Appl. Biochem. Biotechnol.* 56: 141-153). Additional reactor types include fluidized bed, upflow blanket, immobilized, and extruder type reactors for hydrolysis and/or fermentation.

Pretreatment.

In practicing the processes of the present invention, any pretreatment process known in the art can be used to disrupt plant cell wall components of the cellulosic material or xylan-containing material (Chandra et al., 2007, Substrate pretreatment: The key to effective enzymatic hydrolysis of lignocellulosics?, *Adv. Biochem. Engin./Biotechnol.* 108: 67-93; Galbe and Zacchi, 2007, Pretreatment of lignocellulosic materials for efficient bioethanol production, *Adv. Biochem. Engin./Biotechnol.* 108: 41-65; Hendriks and Zeeman, 2009, Pretreatments to enhance the digestibility of lignocellulosic biomass, *Bioresource Technol.* 100: 10-18; Mosier et al., 2005, Features of promising technologies for pretreatment of lignocellulosic biomass, *Bioresource Technol.* 96: 673-686; Taherzadeh and Karimi, 2008, Pretreatment of lignocellulosic wastes to improve ethanol and biogas production: A review, *Int. J. of Mol. Sci.* 9: 1621-1651; Yang and Wyman, 2008, Pretreatment: the key to unlocking low-cost cellulosic ethanol, *Biofuels Bioproducts and Biorefining-Biofpr.* 2: 26-40).

The cellulosic material or xylan-containing material can also be subjected to particle size reduction, sieving, presoaking, wetting, washing, and/or conditioning prior to pretreatment using methods known in the art.

Conventional pretreatments include, but are not limited to, steam pretreatment (with or without explosion), dilute acid pretreatment, hot water pretreatment, alkaline pretreatment, lime pretreatment, wet oxidation, wet explosion, ammonia fiber explosion, organosolv pretreatment, and biological pretreatment. Additional pretreatments include ammonia percolation, ultrasound, electroporation, microwave, supercritical $CO_2$, supercritical $H_2O$, ozone, ionic liquid, and gamma irradiation pretreatments.

The cellulosic material or xylan-containing material can be pretreated before hydrolysis and/or fermentation. Pretreatment is preferably performed prior to the hydrolysis. Alternatively, the pretreatment can be carried out simultaneously with enzyme hydrolysis to release fermentable sugars, such as glucose, xylose, and/or cellobiose. In most cases the pretreatment step itself results in some conversion of biomass to fermentable sugars (even in absence of enzymes).

Steam Pretreatment. In steam pretreatment, the cellulosic material or xylan-containing material is heated to disrupt the plant cell wall components, including lignin, hemicellulose, and cellulose to make the cellulose and other fractions, e.g., hemicellulose, accessible to enzymes. The cellulosic material or xylan-containing material is passed to or through a reaction vessel where steam is injected to increase the temperature to the required temperature and pressure and is retained therein for the desired reaction time. Steam pretreatment is preferably performed at 140-250° C., e.g., 160-200° C. or 170-190° C., where the optimal temperature range depends on addition of a chemical catalyst. Residence time for the steam pretreatment is preferably 1-60 minutes, e.g., 1-30 minutes, 1-20 minutes, 3-12 minutes, or 4-10 minutes, where the optimal residence time depends on temperature range and addition of a chemical catalyst. Steam pretreatment allows for relatively high solids loadings, so that the cellulosic material or xylan-containing material is generally only moist during the pretreatment. The steam pretreatment is often combined with an explosive discharge of the material after the pretreatment, which is known as steam explosion, that is, rapid flashing to atmospheric pressure and turbulent flow of the material to increase the accessible surface area by fragmentation (Duff and Murray, 1996, *Bioresource Technology* 855: 1-33; Galbe and Zacchi, 2002, *Appl. Microbiol. Biotechnol.* 59: 618-628; U.S. Patent Application No. 20020164730). During steam pretreatment, hemicellulose acetyl groups are cleaved and the resulting acid autocatalyzes partial hydrolysis of the hemicellulose to monosaccharides and oligosaccharides. Lignin is removed to only a limited extent.

Chemical Pretreatment: The term "chemical treatment" refers to any chemical pretreatment that promotes the separation and/or release of cellulose, hemicellulose, and/or lignin. Such a pretreatment can convert crystalline cellulose to amorphous cellulose. Examples of suitable chemical pretreatment processes include, for example, dilute acid pretreatment, lime pretreatment, wet oxidation, ammonia fiber/freeze explosion (AFEX), ammonia percolation (APR), ionic liquid, and organosolv pretreatments.

A catalyst such as $H_2SO_4$ or $SO_2$ (typically 0.3 to 5% w/w) is often added prior to steam pretreatment, which decreases the time and temperature, increases the recovery, and improves enzymatic hydrolysis (Ballesteros et al., 2006, *Appl. Biochem. Biotechnol.* 129-132: 496-508; Varga et al., 2004, *Appl. Biochem. Biotechnol.* 113-116: 509-523; Sassner et al., 2006, *Enzyme Microb. Technol.* 39: 756-762). In dilute acid pretreatment, the cellulosic material or xylan-containing material is mixed with dilute acid, typically $H_2SO_4$, and water to form a slurry, heated by steam to the desired temperature, and after a residence time flashed to atmospheric pressure. The dilute acid pretreatment can be performed with a number of reactor designs, e.g., plug-flow reactors, counter-current reactors, or continuous counter-current shrinking bed reactors (Duff and Murray, 1996, supra; Schell et al., 2004, *Bioresource Technol.* 91: 179-188; Lee et al., 1999, *Adv. Biochem. Eng. Biotechnol.* 65: 93-115).

Several methods of pretreatment under alkaline conditions can also be used. These alkaline pretreatments include, but are not limited to, sodium hydroxide, lime, wet oxidation, ammonia percolation (APR), and ammonia fiber/freeze explosion (AFEX).

Lime pretreatment is performed with calcium oxide or calcium hydroxide at temperatures of 85-150° C. and residence times from 1 hour to several days (Wyman et al., 2005, *Bioresource Technol.* 96: 1959-1966; Mosier et al., 2005, *Bioresource Technol.* 96: 673-686). WO 2006/110891, WO 2006/110899, WO 2006/110900, and WO 2006/110901 disclose pretreatment methods using ammonia.

Wet oxidation is a thermal pretreatment performed typically at 180-200° C. for 5-15 minutes with addition of an oxidative agent such as hydrogen peroxide or over-pressure of oxygen (Schmidt and Thomsen, 1998, *Bioresource Technol.* 64: 139-151; Palonen et al., 2004, *Appl. Biochem. Biotechnol.* 117: 1-17; Varga et al., 2004, *Biotechnol. Bioeng.* 88: 567-574; Martin et al., 2006, *J. Chem. Technol. Biotechnol.* 81: 1669-1677). The pretreatment is performed preferably at 1-40% dry matter, e.g., 2-30% dry matter or 5-20% dry matter, and often the initial pH is increased by the addition of alkali such as sodium carbonate.

A modification of the wet oxidation pretreatment method, known as wet explosion (combination of wet oxidation and steam explosion) can handle dry matter up to 30%. In wet explosion, the oxidizing agent is introduced during pretreatment after a certain residence time. The pretreatment is then ended by flashing to atmospheric pressure (WO 2006/032282).

Ammonia fiber explosion (AFEX) involves treating the cellulosic material or xylan-containing material with liquid or gaseous ammonia at moderate temperatures such as 90-150° C. and high pressure such as 17-20 bar for 5-10 minutes, where the dry matter content can be as high as 60% (Gollapalli et al., 2002, *Appl. Biochem. Biotechnol.* 98: 23-35; Chundawat et al., 2007, *Biotechnol. Bioeng.* 96: 219-231; Alizadeh et al., 2005, *Appl. Biochem. Biotechnol.* 121: 1133-1141; Teymouri et al., 2005, *Bioresource Technol.* 96: 2014-2018). During AFEX pretreatment cellulose and hemicelluloses remain relatively intact. Lignin-carbohydrate complexes are cleaved.

Organosolv pretreatment delignifies the cellulosic material or xylan-containing material by extraction using aqueous ethanol (40-60% ethanol) at 160-200° C. for 30-60 minutes (Pan et al., 2005, *Biotechnol. Bioeng.* 90: 473-481; Pan et al., 2006, *Biotechnol. Bioeng.* 94: 851-861; Kurabi et al., 2005, *Appl. Biochem. Biotechnol.* 121: 219-230). Sulphuric acid is usually added as a catalyst. In organosolv pretreatment, the majority of hemicellulose and lignin is removed.

Other examples of suitable pretreatment methods are described by Schell et al., 2003, *Appl. Biochem. and Biotechnol.* Vol. 105-108, p. 69-85, and Mosier et al., 2005, *Bioresource Technology* 96: 673-686, and U.S. Published Application 2002/0164730.

In one aspect, the chemical pretreatment is preferably carried out as a dilute acid treatment, and more preferably as a continuous dilute acid treatment. The acid is typically sulfuric acid, but other acids can also be used, such as acetic acid, citric acid, nitric acid, phosphoric acid, tartaric acid, succinic acid, hydrogen chloride, or mixtures thereof. Mild acid treatment is conducted in the pH range of preferably 1-5, e.g., 1-4 or 1-2.5. In one aspect, the acid concentration is in the range from preferably 0.01 to 10 wt % acid, e.g., 0.05 to 5 wt % acid or 0.1 to 2 wt % acid. The acid is contacted with the cellulosic material or xylan-containing material and held at a temperature in the range of preferably 140-200° C., e.g., 165-190° C., for periods ranging from 1 to 60 minutes.

In another aspect, pretreatment takes place in an aqueous slurry. In preferred aspects, the cellulosic material or xylan-containing material is present during pretreatment in amounts preferably between 10-80 wt %, e.g., 20-70 wt % or 30-60 wt %, such as around 40 wt %. The pretreated cellulosic material or xylan-containing material can be unwashed or washed using any method known in the art, e.g., washed with water.

Mechanical Pretreatment or Physical Pretreatment: The term "mechanical pretreatment" or "physical pretreatment" refers to any pretreatment that promotes size reduction of particles. For example, such pretreatment can involve various types of grinding or milling (e.g., dry milling, wet milling, or vibratory ball milling).

The cellulosic material or xylan-containing material can be pretreated both physically (mechanically) and chemically. Mechanical or physical pretreatment can be coupled with steaming/steam explosion, hydrothermolysis, dilute or mild acid treatment, high temperature, high pressure treatment, irradiation (e.g., microwave irradiation), or combinations thereof. In one aspect, high pressure means pressure in the range of preferably about 100 to about 400 psi, e.g., about 150 to about 250 psi. In another aspect, high temperature means temperatures in the range of about 100 to about 300° C., e.g., about 140 to about 200° C. In a preferred aspect, mechanical or physical pretreatment is performed in a batch-process using a steam gun hydrolyzer system that uses high pressure and high temperature as defined above, e.g., a Sunds Hydrolyzer available from Sunds Defibrator AB, Sweden. The physical and chemical pretreatments can be carried out sequentially or simultaneously, as desired.

Accordingly, in a preferred aspect, the cellulosic material or xylan-containing material is subjected to physical (mechanical) or chemical pretreatment, or any combination thereof, to promote the separation and/or release of cellulose, hemicellulose, and/or lignin.

Biological Pretreatment The term "biological pretreatment" refers to any biological pretreatment that promotes the separation and/or release of cellulose, hemicellulose, and/or lignin from the cellulosic material or xylan-containing material. Biological pretreatment techniques can involve applying lignin-solubilizing microorganisms and/or enzymes (see, for example, Hsu, T.-A., 1996, Pretreatment of biomass, in *Handbook on Bioethanol: Production and Utilization*, Wyman, C. E., ed., Taylor & Francis, Washington, D.C., 179-212; Ghosh and Singh, 1993, Physicochemical and biological treatments for enzymatic/microbial conversion of cellulosic biomass, *Adv. Appl. Microbiol.* 39: 295-333; McMillan, J. D., 1994, Pretreating lignocellulosic biomass: a review, in *Enzymatic Conversion of Biomass for Fuels Production*, Himmel, M. E., Baker, J. O., and Overend, R. P., eds., ACS Symposium Series 566, American Chemical Society, Washington, D.C., chapter 15; Gong, C. S., Cao, N. J., Du, J., and Tsao, G. T., 1999, Ethanol production from renewable resources, in *Advances in Biochemical Engineering/Biotechnology*, Scheper, T., ed., Springer-Verlag Berlin Heidelberg, Germany, 65: 207-241; Olsson and Hahn-Hagerdal, 1996, Fermentation of lignocellulosic hydrolysates for ethanol production, *Enz. Microb. Tech.* 18: 312-331; and Vallander and Eriksson, 1990, Production of ethanol from lignocellulosic materials: State of the art, *Adv. Biochem. Eng./Biotechnol.* 42: 63-95).

Saccharification.

In the hydrolysis step, also known as saccharification, the cellulosic material or xylan-containing material, e.g., pretreated, is hydrolyzed to break down cellulose and/or hemicellulose to fermentable sugars, such as glucose, cellobiose, xylose, xylulose, arabinose, mannose, galactose, and/or soluble oligosaccharides. The hydrolysis is performed enzymatically by an enzyme composition as described herein in the presence of a polypeptide having beta-glucosidase activity, beta-xylosidase activity, or beta-glucosidase and beta-xylosidase activity of the present invention. The enzymes of the compositions can be added simultaneously or sequentially.

Enzymatic hydrolysis is preferably carried out in a suitable aqueous environment under conditions that can be readily determined by one skilled in the art. In one aspect, hydrolysis is performed under conditions suitable for the activity of the enzyme(s), i.e., optimal for the enzyme(s). The hydrolysis can be carried out as a fed batch or continuous process where the cellulosic material or xylan-containing material is fed gradually to, for example, an enzyme containing hydrolysis solution.

The saccharification is generally performed in stirred-tank reactors or fermentors under controlled pH, temperature, and mixing conditions. Suitable process time, temperature and pH conditions can readily be determined by one skilled in the art. For example, the saccharification can last up to 200 hours, but is typically performed for preferably about 12 to about 120 hours, e.g., about 16 to about 72 hours or about 24 to about 48 hours. The temperature is in the range of preferably about 25° C. to about 70° C., e.g., about 30° C. to about 65° C., about 40° C. to about 60° C., or about 50° C. to about 55° C. The pH is in the range of preferably about 3 to about 8, e.g., about 3.5 to about 7, about 4 to about 6, or about 5.0 to about 5.5. The dry solids content is in the range of preferably about 5 to about 50 wt %, e.g., about 10 to about 40 wt % or about 20 to about 30 wt %.

The enzyme compositions can comprise any protein useful in degrading the cellulosic material or xylan-containing material.

In one aspect, the enzyme composition comprises or further comprises one or more (e.g., several) proteins selected from the group consisting of a cellulase, a GH61 polypeptide having cellulolytic enhancing activity, a hemicellulase, an esterase, an expansin, a laccase, a ligninolytic enzyme, a pectinase, a peroxidase, a protease, and a swollenin. In another aspect, the cellulase is preferably one or more (e.g., several) enzymes selected from the group consisting of an endoglucanase, a cellobiohydrolase, and a beta-glucosidase. In another aspect, the hemicellulase is preferably one or more (e.g., several) enzymes selected from the group consisting of an acetylmannan esterase, an acetylxylan esterase, an arabinanase, an arabinofuranosidase, a coumaric acid esterase, a feruloyl esterase, a galactosidase, a glucuronidase, a glucuronoyl esterase, a mannanase, a mannosidase, a xylanase, and a xylosidase.

In another aspect, the enzyme composition comprises one or more (e.g., several) cellulolytic enzymes. In another aspect, the enzyme composition comprises or further comprises one or more (e.g., several) hemicellulolytic enzymes. In another aspect, the enzyme composition comprises one or more (e.g., several) cellulolytic enzymes and one or more (e.g., several) hemicellulolytic enzymes. In another aspect, the enzyme composition comprises one or more (e.g., several) enzymes selected from the group of cellulolytic enzymes and hemicellulolytic enzymes. In another aspect, the enzyme composition comprises an endoglucanase. In another aspect, the enzyme composition comprises a cellobiohydrolase. In another aspect, the enzyme composition comprises a beta-glucosidase. In another aspect, the enzyme composition comprises a polypeptide having cellulolytic enhancing activity. In another aspect, the enzyme composition comprises an endoglucanase and a polypeptide having cellulolytic enhancing activity. In another aspect, the enzyme composition comprises a cellobiohydrolase and a polypeptide having cellulolytic enhancing activity. In another aspect, the enzyme composition comprises a beta-glucosidase and a polypeptide having cellulolytic enhancing activity. In another aspect, the enzyme composition comprises an endoglucanase and a cellobiohydrolase. In another aspect, the enzyme composition comprises an endoglucanase and a beta-glucosidase. In another aspect, the enzyme composition comprises a cellobiohydrolase and a beta-glucosidase. In another aspect, the enzyme composition comprises an endoglucanase, a cellobiohydrolase, and a polypeptide having cellulolytic enhancing activity. In another aspect, the enzyme composition comprises an endoglucanase, a beta-glucosidase, and a polypeptide having cellulolytic enhancing activity. In another aspect, the enzyme composition comprises a cellobiohydrolase, a beta-glucosidase, and a polypeptide having cellulolytic enhancing activity. In another aspect, the enzyme composition comprises an endoglucanase, a cellobiohydrolase, and a beta-glucosidase. In another aspect, the enzyme composition comprises an endoglucanase, a cellobiohydrolase, a beta-glucosidase, and a polypeptide having cellulolytic enhancing activity.

In another aspect, the enzyme composition comprises an acetylmannan esterase. In another aspect, the enzyme composition comprises an acetylxylan esterase. In another aspect, the enzyme composition comprises an arabinanase (e.g., alpha-L-arabinanase). In another aspect, the enzyme composition comprises an arabinofuranosidase (e.g., alpha-L-arabinofuranosidase). In another aspect, the enzyme composition comprises a coumaric acid esterase. In another aspect, the enzyme composition comprises a feruloyl esterase. In another aspect, the enzyme composition comprises a galactosidase (e.g., alpha-galactosidase and/or beta-galactosidase). In another aspect, the enzyme composition comprises a glucuronidase (e.g., alpha-D-glucuronidase). In another aspect, the enzyme composition comprises a glucuronoyl esterase. In another aspect, the enzyme composition comprises a mannanase. In another aspect, the enzyme composition comprises a mannosidase (e.g., beta-mannosidase). In another aspect, the enzyme composition comprises a xylanase. In a preferred aspect, the xylanase is a Family 10 xylanase. In another aspect, the enzyme composition comprises a xylosidase (e.g., beta-xylosidase).

In another aspect, the enzyme composition comprises an esterase. In another aspect, the enzyme composition comprises an expansin. In another aspect, the enzyme composition comprises a laccase. In another aspect, the enzyme composition comprises a ligninolytic enzyme. In a preferred aspect, the ligninolytic enzyme is a manganese peroxidase. In another preferred aspect, the ligninolytic enzyme is a lignin peroxidase. In another preferred aspect, the ligninolytic enzyme is a $H_2O_2$-producing enzyme. In another aspect, the enzyme composition comprises a pectinase. In another aspect, the enzyme composition comprises a peroxidase. In another aspect, the enzyme composition comprises a protease. In another aspect, the enzyme composition comprises a swollenin.

In the processes of the present invention, the enzyme(s) can be added prior to or during fermentation, e.g., during saccharification or during or after propagation of the fermenting microorganism(s).

One or more (e.g., several) components of the enzyme composition may be wild-type proteins, recombinant proteins, or a combination of wild-type proteins and recombinant proteins. For example, one or more (e.g., several) components may be native proteins of a cell, which is used as a host cell to express recombinantly one or more (e.g., several) other components of the enzyme composition. One or more (e.g., several) components of the enzyme composition may be produced as monocomponents, which are then combined to form the enzyme composition. The enzyme composition may be a combination of multicomponent and monocomponent protein preparations.

The enzymes used in the processes of the present invention may be in any form suitable for use, such as, for example, a fermentation broth formulation or a cell composition, a cell lysate with or without cellular debris, a semi-purified or purified enzyme preparation, or a host cell as a source of the enzymes. The enzyme composition may be a dry powder or granulate, a non-dusting granulate, a liquid, a stabilized liquid, or a stabilized protected enzyme. Liquid enzyme preparations may, for instance, be stabilized by adding stabilizers such as a sugar, a sugar alcohol or another polyol, and/or lactic acid or another organic acid according to established processes.

The optimum amounts of the enzymes and a polypeptide having beta-glucosidase activity, beta-xylosidase activity, or beta-glucosidase and beta-xylosidase activity depend on several factors including, but not limited to, the mixture of component cellulolytic and/or hemicellulolytic enzymes, the cellulosic material or xylan-containing material, the concentration of cellulosic material or xylan-containing material, the pretreatment(s) of the cellulosic material or xylan-containing material, temperature, time, pH, and inclusion of fermenting organism (e.g., yeast for Simultaneous Saccharification and Fermentation).

In one aspect, an effective amount of cellulolytic or hemicellulolytic enzyme to the cellulosic material or xylan-containing material is about 0.5 to about 50 mg, e.g., about 0.5 to about 40 mg, about 0.5 to about 25 mg, about 0.75 to about 20 mg, about 0.75 to about 15 mg, about 0.5 to about 10 mg, or about 2.5 to about 10 mg per g of the cellulosic material or xylan-containing material.

In another aspect, an effective amount of a polypeptide having beta-glucosidase activity, beta-xylosidase activity, or beta-glucosidase and beta-xylosidase activity to the cellulosic material or xylan-containing material is about 0.01 to about 50.0 mg, e.g., about 0.01 to about 40 mg, about 0.01 to about 30 mg, about 0.01 to about 20 mg, about 0.01 to about 10 mg, about 0.01 to about 5 mg, about 0.025 to about 1.5 mg, about 0.05 to about 1.25 mg, about 0.075 to about 1.25 mg, about 0.1 to about 1.25 mg, about 0.15 to about 1.25 mg, or about 0.25 to about 1.0 mg per g of the cellulosic material or xylan-containing material.

In another aspect, an effective amount of a polypeptide having beta-glucosidase activity, beta-xylosidase activity, or beta-glucosidase and beta-xylosidase activity to cellulolytic or hemicellulolytic enzyme is about 0.005 to about 1.0 g, e.g., about 0.01 to about 1.0 g, about 0.15 to about 0.75 g, about 0.15 to about 0.5 g, about 0.1 to about 0.5 g, about 0.1 to about 0.25 g, or about 0.05 to about 0.2 g per g of cellulolytic or hemicellulolytic enzyme.

The polypeptides having cellulolytic enzyme activity or hemicellulolytic enzyme activity as well as other proteins/ polypeptides useful in the degradation of the cellulosic material or xylan-containing material, e.g., GH61 polypeptides having cellulolytic enhancing activity (collectively hereinafter "polypeptides having enzyme activity") can be derived or obtained from any suitable origin, including, bacterial, fungal, yeast, plant, or mammalian origin. The term "obtained" also means herein that the enzyme may have been produced recombinantly in a host organism employing methods described herein, wherein the recombinantly produced enzyme is either native or foreign to the host organism or has a modified amino acid sequence, e.g., having one or more (e.g., several) amino acids that are deleted, inserted and/or substituted, i.e., a recombinantly produced enzyme that is a mutant and/or a fragment of a native amino acid sequence or an enzyme produced by nucleic acid shuffling processes known in the art. Encompassed within the meaning of a native enzyme are natural variants and within the meaning of a foreign enzyme are variants obtained recombinantly, such as by site-directed mutagenesis or shuffling.

A polypeptide having enzyme activity may be a bacterial polypeptide. For example, the polypeptide may be a gram positive bacterial polypeptide such as a *Bacillus*, *Streptococcus*, *Streptomyces*, *Staphylococcus*, *Enterococcus*, *Lactobacillus*, *Lactococcus*, *Clostridium*, *Geobacillus*, *Caldicellulosiruptor*, *Acidothermus*, *Thermobifidia*, or *Oceanobacillus* polypeptide having enzyme activity, or a Gram negative bacterial polypeptide such as an *E. coli*, *Pseudomonas*, *Salmonella*, *Campylobacter*, *Helicobacter*, *Flavobacterium*, *Fusobacterium*, *Ilyobacter*, *Neisseria*, or *Ureaplasma* polypeptide having enzyme activity.

In one aspect, the polypeptide is a *Bacillus alkalophilus*, *Bacillus amyloliquefaciens*, *Bacillus brevis*, *Bacillus circulans*, *Bacillus clausii*, *Bacillus coagulans*, *Bacillus firmus*, *Bacillus lautus*, *Bacillus lentus*, *Bacillus licheniformis*, *Bacillus megaterium*, *Bacillus pumilus*, *Bacillus stearothermophilus*, *Bacillus subtilis*, or *Bacillus thuringiensis* polypeptide having enzyme activity.

In another aspect, the polypeptide is a *Streptococcus equisimilis*, *Streptococcus pyogenes*, *Streptococcus uberis*, or *Streptococcus equi* subsp. *Zooepidemicus* polypeptide having enzyme activity.

In another aspect, the polypeptide is a *Streptomyces achromogenes*, *Streptomyces avermitilis*, *Streptomyces coelicolor*, *Streptomyces griseus*, or *Streptomyces lividans* polypeptide having enzyme activity.

The polypeptide having enzyme activity may also be a fungal polypeptide, and more preferably a yeast polypeptide such as a *Candida*, *Kluyveromyces*, *Pichia*, *Saccharomyces*, *Schizosaccharomyces*, or *Yarrowia* polypeptide having enzyme activity; or more preferably a filamentous fungal polypeptide such as an *Acremonium*, *Agaricus*, *Alternaria*, *Aspergillus*, *Aureobasidium*, *Botryospaeria*, *Ceriporiopsis*, *Chaetomidium*, *Chrysosporium*, *Claviceps*, *Cochliobolus*, *Coprinopsis*, *Coptotermes*, *Corynascus*, *Cryphonectria*, *Cryptococcus*, *Diplodia*, *Exidia*, *Filibasidium*, *Fusarium*, *Gibberella*, *Holomastigotoides*, *Humicola*, *Irpex*, *Lentinula*, *Leptospaeria*, *Magnaporthe*, *Melanocarpus*, *Meripilus*, *Mucor*, *Myceliophthora*, *Neocallimastix*, *Neurospora*, *Paecilomyces*, *Penicillium*, *Phanerochaete*, *Piromyces*, *Poitrasia*, *Pseudoplectania*, *Pseudotrichonympha*, *Rhizomucor*, *Schizophyllum*, *Scytalidium*, *Talaromyces*, *Thermoascus*, *Thielavia*, *Tolypocladium*, *Trichoderma*, *Trichophaea*, *Verticillium*, *Volvariella*, or *Xylaria* polypeptide having enzyme activity.

In one aspect, the polypeptide is a *Saccharomyces carlsbergensis*, *Saccharomyces cerevisiae*, *Saccharomyces diastaticus*, *Saccharomyces douglasii*, *Saccharomyces kluyveri*, *Saccharomyces norbensis*, or *Saccharomyces oviformis* polypeptide having enzyme activity.

In another aspect, the polypeptide is an *Acremonium cellulolyticus*, *Aspergillus aculeatus*, *Aspergillus awamori*, *Aspergillus fumigatus*, *Aspergillus foetidus*, *Aspergillus japonicus*, *Aspergillus nidulans*, *Aspergillus niger*, *Aspergillus oryzae*, *Chrysosporium keratinophilum*, *Chrysosporium lucknowense*, *Chrysosporium tropicum*, *Chrysosporium merdarium*, *Chrysosporium inops*, *Chrysosporium pannicola*, *Chrysosporium queenslandicum*, *Chrysosporium zonatum*, *Fusarium bactridioides*, *Fusarium cerealis*, *Fusarium crookwellense*, *Fusarium culmorum*, *Fusarium graminearum*, *Fusarium graminum*, *Fusarium heterosporum*, *Fusarium negundi*, *Fusarium oxysporum*, *Fusarium reticulatum*, *Fusarium roseum*, *Fusarium sambucinum*, *Fusarium sarcochroum*, *Fusarium sporotrichioides*, *Fusarium sulphureum*, *Fusarium torulosum*, *Fusarium trichothecioides*, *Fusarium venenatum*, *Humicola grisea*, *Humicola insolens*, *Humicola lanuginosa*, *Irpex lacteus*, *Mucor miehei*, *Myceliophthora thermophila*, *Neurospora crassa*, *Penicillium funiculosum*, *Penicillium purpurogenum*, *Phanerochaete chrysosporium*, *Thielavia achromatica*, *Thielavia albomyces*, *Thielavia albopilosa*, *Thielavia australeinsis*, *Thielavia fimeti*, *Thielavia microspora*, *Thielavia ovispora*, *Thielavia peruviana*, *Thielavia spededonium*, *Thielavia setosa*, *Thielavia subthermophila*, *Thielavia terrestris*, *Trichoderma harzianum*, *Trichoderma koningii*, *Trichoderma longibrachiatum*, *Trichoderma reesei*, *Trichoderma viride*, or *Trichophaea saccata* polypeptide having enzyme activity.

Chemically modified or protein engineered mutants of polypeptides having enzyme activity may also be used.

One or more (e.g., several) components of the enzyme composition may be a recombinant component, i.e., produced by cloning of a DNA sequence encoding the single component and subsequent cell transformed with the DNA sequence and expressed in a host (see, for example, WO 91/17243 and WO 91/17244). The host is preferably a heterologous host (enzyme is foreign to host), but the host may under certain conditions also be a homologous host (enzyme is native to host). Monocomponent cellulolytic proteins may also be prepared by purifying such a protein from a fermentation broth.

In one aspect, the one or more (e.g., several) cellulolytic enzymes comprise a commercial cellulolytic enzyme preparation. Examples of commercial cellulolytic enzyme preparations suitable for use in the present invention include, for example, CELLIC® CTec (Novozymes A/S), CELLIC® CTec2 (Novozymes A/S), CELLUCLAST™ (Novozymes A/S), NOVOZYM™ 188 (Novozymes A/S), CELLUZYME™ (Novozymes A/S), CEREFLO™ (Novozymes A/S), and ULTRAFLO™ (Novozymes A/S), ACCELERASE™ (Genencor Int.), LAMINEX™ (Genencor Int.), SPEZYME™ CP (Genencor Int.), FILTRASE® NL (DSM); METHAPLUS® S/L 100 (DSM), ROHAMENT™ 7069 W (Röhm GmbH), FIBREZYME® LDI (Dyadic International, Inc.), FIBREZYME® LBR (Dyadic International, Inc.), or VISCOSTAR® 150L (Dyadic International, Inc.). The cellulase enzymes are added in amounts effective from about 0.001 to about 5.0 wt % of solids, e.g., about 0.025 to about 4.0 wt % of solids or about 0.005 to about 2.0 wt % of solids.

Examples of bacterial endoglucanases that can be used in the processes of the present invention, include, but are not limited to, an Acidothermus cellulolyticus endoglucanase (WO 91/05039; WO 93/15186; U.S. Pat. No. 5,275,944; WO 96/02551; U.S. Pat. No. 5,536,655, WO 00/70031, WO 05/093050); *Thermobifida fusca* endoglucanase III (WO 05/093050); and *Thermobifida fusca* endoglucanase V (WO 05/093050).

Examples of fungal endoglucanases that can be used in the present invention, include, but are not limited to, a *Trichoderma reesei* endoglucanase I (Penttila et al., 1986, *Gene* 45: 253-263, *Trichoderma reesei* Cel7B endoglucanase I (GENBANK™ accession no. M15665), *Trichoderma reesei* endoglucanase II (Saloheimo, et al., 1988, *Gene* 63:11-22), *Trichoderma reesei* Cel5A endoglucanase II (GENBANK™ accession no. M19373), *Trichoderma reesei* endoglucanase III (Okada et al., 1988, *Appl. Environ. Microbiol.* 64: 555-563, GENBANK™ accession no. AB003694), *Trichoderma reesei* endoglucanase V (Saloheimo et al., 1994, *Molecular Microbiology* 13: 219-228, GENBANK™ accession no. Z33381), *Aspergillus aculeatus* endoglucanase (Ooi et al., 1990, *Nucleic Acids Research* 18: 5884), *Aspergillus kawachii* endoglucanase (Sakamoto et al., 1995, *Current Genetics* 27: 435-439), *Erwinia carotovara* endoglucanase (Saarilahti et al., 1990, *Gene* 90: 9-14), *Fusarium oxysporum* endoglucanase (GENBANK™ accession no. L29381), *Humicola grisea* var. *thermoidea* endoglucanase (GENBANK™ accession no. AB003107), Melanocarpus albomyces endoglucanase (GENBANK™ accession no. MAL515703), *Neurospora crassa* endoglucanase (GENBANK™ accession no. XM_324477), *Humicola insolens* endoglucanase V, *Myceliophthora thermophila* CBS 117.65 endoglucanase, basidiomycete CBS 495.95 endoglucanase, basidiomycete CBS 494.95 endoglucanase, *Thielavia terrestris* NRRL 8126 CEL6B endoglucanase, *Thielavia terrestris* NRRL 8126 CEL6C endoglucanase, *Thielavia terrestris* NRRL 8126 CEL7C endoglucanase, *Thielavia terrestris* NRRL 8126 CEL7E endoglucanase, *Thielavia terrestris* NRRL 8126 CEL7F endoglucanase, *Cladorrhinum foecundissimum* ATCC 62373 CEL7A endoglucanase, and *Trichoderma reesei* strain No. VTT-D-80133 endoglucanase (GENBANK™ accession no. M15665).

Examples of cellobiohydrolases useful in the present invention include, but are not limited to, *Aspergillus aculeatus* cellobiohydrolase II (WO 2011/059740), *Chaetomium thermophilum* cellobiohydrolase I, *Chaetomium thermophilum* cellobiohydrolase II, *Humicola insolens* cellobiohydrolase I, *Myceliophthora thermophila* cellobiohydrolase II (WO 2009/042871), *Thielavia hyrcanie* cellobiohydrolase II (WO 2010/141325), *Thielavia terrestris* cellobiohydrolase II (CEL6A, WO 2006/074435), *Trichoderma reesei* cellobiohydrolase I, *Trichoderma reesei* cellobiohydrolase II, and *Trichophaea saccata* cellobiohydrolase II (WO 2010/057086).

Examples of beta-glucosidases useful in the present invention include, but are not limited to, beta-glucosidases from *Aspergillus aculeatus* (Kawaguchi et al., 1996, *Gene* 173: 287-288), *Aspergillus fumigatus* (WO 2005/047499), *Aspergillus niger* (Dan et al., 2000, *J. Biol. Chem.* 275: 4973-4980), *Aspergillus oryzae* (WO 2002/095014), *Penicillium brasilianum* IBT 20888 (WO 2007/019442 and WO 2010/088387), *Thielavia terrestris* (WO 2011/035029), and *Trichophaea saccata* (WO 2007/019442).

The beta-glucosidase may be a fusion protein. In one aspect, the beta-glucosidase is an *Aspergillus oryzae* beta-glucosidase variant BG fusion protein (WO 2008/057637) or an *Aspergillus oryzae* beta-glucosidase fusion protein (WO 2008/057637).

Other useful endoglucanases, cellobiohydrolases, and beta-glucosidases are disclosed in numerous Glycosyl Hydrolase families using the classification according to Henrissat B., 1991, A classification of glycosyl hydrolases based on amino-acid sequence similarities, *Biochem. J.* 280: 309-316, and Henrissat B., and Bairoch A., 1996, Updating the sequence-based classification of glycosyl hydrolases, *Biochem. J.* 316: 695-696.

Other cellulolytic enzymes that may be used in the present invention are described in WO 98/13465, WO 98/015619, WO 98/015633, WO 99/06574, WO 99/10481, WO 99/025847, WO 99/031255, WO 2002/101078, WO 2003/027306, WO 2003/052054, WO 2003/052055, WO 2003/052056, WO 2003/052057, WO 2003/052118, WO 2004/016760, WO 2004/043980, WO 2004/048592, WO 2005/001065, WO 2005/028636, WO 2005/093050, WO 2005/093073, WO 2006/074005, WO 2006/117432, WO 2007/071818, WO 2007/071820, WO 2008/008070, WO 2008/008793, U.S. Pat. Nos. 5,457,046, 5,648,263, and 5,686,593.

In the methods of the present invention, any GH61 polypeptide having cellulolytic enhancing activity can be used.

In one aspect, the GH61 polypeptide having cellulolytic enhancing activity comprises the following motifs:

```
                           (SEQ ID NO: 25 or SEQ ID NO: 26)
[ILMV]-P-X(4,5)-G-X-Y-[ILMV]-X-R-X-[EQ]-X(4)-[HNQ]
and

[FW]-[TF]-K-[AIV],
``` wherein X is any amino acid, X(4,5) is any amino acid at 4 or 5 contiguous positions, and X(4) is any amino acid at 4 contiguous positions.

In another aspect, the isolated polypeptide comprising the above-noted motifs may further comprise:

```
                           (SEQ ID NO: 27 or SEQ ID NO: 28)
H-X(1,2)-G-P-X(3)-[YW]-[AILMV], (SEQ ID NO: 29)
[EQ]-X-Y-X(2)-C-X-[EHQN]-[FILV]-X-[ILV],
or (SEQ ID NO: 30 or SEQ ID NO: 31)
H-X(1,2)-G-P-X(3)-[YW]-[AILMV]
and (SEQ ID NO: 32)
[EQ]-X-Y-X(2)-C-X-[EHQN]-[FILV]-X-[ILV],
``` wherein X is any amino acid, X(1,2) is any amino acid at 1 position or 2 contiguous positions, X(3) is any amino acid at 3 contiguous positions, and X(2) is any amino acid at 2 contiguous positions. In the above motifs, the accepted IUPAC single letter amino acid abbreviation is employed.

In a preferred aspect, the isolated GH61 polypeptide having cellulolytic enhancing activity further comprises H-X(1,2)-G-P-X(3)-[YW]-[AILMV] (SEQ ID NO: 33 or SEQ ID NO: 34). In another preferred aspect, the isolated GH61 polypeptide having cellulolytic enhancing activity further comprises [EQ]X-Y-X(2)-C-X-[EHQN]-[FILV]-X-[ILV] (SEQ ID NO: 35). In another preferred aspect, the isolated GH61 polypeptide having cellulolytic enhancing activity further comprises H-X(1,2)-G-P-X(3)-[YW]-[AILMV] (SEQ ID NO: 36 or SEQ ID NO: 37) and [EQ]-X-Y-X(2)-C-X-[EHQN]-[FILV]-X-[ILV] (SEQ ID NO: 38).

In another, the isolated polypeptide having cellulolytic enhancing activity, comprises the following motif:

```
                           (SEQ ID NO: 39 or SEQ ID NO: 40)
[ILMV]-P-X(4,5)-G-X-Y-[ILMV]-X-R-X-[EQ]-X(3)-A-[HNQ],
``` wherein X is any amino acid, X(4,5) is any amino acid at 4 or 5 contiguous positions, and X(3) is any amino acid at 3 contiguous positions. In the above motif, the accepted IUPAC single letter amino acid abbreviation is employed.

Examples of GH61 polypeptides having cellulolytic enhancing activity useful in the processes of the present invention include, but are not limited to, GH61 polypeptides from *Thielavia terrestris* (WO 2005/074647, WO 2008/148131, and WO 2011/035027), *Thermoascus aurantiacus* (WO 2005/074656 and WO 2010/065830), *Trichoderma reesei* (WO 2007/089290), *Myceliophthora thermophila* (WO 2009/085935, WO 2009/085859, WO 2009/085864, WO 2009/085868), *Aspergillus fumigatus* (WO 2010/138754), GH61 polypeptides from *Penicillium pinophilum* (WO 2011/005867), *Thermoascus* sp. (WO 2011/039319), *Penicillium* sp. (WO 2011/041397), and *Thermoascus crustaceous* (WO 2011/041504).

In one aspect, the GH61 polypeptide having cellulolytic enhancing activity is used in the presence of a soluble activating divalent metal cation according to WO 2008/151043, e.g., manganese sulfate.

In one aspect, the GH61 polypeptide having cellulolytic enhancing activity is used in the presence of a dioxy compound, a bicylic compound, a heterocyclic compound, a nitrogen-containing compound, a quinone compound, a sulfur-containing compound, or a liquor obtained from a pretreated cellulosic material such as pretreated corn stover (PCS).

The dioxy compound may include any suitable compound containing two or more oxygen atoms. In some aspects, the dioxy compounds contain a substituted aryl moiety as described herein. The dioxy compounds may comprise one or more (e.g., several) hydroxyl and/or hydroxyl derivatives, but also include substituted aryl moieties lacking hydroxyl and hydroxyl derivatives. Non-limiting examples of the dioxy compounds include pyrocatechol or catechol; caffeic acid; 3,4-dihydroxybenzoic acid; 4-tert-butyl-5-methoxy-1,2-benzenediol; pyrogallol; gallic acid; methyl-3,4,5-trihydroxybenzoate; 2,3,4-trihydroxybenzophenone; 2,6-dimethoxyphenol; sinapinic acid; 3,5-dihydroxybenzoic acid; 4-chloro-1,2-benzenediol; 4-nitro-1,2-benzenediol; tannic acid; ethyl gallate; methyl glycolate; dihydroxyfumaric acid; 2-butyne-1,4-diol; (croconic acid; 1,3-propanediol; tartaric acid; 2,4-pentanediol; 3-ethyoxy-1,2-propanediol; 2,4,4'-trihydroxybenzophenone; cis-2-butene-1,4-diol; 3,4-dihydroxy-3-cyclobutene-1,2-dione; dihydroxyacetone; acrolein acetal; methyl-4-hydroxybenzoate; 4-hydroxybenzoic acid; and methyl-3,5-dimethoxy-4-hydroxybenzoate; or a salt or solvate thereof.

The bicyclic compound may include any suitable substituted fused ring system as described herein. The compounds may comprise one or more (e.g., several) additional rings, and are not limited to a specific number of rings unless otherwise stated. In one aspect, the bicyclic compound is a flavonoid. In another aspect, the bicyclic compound is an optionally substituted isoflavonoid. In another aspect, the bicyclic compound is an optionally substituted flavylium ion, such as an optionally substituted anthocyanidin or optionally substituted anthocyanin, or derivative thereof. Non-limiting examples of thebicyclic compounds include epicatechin; quercetin; myricetin; taxifolin; kaempferol; morin; acacetin; naringenin; isorhamnetin; apigenin; cyanidin; cyanin; kuromanin; keracyanin; or a salt or solvate thereof.

The heterocyclic compound may be any suitable compound, such as an optionally substituted aromatic or non-aromatic ring comprising a heteroatom, as described herein. In one aspect, the heterocyclic is a compound comprising an optionally substituted heterocycloalkyl moiety or an optionally substituted heteroaryl moiety. In another aspect, the optionally substituted heterocycloalkyl moiety or optionally substituted heteroaryl moiety is an optionally substituted 5-membered heterocycloalkyl or an optionally substituted 5-membered heteroaryl moiety. In another aspect, the optionally substituted heterocycloalkyl or optionally substituted heteroaryl moiety is an optionally substituted moiety selected from pyrazolyl, furanyl, imidazolyl, isoxazolyl, oxadiazolyl, oxazolyl, pyrrolyl, pyridyl, pyrimidyl, pyridazinyl, thiazolyl, triazolyl, thienyl, dihydrothieno-pyrazolyl, thianaphthenyl, carbazolyl, benzimidazolyl, benzothienyl, benzofuranyl, indolyl, quinolinyl, benzotriazolyl, benzothiazolyl, benzooxazolyl, benzimidazolyl, isoquinolinyl, isoindolyl, acridinyl, benzoisazolyl, dimethylhydantoin, pyrazinyl, tetrahydrofuranyl, pyrrolinyl, pyrrolidinyl, morpholinyl, indolyl, diazepinyl, azepinyl, thiepinyl, piperidinyl, and oxepinyl. In another aspect, the optionally substituted heterocycloalkyl moiety or optionally substituted heteroaryl moiety is an optionally substituted furanyl. Non-limiting examples of the heterocyclic compounds include (1,2-dihydroxyethyl)-3,4-dihydroxyfuran-2(5H)-one; 4-hydroxy-5-methyl-3-furanone; 5-hydroxy-2(5H)-furanone; [1,2-dihydroxyethyl]furan-2,3,4(5H)-trione; α-hydroxy-γ-butyrolactone; ribonic γ-lactone; aldohexuronicaldohexuronic acid γ-lactone; gluconic acid 5-lactone; 4-hydroxycoumarin; dihydrobenzofuran; 5-(hydroxymethyl)furfural; furoin; 2(5H)-furanone; 5,6-dihydro-2H-pyran-2-one; and 5,6-dihydro-4-hydroxy-6-methyl-2H-pyran-2-one; or a salt or solvate thereof.

The nitrogen-containing compound may be any suitable compound with one or more nitrogen atoms. In one aspect, the nitrogen-containing compound comprises an amine, imine, hydroxylamine, or nitroxide moiety. Non-limiting examples of thenitrogen-containing compounds include acetone oxime; violuric acid; pyridine-2-aldoxime; 2-aminophenol; 1,2-benzenediamine; 2,2,6,6-tetramethyl-1-piperidinyloxy; 5,6,7,8-tetrahydrobiopterin; 6,7-dimethyl-5,6,7,8-tetrahydropterine; and maleamic acid; or a salt or solvate thereof.

The quinone compound may be any suitable compound comprising a quinone moiety as described herein. Non-limiting examples of the quinone compounds include 1,4-benzoquinone; 1,4-naphthoquinone; 2-hydroxy-1,4-naphthoquinone; 2,3-dimethoxy-5-methyl-1,4-benzoquinone or coenzyme $Q_0$; 2,3,5,6-tetramethyl-1,4-benzoquinone or duroquinone; 1,4-dihydroxyanthraquinone; 3-hydroxy-1-methyl-5,6-indolinedione or adrenochrome; 4-tert-butyl-5-methoxy-1,2-benzoquinone; pyrroloquinoline quinone; or a salt or solvate thereof.

The sulfur-containing compound may be any suitable compound comprising one or more sulfur atoms. In one aspect, the sulfur-containing comprises a moiety selected from thionyl, thioether, sulfinyl, sulfonyl, sulfamide, sulfonamide, sulfonic acid, and sulfonic ester. Non-limiting examples of the sulfur-containing compounds include ethanethiol; 2-propanethiol; 2-propene-1-thiol; 2-mercaptoethanesulfonic acid; benzenethiol; benzene-1,2-dithiol; cysteine; methionine; glutathione; cystine; or a salt or solvate thereof.

In one aspect, an effective amount of such a compound described above to cellulosic material as a molar ratio to glucosyl units of cellulose is about $10^{-6}$ to about 10, e.g., about $10^{-6}$ to about 7.5, about $10^{-6}$ to about 5, about $10^{-6}$ to about 2.5, about $10^{-6}$ to about 1, about $10^{-5}$ to about 1, about $10^{-5}$ to about $10^{-1}$, about $10^{-4}$ to about $10^{-1}$, about $10^{-3}$ to about $10^{-1}$, or about $10^{-3}$ to about $10^{-2}$. In another aspect, an effective amount of such a compound described above is about 0.1 μM to about 1 M, e.g., about 0.5 μM to about 0.75 M, about 0.75 μM to about 0.5 M, about 1 μM to about 0.25 M, about 1 μM to about 0.1 M, about 5 μM to about 50 mM, about 10 µM to about 25 mM, about 50 µM to about 25 mM, about 10 µM to about 10 mM, about 5 µM to about 5 mM, or about 0.1 mM to about 1 mM.

The term "liquor" means the solution phase, either aqueous, organic, or a combination thereof, arising from treatment of a lignocellulose and/or hemicellulose material in a slurry, or monosaccharides thereof, e.g., xylose, arabinose, mannose, etc., under conditions as described herein, and the soluble contents thereof. A liquor for cellulolytic enhancement of a GH61 polypeptide can be produced by treating a lignocellulose or hemicellulose material (or feedstock) by applying heat and/or pressure, optionally in the presence of a catalyst, e.g., acid, optionally in the presence of an organic solvent, and optionally in combination with physical disruption of the material, and then separating the solution from the residual solids. Such conditions determine the degree of cellulolytic enhancement obtainable through the combination of liquor and a GH61 polypeptide during hydrolysis of a cellulosic substrate by a cellulase preparation. The liquor can be separated from the treated material using a method standard in the art, such as filtration, sedimentation, or centrifugation.

In one aspect, an effective amount of the liquor to cellulose is about $10^{-6}$ to about 10 g per g of cellulose, e.g., about $10^{-6}$ to about 7.5 g, about $10^{-6}$ to about 5, about $10^{-6}$ to about 2.5 g, about $10^{-6}$ to about 1 g, about $10^{-5}$ to about 1 g, about $10^{-5}$ to about $10^{-1}$ g, about $10^{-4}$ to about $10^{-1}$ g, about $10^{-3}$ to about $10^{-1}$ g, or about $10^{-3}$ to about $10^{-2}$ g per g of cellulose.

In one aspect, the one or more (e.g., several) hemicellulolytic enzymes comprise a commercial hemicellulolytic enzyme preparation. Examples of commercial hemicellulolytic enzyme preparations suitable for use in the present invention include, for example, SHEARZYME™ (Novozymes A/S), CELLIC® HTec (Novozymes A/S), CELLIC® HTec2 (Novozymes A/S), VISCOZYME® (Novozymes A/S), ULTRAFLO® (Novozymes A/S), PULPZYME® HC (Novozymes A/S), MULTIFECT® Xylanase (Genencor), ACCELLERASE® XY (Genencor), ACCELLERASE® XC (Genencor), ECOPULP® TX-200A (AB Enzymes), HSP 6000 Xylanase (DSM), DEPOL™ 333P (Biocatalysts Limit, Wales, UK), DEPOL™ 740L. (Biocatalysts Limit, Wales, UK), and DEPOL™ 762P (Biocatalysts Limit, Wales, UK).

Examples of xylanases useful in the processes of the present invention include, but are not limited to, xylanases from *Aspergillus aculeatus* (GeneSeqP:AAR63790; WO 94/21785), *Aspergillus fumigatus* (WO 2006/078256), *Penicillium* pinophilum (WO 2011/041405), *Penicillium* sp. (WO 2010/126772), *Thielavia terrestris* NRRL 8126 (WO 2009/079210), and *Trichophaea saccata* GH10 (WO 2011/057083).

Examples of beta-xylosidases useful in the processes of the present invention include, but are not limited to, beta-xylosidases from *Neurospora crassa* (SwissProt accession number Q7SOW4), *Trichoderma reesei* (UniProtKB/TrEMBL accession number Q92458), and *Talaromyces emersonii* (SwissProt accession number Q8×212).

Examples of acetylxylan esterases useful in the processes of the present invention include, but are not limited to, acetylxylan esterases from *Aspergillus aculeatus* (WO 2010/108918), *Chaetomium globosum* (Uniprot accession number Q2GWX4), *Chaetomium gracile* (GeneSeqP accession number AAB82124), *Humicola insolens* DSM 1800 (WO 2009/073709), *Hypocrea jecorina* (WO 2005/001036), *Myceliophtera thermophila* (WO 2010/014880), *Neurospora crassa* (UniProt accession number q7s259), *Phaeosphaeria nodorum* (Uniprot accession number Q0UHJ1), and *Thielavia terrestris* NRRL 8126 (WO 2009/042846).

Examples of feruloyl esterases (ferulic acid esterases) useful in the processes of the present invention include, but are not limited to, feruloyl esterases form *Humicola insolens* DSM 1800 (WO 2009/076122), *Neosartorya fischeri* (UniProt Accession number A1D9T4), *Neurospora crassa* (UniProt accession number Q9HGR3), *Penicillium aurantiogriseum* (WO 2009/127729), and *Thielavia terrestris* (WO 2010/053838 and WO 2010/065448).

Examples of arabinofuranosidases useful in the processes of the present invention include, but are not limited to, arabinofuranosidases from *Aspergillus niger* (GeneSeqP accession number AAR94170), *Humicola insolens* DSM 1800 (WO 2006/114094 and WO 2009/073383), and *M. giganteus* (WO 2006/114094).

Examples of alpha-glucuronidases useful in the processes of the present invention include, but are not limited to, alpha-glucuronidases from *Aspergillus clavatus* (UniProt accession number alcc12), *Aspergillus fumigatus* (SwissProt accession number Q4WW45), *Aspergillus niger* (Uniprot accession number Q96WX9), *Aspergillus terreus* (SwissProt accession number Q0CJP9), *Humicola insolens* (WO 2010/014706), *Penicillium aurantiogriseum* (WO 2009/068565), *Talaromyces emersonii* (UniProt accession number Q8×211), and *Trichoderma reesei* (Uniprot accession number Q99024).

The polypeptides having enzyme activity used in the processes of the present invention may be produced by fermentation of the above-noted microbial strains on a nutrient medium containing suitable carbon and nitrogen sources and inorganic salts, using procedures known in the art (see, e.g., Bennett, J. W. and LaSure, L. (eds.), *More Gene Manipulations in Fungi*, Academic Press, CA, 1991). Suitable media are available from commercial suppliers or may be prepared according to published compositions (e.g., in catalogues of the American Type Culture Collection). Temperature ranges and other conditions suitable for growth and enzyme production are known in the art (see, e.g., Bailey, J. E., and Ollis, D. F., *Biochemical Engineering Fundamentals*, McGraw-Hill Book Company, NY, 1986).

The fermentation can be any method of cultivation of a cell resulting in the expression or isolation of an enzyme or protein. Fermentation may, therefore, be understood as comprising shake flask cultivation, or small- or large-scale fermentation (including continuous, batch, fed-batch, or solid state fermentations) in laboratory or industrial fermentors performed in a suitable medium and under conditions allowing the enzyme to be expressed or isolated. The resulting enzymes produced by the methods described above may be recovered from the fermentation medium and purified by conventional procedures.

Fermentation.

The fermentable sugars obtained from the hydrolyzed cellulosic material or xylan-containing material can be fermented by one or more (e.g., several) fermenting microorganisms capable of fermenting the sugars directly or indirectly into a desired fermentation product. "Fermentation" or "fermentation process" refers to any fermentation process or any process comprising a fermentation step. Fermentation processes also include fermentation processes used in the consumable alcohol industry (e.g., beer and wine), dairy industry (e.g., fermented dairy products), leather industry, and tobacco industry. The fermentation conditions depend on the desired fermentation product and fermenting organism and can easily be determined by one skilled in the art.

In the fermentation step, sugars, released from the cellulosic material or xylan-containing material as a result of the pretreatment and enzymatic hydrolysis steps, are fermented to a product, e.g., ethanol, by a fermenting organism, such as yeast. Hydrolysis (saccharification) and fermentation can be separate or simultaneous, as described herein.

Any suitable hydrolyzed cellulosic material or xylan-containing material can be used in the fermentation step in practicing the present invention. The material is generally selected based on the desired fermentation product, i.e., the substance to be obtained from the fermentation, and the process employed, as is well known in the art.

The term "fermentation medium" is understood herein to refer to a medium before the fermenting microorganism(s) is(are) added, such as, a medium resulting from a saccharification process, as well as a medium used in a simultaneous saccharification and fermentation process (SSF).

"Fermenting microorganism" refers to any microorganism, including bacterial and fungal organisms, suitable for use in a desired fermentation process to produce a fermentation product. The fermenting organism can be hexose and/or pentose fermenting organisms, or a combination thereof. Both hexose and pentose fermenting organisms are well known in the art. Suitable fermenting microorganisms are able to ferment, i.e., convert, sugars, such as glucose, xylose, xylulose, arabinose, maltose, mannose, galactose, and/or oligosaccharides, directly or indirectly into the desired fermentation product. Examples of bacterial and fungal fermenting organisms producing ethanol are described by Lin et al., 2006, *Appl. Microbiol. Biotechnol.* 69: 627-642.

Examples of fermenting microorganisms that can ferment hexose sugars include bacterial and fungal organisms, such as yeast. Preferred yeast includes strains of *Candida*, *Kluyveromyces*, and *Saccharomyces*, e.g., *Candida sonorensis*, *Kluyveromyces marxianus*, and *Saccharomyces cerevisiae*.

Examples of fermenting organisms that can ferment pentose sugars in their native state include bacterial and fungal organisms, such as some yeast. Preferred xylose fermenting yeast include strains of *Candida*, preferably *C. sheatae* or *C. sonorensis*; and strains of *Pichia*, preferably *P. stipitis*, such as *P. stipitis* CBS 5773. Preferred pentose fermenting yeast include strains of *Pachysolen*, preferably *P. tannophilus*. Organisms not capable of fermenting pentose sugars, such as xylose and arabinose, may be genetically modified to do so by methods known in the art.

Examples of bacteria that can efficiently ferment hexose and pentose to ethanol include, for example, *Bacillus coagulans*, *Clostridium acetobutylicum*, *Clostridium thermocellum*, *Clostridium phytofermentans*, *Geobacillus* sp., *Thermoanaerobacter saccharolyticum*, and *Zymomonas mobilis* (Philippidis, 1996, supra).

Other fermenting organisms include strains of *Bacillus*, such as *Bacillus coagulans*; *Candida*, such as *C. sonorensis*, *C. methanosorbosa*, *C. diddensiae*, *C. parapsilosis*, *C. naedodendra*, *C. blankii*, *C. entomophilia*, *C. brassicae*, *C. pseudotropicalis*, *C. boidinii*, *C. utilis*, and *C. scehatae*; *Clostridium*, such as *C. acetobutylicum*, *C. thermocellum*, and *C. phytofermentans*; *E. coli*, especially *E. coli* strains that have been genetically modified to improve the yield of ethanol; *Geobacillus* sp.; *Hansenula*, such as *Hansenula anomala*; *Klebsiella*, such as *K. oxytoca*; *Kluyveromyces*, such as *K. marxianus*, *K. lactis*, *K. thermotolerans*, and *K. fragilis*; *Schizosaccharomyces*, such as *S. pombe*; *Thermoanaerobacter*, such as *Thermoanaerobacter saccharolyticum*; and *Zymomonas*, such as *Zymomonas mobilis*.

In a preferred aspect, the yeast is a *Bretannomyces*. In a more preferred aspect, the yeast is *Bretannomyces clausenii*. In another preferred aspect, the yeast is a *Candida*. In another more preferred aspect, the yeast is *Candida* sonorensis. In another more preferred aspect, the yeast is *Candida boidinii*. In another more preferred aspect, the yeast is *Candida blankii*. In another more preferred aspect, the yeast is *Candida brassicae*. In another more preferred aspect, the yeast is *Candida diddensii*. In another more preferred aspect, the yeast is *Candida entomophiliia*. In another more preferred aspect, the yeast is *Candida pseudotropicalis*. In another more preferred aspect, the yeast is *Candida scehatae*. In another more preferred aspect, the yeast is *Candida utilis*. In another preferred aspect, the yeast is a *Clavispora*. In another more preferred aspect, the yeast is *Clavispora lusitaniae*. In another more preferred aspect, the yeast is *Clavispora opuntiae*. In another preferred aspect, the yeast is a *Kluyveromyces*. In another more preferred aspect, the yeast is *Kluyveromyces fragilis*. In another more preferred aspect, the yeast is *Kluyveromyces marxianus*. In another more preferred aspect, the yeast is *Kluyveromyces thermotolerans*. In another preferred aspect, the yeast is a *Pachysolen*. In another more preferred aspect, the yeast is *Pachysolen tannophilus*. In another preferred aspect, the yeast is a *Pichia*. In another more preferred aspect, the yeast is a *Pichia stipitis*. In another preferred aspect, the yeast is a *Saccharomyces* spp. In a more preferred aspect, the yeast is *Saccharomyces cerevisiae*. In another more preferred aspect, the yeast is *Saccharomyces distaticus*. In another more preferred aspect, the yeast is *Saccharomyces uvarum*.

In a preferred aspect, the bacterium is a *Bacillus*. In a more preferred aspect, the bacterium is *Bacillus coagulans*. In another preferred aspect, the bacterium is a *Clostridium*. In another more preferred aspect, the bacterium is *Clostridium acetobutylicum*. In another more preferred aspect, the bacterium is *Clostridium phytofermentans*. In another more preferred aspect, the bacterium is *Clostridium thermocellum*. In another more preferred aspect, the bacterium is *Geobacilus* sp. In another more preferred aspect, the bacterium is a *Thermoanaerobacter*. In another more preferred aspect, the bacterium is *Thermoanaerobacter saccharolyticum*. In another preferred aspect, the bacterium is a *Zymomonas*. In another more preferred aspect, the bacterium is *Zymomonas mobilis*.

Commercially available yeast suitable for ethanol production include, e.g., BIOFERM™ AFT and XR (NABC—North American Bioproducts Corporation, GA, USA), ETHANOL RED™ yeast (Fermentis/Lesaffre, USA), FALI™ (Fleischmann's Yeast, USA), FERMIOL™ (DSM Specialties), GERT STRAND™ (Gert Strand AB, Sweden), and SUPERSTART™ and THERMOSACC™ fresh yeast (Ethanol Technology, WI, USA).

In a preferred aspect, the fermenting microorganism has been genetically modified to provide the ability to ferment pentose sugars, such as xylose utilizing, arabinose utilizing, and xylose and arabinose co-utilizing microorganisms.

The cloning of heterologous genes into various fermenting microorganisms has led to the construction of organisms capable of converting hexoses and pentoses to ethanol (co-fermentation) (Chen and Ho, 1993, Cloning and improving the expression of *Pichia stipitis* xylose reductase gene in *Saccharomyces cerevisiae*, *Appl. Biochem. Biotechnol.* 39-40: 135-147; Ho et al., 1998, Genetically engineered *Saccharomyces* yeast capable of effectively cofermenting glucose and xylose, *Appl. Environ. Microbiol.* 64: 1852-1859; Kotter and Ciriacy, 1993, Xylose fermentation by *Saccharomyces cerevisiae*, *Appl. Microbiol. Biotechnol.* 38: 776-783; Walfridsson et al., 1995, Xylose-metabolizing *Saccharomyces cerevisiae* strains overexpressing the TKL1 and TAL1 genes encoding the pentose phosphate pathway enzymes transketolase and transaldolase, *Appl. Environ. Microbiol.* 61: 4184-4190; Kuyper et al., 2004, Minimal metabolic engineering of *Saccharomyces cerevisiae* for efficient anaerobic xylose fermentation: a proof of principle, *FEMS Yeast Research* 4: 655-664; Beall et al., 1991, Parametric studies of ethanol production from xylose and other sugars by recombinant *Escherichia coli, Biotech. Bioeng.* 38: 296-303; Ingram et al., 1998, Metabolic engineering of bacteria for ethanol production, *Biotechnol. Bioeng.* 58: 204-214; Zhang et al., 1995, Metabolic engineering of a pentose metabolism pathway in ethanologenic *Zymomonas mobilis, Science* 267: 240-243; Deanda et al., 1996, Development of an arabinose-fermenting *Zymomonas mobilis* strain by metabolic pathway engineering, *Appl. Environ. Microbiol.* 62: 4465-4470; WO 2003/062430, xylose isomerase).

In a preferred aspect, the genetically modified fermenting microorganism is *Candida sonorensis*. In another preferred aspect, the genetically modified fermenting microorganism is *Escherichia coli*. In another preferred aspect, the genetically modified fermenting microorganism is *Klebsiella oxytoca*. In another preferred aspect, the genetically modified fermenting microorganism is *Kluyveromyces marxianus*. In another preferred aspect, the genetically modified fermenting microorganism is *Saccharomyces cerevisiae*. In another preferred aspect, the genetically modified fermenting microorganism is *Zymomonas mobilis*.

It is well known in the art that the organisms described above can also be used to produce other substances, as described herein.

The fermenting microorganism is typically added to the degraded cellulosic material or xylan-containing material or hydrolysate and the fermentation is performed for about 8 to about 96 hours, e.g., about 24 to about 60 hours. The temperature is typically between about 26° C. to about 60° C., e.g., about 32° C. or 50° C., and about pH 3 to about pH 8, e.g., pH 4-5, 6, or 7.

In one aspect, the yeast and/or another microorganism are applied to the degraded cellulosic material or xylan-containing material and the fermentation is performed for about 12 to about 96 hours, such as typically 24-60 hours. In another aspect, the temperature is preferably between about 20° C. to about 60° C., e.g., about 25° C. to about 50° C., about 32° C. to about 50° C., or about 32° C. to about 50° C., and the pH is generally from about pH 3 to about pH 7, e.g., about pH 4 to about pH 7. However, some fermenting organisms, e.g., bacteria, have higher fermentation temperature optima. Yeast or another microorganism is preferably applied in amounts of approximately $10^5$ to $10^{12}$, preferably from approximately $10^7$ to $10^{10}$, especially approximately $2 \times 10^8$ viable cell count per ml of fermentation broth. Further guidance in respect of using yeast for fermentation can be found in, e.g., "The Alcohol Textbook" (Editors K. Jacques, T. P. Lyons and D. R. Kelsall, Nottingham University Press, United Kingdom 1999), which is hereby incorporated by reference.

For ethanol production, following the fermentation the fermented slurry is distilled to extract the ethanol. The ethanol obtained according to the processes of the invention can be used as, e.g., fuel ethanol, drinking ethanol, i.e., potable neutral spirits, or industrial ethanol.

A fermentation stimulator can be used in combination with any of the processes described herein to further improve the fermentation process, and in particular, the performance of the fermenting microorganism, such as, rate enhancement and ethanol yield. A "fermentation stimulator" refers to stimulators for growth of the fermenting microorganisms, in particular, yeast. Preferred fermentation stimulators for growth include vitamins and minerals. Examples of vitamins include multivitamins, biotin, pantothenate, nicotinic acid, meso-inositol, thiamine, pyridoxine, para-aminobenzoic acid, folic acid, riboflavin, and Vitamins A, B, C, D, and E. See, for example, Alfenore et al., Improving ethanol production and viability of *Saccharomyces cerevisiae* by a vitamin feeding strategy during fed-batch process, Springer-Verlag (2002), which is hereby incorporated by reference. Examples of minerals include minerals and mineral salts that can supply nutrients comprising P, K, Mg, S, Ca, Fe, Zn, Mn, and Cu.

Fermentation Products:

A fermentation product can be any substance derived from the fermentation. The fermentation product can be, without limitation, an alcohol (e.g., arabinitol, n-butanol, isobutanol, ethanol, glycerol, methanol, ethylene glycol, 1,3-propanediol [propylene glycol], butanediol, glycerin, sorbitol, and xylitol); an alkane (e.g., pentane, hexane, heptane, octane, nonane, decane, undecane, and dodecane), a cycloalkane (e.g., cyclopentane, cyclohexane, cycloheptane, and cyclooctane), an alkene (e.g. pentene, hexene, heptene, and octene); an amino acid (e.g., aspartic acid, glutamic acid, glycine, lysine, serine, and threonine); a gas (e.g., methane, hydrogen ($H_2$), carbon dioxide ($CO_2$), and carbon monoxide (CO)); isoprene; a ketone (e.g., acetone); an organic acid (e.g., acetic acid, acetonic acid, adipic acid, ascorbic acid, citric acid, 2,5-diketo-D-gluconic acid, formic acid, fumaric acid, glucaric acid, gluconic acid, glucuronic acid, glutaric acid, 3-hydroxypropionic acid, itaconic acid, lactic acid, malic acid, malonic acid, oxalic acid, oxaloacetic acid, propionic acid, succinic acid, and xylonic acid); and polyketide. The fermentation product can also be protein as a high value product.

In a preferred aspect, the fermentation product is an alcohol. It will be understood that the term "alcohol" encompasses a substance that contains one or more hydroxyl moieties. In a more preferred aspect, the alcohol is n-butanol. In another more preferred aspect, the alcohol is isobutanol. In another more preferred aspect, the alcohol is ethanol. In another more preferred aspect, the alcohol is methanol. In another more preferred aspect, the alcohol is arabinitol. In another more preferred aspect, the alcohol is butanediol. In another more preferred aspect, the alcohol is ethylene glycol. In another more preferred aspect, the alcohol is glycerin. In another more preferred aspect, the alcohol is glycerol. In another more preferred aspect, the alcohol is 1,3-propanediol. In another more preferred aspect, the alcohol is sorbitol. In another more preferred aspect, the alcohol is xylitol. See, for example, Gong, C. S., Cao, N. J., Du, J., and Tsao, G. T., 1999, Ethanol production from renewable resources, in *Advances in Biochemical Engineering/Biotechnology*, Scheper, T., ed., Springer-Verlag Berlin Heidelberg, Germany, 65: 207-241; Silveira, M. M., and Jonas, R., 2002, The biotechnological production of sorbitol, *Appl. Microbiol. Biotechnol.* 59: 400-408; Nigam, P., and Singh, D., 1995, Processes for fermentative production of xylitol—a sugar substitute, *Process Biochemistry* 30 (2): 117-124; Ezeji, T. C., Qureshi, N. and Blaschek, H. P., 2003, Production of acetone, butanol and ethanol by *Clostridium beijerinckii* BA101 and in situ recovery by gas stripping, *World Journal of Microbiology and Biotechnology* 19 (6): 595-603.

In another preferred aspect, the fermentation product is an alkane. The alkane can be an unbranched or a branched alkane. In another more preferred aspect, the alkane is pentane. In another more preferred aspect, the alkane is hexane. In another more preferred aspect, the alkane is heptane. In another more preferred aspect, the alkane is octane. In another more preferred aspect, the alkane is nonane. In another more preferred aspect, the alkane is decane. In another more preferred aspect, the alkane is undecane. In another more preferred aspect, the alkane is dodecane.

In another preferred aspect, the fermentation product is a cycloalkane. In another more preferred aspect, the cycloalkane is cyclopentane. In another more preferred aspect, the cycloalkane is cyclohexane. In another more preferred aspect, the cycloalkane is cycloheptane. In another more preferred aspect, the cycloalkane is cyclooctane.

In another preferred aspect, the fermentation product is an alkene. The alkene can be an unbranched or a branched alkene. In another more preferred aspect, the alkene is pentene. In another more preferred aspect, the alkene is hexene. In another more preferred aspect, the alkene is heptene. In another more preferred aspect, the alkene is octene.

In another preferred aspect, the fermentation product is an amino acid. In another more preferred aspect, the organic acid is aspartic acid. In another more preferred aspect, the amino acid is glutamic acid. In another more preferred aspect, the amino acid is glycine.

In another more preferred aspect, the amino acid is lysine. In another more preferred aspect, the amino acid is serine. In another more preferred aspect, the amino acid is threonine. See, for example, Richard, A., and Margaritis, A., 2004, Empirical modeling of batch fermentation kinetics for poly (glutamic acid) production and other microbial biopolymers, *Biotechnology and Bioengineering* 87 (4): 501-515.

In another preferred aspect, the fermentation product is a gas. In another more preferred aspect, the gas is methane. In another more preferred aspect, the gas is $H_2$. In another more preferred aspect, the gas is $CO_2$. In another more preferred aspect, the gas is CO. See, for example, Kataoka, N., A. Miya, and K. Kiriyama, 1997, Studies on hydrogen production by continuous culture system of hydrogen-producing anaerobic bacteria, *Water Science and Technology* 36 (6-7): 41-47; and Gunaseelan V. N. in *Biomass and Bioenergy*, Vol. 13 (1-2), pp. 83-114, 1997, Anaerobic digestion of biomass for methane production: A review.

In another preferred aspect, the fermentation product is isoprene.

In another preferred aspect, the fermentation product is a ketone. It will be understood that the term "ketone" encompasses a substance that contains one or more ketone moieties. In another more preferred aspect, the ketone is acetone. See, for example, Qureshi and Blaschek, 2003, supra.

In another preferred aspect, the fermentation product is an organic acid. In another more preferred aspect, the organic acid is acetic acid. In another more preferred aspect, the organic acid is acetonic acid. In another more preferred aspect, the organic acid is adipic acid. In another more preferred aspect, the organic acid is ascorbic acid. In another more preferred aspect, the organic acid is citric acid. In another more preferred aspect, the organic acid is 2,5-diketo-D-gluconic acid. In another more preferred aspect, the organic acid is formic acid. In another more preferred aspect, the organic acid is fumaric acid. In another more preferred aspect, the organic acid is glucaric acid. In another more preferred aspect, the organic acid is gluconic acid. In another more preferred aspect, the organic acid is glucuronic acid. In another more preferred aspect, the organic acid is glutaric acid. In another preferred aspect, the organic acid is 3-hydroxypropionic acid. In another more preferred aspect, the organic acid is itaconic acid. In another more preferred aspect, the organic acid is lactic acid. In another more preferred aspect, the organic acid is malic acid. In another more preferred aspect, the organic acid is malonic acid. In another more preferred aspect, the organic acid is oxalic acid. In another more preferred aspect, the organic acid is propionic acid. In another more preferred aspect, the organic acid is succinic acid. In another more preferred aspect, the organic acid is xylonic acid. See, for example, Chen, R., and Lee, Y. Y., 1997, Membrane-mediated extractive fermentation for lactic acid production from cellulosic biomass, *Appl. Biochem. Biotechnol.* 63-65: 435-448.

In another preferred aspect, the fermentation product is polyketide.

Recovery.

The fermentation product(s) can be optionally recovered from the fermentation medium using any method known in the art including, but not limited to, chromatography, electrophoretic procedures, differential solubility, distillation, or extraction. For example, alcohol is separated from the fermented cellulosic material or xylan-containing material and purified by conventional methods of distillation. Ethanol with a purity of up to about 96 vol. % can be obtained, which can be used as, for example, fuel ethanol, drinking ethanol, i.e., potable neutral spirits, or industrial ethanol.

Signal Peptides

The present invention also relates to an isolated polynucleotide encoding a signal peptide comprising or consisting of amino acids 1 to 21 of SEQ ID NO: 2, amino acids 1 to 18 of SEQ ID NO: 4, amino acids 1 to 19 of SEQ ID NO: 6, amino acids 1 to 21 of SEQ ID NO: 8, amino acids 1 to 17 of SEQ ID NO: 10, or amino acids 1 to 17 of SEQ ID NO: 12. The polynucleotides may further comprise a gene encoding a protein, which is operably linked to the signal peptide. The protein is preferably foreign to the signal peptide.

The present invention also relates to nucleic acid constructs, expression vectors and recombinant host cells comprising such polynucleotides.

The present invention also relates to methods of producing a protein, comprising: (a) cultivating a recombinant host cell comprising such polynucleotide; and (b) recovering the protein.

The protein may be native or heterologous to a host cell. The term "protein" is not meant herein to refer to a specific length of the encoded product and, therefore, encompasses peptides, oligopeptides, and polypeptides. The term "protein" also encompasses two or more polypeptides combined to form the encoded product. The proteins also include hybrid polypeptides and fused polypeptides.

Preferably, the protein is a hormone or variant thereof, enzyme, receptor or portion thereof, antibody or portion thereof, or reporter. For example, the protein may be an oxidoreductase, transferase, hydrolase, lyase, isomerase, or ligase such as an aminopeptidase, amylase, carbohydrase, carboxypeptidase, catalase, cellulase, chitinase, cutinase, cyclodextrin glycosyltransferase, deoxyribonuclease, esterase, alpha-galactosidase, beta-galactosidase, glucoamylase, alpha-glucosidase, beta-glucosidase, invertase, laccase, another lipase, mannosidase, mutanase, oxidase, pectinolytic enzyme, peroxidase, phytase, polyphenoloxidase, proteolytic enzyme, ribonuclease, transglutaminase or xylanase.

The gene may be obtained from any prokaryotic, eukaryotic, or other source.

The present invention is further described by the following examples that should not be construed as limiting the scope of the invention.

EXAMPLES

Materials

Chemicals used as buffers and substrates were commercial products of at least reagent grade.

Strains

*Aspergillus aculeatus* CBS 172.66 was used as the source of polypeptides having having beta-glucosidase activity, beta-xylosidase activity, or beta-glucosidase and beta-xylosidase activity.

*Aspergillus oryzae* MT3568 strain was used for expression of the *A. aculeatus* genes encoding the polypeptides having beta-glucosidase activity, beta-xylosidase activity, or beta-glucosidase activity and beta-xylosidase activity. *A. oryzae* MT3568 is an amdS (acetamidase) disrupted gene derivative of *Aspergillus oryzae* JaL355 (WO 2002/40694) in which pyrG auxotrophy was restored by disrupting the *A. oryzae* acetamidase (amdS) gene with the pyrG gene.

Media and Solutions

YP+2% glucose medium was composed of 1% yeast extract, 2% peptone and 2% glucose.

YP+2% maltodextrin medium was composed of 1% yeast extract, 2% peptone and 2% maltodextrin.

PDA agar plates were composed of potato infusion (potato infusion was made by boiling 300 g of sliced (washed but unpeeled) potatoes in water for 30 minutes and then decanting or straining the broth through cheesecloth. Distilled water was then added until the total volume of the suspension was one liter, followed by 20 g of dextrose and 20 g of agar powder. The medium was sterilized by autoclaving at 15 psi for 15 minutes (Bacteriological Analytical Manual, 8th Edition, Revision A, 1998).

LB plates were composed of 10 g of Bacto-Tryptone, 5 g of yeast extract, 10 g of sodium chloride, 15 g of Bacto-agar, and deionized water to 1 liter.

LB medium was composed of 10 g of Bacto-Tryptone, 5 g of yeast extract, 10 g of sodium chloride, and deionized water to 1 liter.

COVE sucrose plates were composed of 342 g of sucrose, 20 g of agar powder, 20 ml of COVE salts solution, and deionized water to 1 liter. The medium was sterilized by autoclaving at 15 psi for 15 minutes (Bacteriological Analytical Manual, 8th Edition, Revision A, 1998). The medium was cooled to 60° C. and 10 mM acetamide, 15 mM CsCl, TRITON® X-100 (50 µl/500 ml) were added.

COVE salts solution was composed of 26 g of $MgSO_4.7H_2O$, 26 g of KCL, 26 g of $KH_2PO_4$, 50 ml of COVE trace metals solution, and deionized water to 1 liter.

COVE trace metals solution was composed of 0.04 g of $Na_2B_4O_7.10H_2O$, 0.4 g of $CuSO_4.5H_2O$, 1.2 g of $FeSO_4.7H_2O$, 0.7 g of $MnSO_4.H_2O$, 0.8 g of $Na_2MoO_4.2H_2O$, 10 g of $ZnSO_4.7H_2O$, and deionized water to 1 liter.

Example 1

Source of DNA Sequence Information for *Aspergillus aculeatus* CBS 172.66

Genomic sequence information was generated by the U.S. Department of Energy Joint Genome Institute (JGI). A preliminary assembly of the genome was downloaded from JGI and analyzed using the Pedant-Pro™ Sequence Analysis Suite (Biomax Informatics AG, Martinsried, Germany). Gene models constructed by the software were used as a starting point for detecting GH3 homologues in the genome. More precise gene models were constructed manually using multiple known GH3 protein sequences as a guide.

Example 2

*Aspergillus Aculeatus* CBS 172.66 Genomic DNA Extraction

*Aspergillus aculeatus* CBS 172.66 was propagated on PDA agar plates at 26° C. for 7 days. Spores harvested from the PDA plates were used to inoculate 25 ml of YP+2% glucose medium in a baffled shake flask and incubated at 26° C. for 48 hours with agitation at 200 rpm.

Genomic DNA was isolated according to a modified FASTDNA® SPIN protocol (Qbiogene, Inc., Carlsbad, Calif., USA). Briefly a FASTDNA® SPIN Kit for Soil (Qbiogene, Inc., Carlsbad, Calif., USA) was used in a FASTPREP® 24 Homogenization System (MP Biosciences, Santa Ana, Calif., USA). Two ml of fungal material from the above culture was harvested by centrifugation at 14,000×g for 2 minutes. The supernatant was removed and the pellet resuspended in 500 µl of deionized water. The suspension was transferred to a Lysing Matrix E FASTPREP® tube (Qbiogene, Inc., Carlsbad, Calif., USA) and 790 µl of sodium phosphate buffer and 100 µl of MT buffer from the FASTDNA® SPIN Kit were added to the tube. The sample was then secured in the FASTPREP® Instrument (Qbiogene, Inc., Carlsbad, Calif., USA) and processed for 60 seconds at a speed of 5.5 m/sec. The sample was then centrifuged at 14,000×g for two minutes and the supernatant transferred to a clean EPPENDORF® tube. A 250 µl volume of PPS reagent from the FASTDNA® SPIN Kit was added and then the sample was mixed gently by inversion. The sample was again centrifuged at 14,000×g for 5 minutes. The supernatant was transferred to a 15 ml tube followed by 1 ml of Binding Matrix suspension from the FASTDNA® SPIN Kit and then mixed by inversion for two minutes. The sample was placed in a stationary tube rack and the silica matrix was allowed to settle for 3 minutes. A 500 µl volume of the supernatant was removed and discarded and then the remaining sample was resuspended in the matrix. The sample was then transferred to a SPIN filter tube from the FASTDNA® SPIN Kit and centrifuged at 14,000×g for 1 minute. The catch tube was emptied and the remaining matrix suspension added to the SPIN filter tube. The sample was again centrifuged at 14,000×g for 1 minute. A 500 µl volume of SEWS-M solution from the FASTDNA® SPIN Kit was added to the SPIN filter tube and the sample was centrifuged at the same speed for 1 minute. The catch tube was emptied and the SPIN filter replaced in the catch tube. The unit was centrifuged at 14,000×g for 2 minutes to dry the matrix of residual SEWS-M wash solution. The SPIN filter was placed in a fresh catch tube and allowed to air dry for 5 minutes at room temperature. The matrix was gently resuspended in 100 µl of DES (DNase/Pyrogen free water) with a pipette tip. The unit was centrifuged at 14,000×g for 1 minute to elute the genomic DNA followed by elution with 100 µl of 0.1 mM EDTA-10 mM Tris pH 8.0 by centrifugation at 14,000×g for 1 minute and the eluates were combined. The concentration of the DNA harvested from the catch tube was measured at 260 nm with a UV spectrophotometer.

Example 3

Construction of *Aspergillus oryzae* Expression Vectors Containing *Aspergillus aculeatus* CBS 172.66 Genomic Sequences Encoding Family GH3 Polypeptides Having Beta-Glucosidase Activity, Beta-Xylosidase Activity, or Beta-Glucosidase and Beta-Xylosidase Activity Synthetic oligonucleotide primers shown below were designed to amplify by PCR *Aspergillus aculeatus* CBS 172.66 GH3 genes from the genomic DNA prepared in Example 2. An IN-FUSION® Cloning Kit (Clontech Laboratories, Inc., Mountain View, Calif., USA) was used to clone the fragments directly into the expression vector pDau109 (WO 2005/042735).

```
Primer GH3-202 f:
                                              (SEQ ID NO: 13)
5'-ACACAACTGGGGATCCACCATGACCCCCATCTGGCATTACCT-3'

Primer GH3-202r:
                                              (SEQ ID NO: 14)
5'-GGTGGATCCCCAGTTGTGTCTAGAGAACCTCACAAGCACCCCC-3'

Primer GH3-203f:
                                              (SEQ ID NO: 15)
5'-ACACAACTGGGGATCCACCATGAGATTCATTTCACTTGCC-3'

Primer GH3-203r:
                                              (SEQ ID NO: 16)
5'-AGATCTCGAGAAGCTTACTAAGCCTTCACTCTCAAAG-3'

Primer GH3-204f:
                                              (SEQ ID NO: 17)
5'-ACACAACTGGGGATCCACCATGCACAGCTTAGGATCC-3'

Primer GH3-204r:
                                              (SEQ ID NO: 18)
5'-AGATCTCGAGAAGCTTACTACACGGTCAACGTCAA-3'

Primer GH3-205f:
                                              (SEQ ID NO: 19)
5'-ACACAACTGGGGATCCACCATGGGTGCTAGTTTGCTAACCAA
GG-3'

Primer GH3-205r:
                                              (SEQ ID NO: 20)
5'-GGTGGATCCCCAGTTGTGTCTACTCAACATAGAACGTCGCATT
CCC-3'

Primer GH3-206f:
                                              (SEQ ID NO: 21)
5'-ACACAACTGGGGATCCACCATGAAGCTTACCGTTCCCTTAAC
GGC-3'

Primer GH3-206r:
                                              (SEQ ID NO: 22)
5'-GGTGGATCCCCAGTTGTGTCTAAAACGCCACCGACCCCG-3'

Primer GH3-114f:
                                              (SEQ ID NO: 23)
5'-ACACAACTGGGGATCCACCATGGCTGTGGCGGCTCTT-3'

Primer GH3-114r:
                                              (SEQ ID NO: 24)
5'-AGATCTCGAGAAGCTTACTACTCATCCCCCTGCAC-3'
```

PCR reactions were carried out with genomic DNA prepared from Example 2 for amplification of the genes identified in Example 1. The PCR reactions were composed of 1 µl of genomic DNA, 1 µl of primer forward (f) (50 µM); 1 µl of primer reverse (r) (50 µM); 10 µl of 5×HF buffer (Finnzymes Oy, Finland), 2 µl of 10 mM dNTP; 1 µl of PHUSION® DNA polymerase (Finnzymes Oy, Finland), and PCR-grade water up to 50 µl. Primers GH3-202f and GH3-202r were used simultaneously to amplify SEQ ID NO: 1; Primers GH3-203f and GH3-203r were used simultaneously to amplify SEQ ID NO: 3; Primers GH3-204f and GH3-204r were used simultaneously to amplify SEQ ID NO: 5; Primers GH3-205f and GH3-205r were used simultaneously to amplify SEQ ID NO: 7; Primers GH3-206f and GH3-206r were used simultaneously to amplify SEQ ID NO: 9; and Primers GH3-114f and GH3-114r were used simultaneously to amplify SEQ ID NO: 11.

The PCR reactions were performed using a DYAD PCR machine (Bio-Rad Laboratories, Inc., Hercules, Calif., USA) programmed for 2 minutes at 98° C. followed by 20 touch-down cycles at 98° C. for 15 seconds, 70° C. (−1° C./cycle) for 30 seconds, and 72° C. for 2 minutes 30 seconds; and 25 cycles each at 98° C. for 15 seconds, 60° C. for 30 seconds, 72° C. for 2 minutes 30 seconds; and 5 minutes at 72° C.

The reaction products were isolated by 1.0% agarose gel electrophoresis using 40 mM Tris base, 20 mM sodium acetate, 1 mM disodium EDTA (TAE) buffer where approximately 2.5 to 3.0 kb PCR product bands were excised from the gels and purified using a GFX® PCR DNA and Gel Band Purification Kit (GE Healthcare, United Kingdom) according to manufacturer's instructions. DNA corresponding to the A. aculeatus GH3 genes were cloned into the expression vector pDAu109 (WO 2005042735) linearized with Bam HI and Hind III, using an IN-FUSION™ Dry-Down PCR Cloning Kit (BD Biosciences, Palo Alto, Calif., USA) according to the manufacturer's instructions.

A 2.5 µl volume of each ligation mixture diluted 5-fold was used to transform E. coli TOP10 chemically competent cells (Invitrogen, Carlsbad, Calif., USA). Five colonies were selected on LB agar plates containing 100 µg of ampicillin per ml and cultivated overnight in 3 ml of LB medium supplemented with 100 µg of ampicillin per ml. Plasmid DNA was purified using an E.Z.N.A.® Plasmid Mini Kit (Omega Bio-Tek, Inc., Norcross, Ga., USA) according to the manufacturer's instructions. The Aspergillus aculeatus GH3 gene sequences were verified by Sanger sequencing with an Applied Biosystems Model 3700 Automated DNA Sequencer using version 3.1 BIG-DYE™ terminator chemistry (Applied Biosystems, Inc., Foster City, Calif., USA) (Applied Biosystems, Inc., Foster City, Calif., USA). Nucleotide sequence data were scrutinized for quality and all sequences were compared to each other with assistance of PHRED/PHRAP software (University of Washington, Seattle, Wash., USA).

Six plasmids designated as IF250#1 (SEQ ID NO: 1), IF233#1 (SEQ ID NO: 3), IF234#1 (SEQ ID NO: 5), IF235#1 (SEQ ID NO: 7), IF244#14 (SEQ ID NO: 9), and IF245#1 (SEQ ID NO: 11) were selected for heterologous expression in A. oryzae MT3568.

Example 4

Characterization of Aspergillus aculeatus CBS 172.66 Genomic Sequences Encoding GH3 Polypeptides Having Beta-Glucosidase Activity, Beta-Xylosidase Activity, or Beta-Glucosidase and Beta-Xylosidase Activity The nucleotide sequence and deduced amino acid sequence of a Aspergillus aculeatus GH3 gene are shown in SEQ ID NO: 1 and SEQ ID NO: 2, respectively. The coding sequence is 2710 bp including the stop codon and is interrupted by introns of 82 bp (nucleotides 176 to 257), 50 bp (nucleotides 755 to 804), 49 bp (nucleotides 1057 to 1105), 50 bp (nucleotides 1363 to 1412), 44 bp (nucleotides 1980 to 2023), and 86 bp (nucleotides 2193 to 2278). The encoded predicted protein is 782 amino acids. Using the SignalP program (Nielsen et al., 1997, Protein Engineering 10:1-6), a signal peptide of 21 residues was predicted. The predicted mature protein contains 761 amino acids.

A comparative pairwise global alignment of amino acid sequences was determined using the Needleman and Wunsch algorithm (Needleman and Wunsch, 1970, J. Mol. Biol. 48: 443-453) with gap open penalty of 10, gap extension penalty of 0.5, and the EBLOSUM62 matrix. The alignment showed that the deduced amino acid sequence of the Aspergillus aculeatus gene encoding the GH3 polypeptide having beta-glucosidase activity, beta-xylosidase activity, or beta-glucosidase and beta-xylosidase activity shares 72.04% identity (excluding gaps) to the deduced amino acid sequence of a GH3 family putative beta-glucosidase from *Neosartorya fischeri* (accession number SWISSPROT:A1DMR8).

The nucleotide sequence and deduced amino acid sequence of the *Aspergillus aculeatus* GH3 gene are shown in SEQ ID NO: 3 and SEQ ID NO: 4, respectively. The coding sequence is 2560 bp including the stop codon and is interrupted by introns of 55 bp (nucleotides 95 to 149), 62 bp (nucleotides 584 to 645), 47 bp (nucleotides 1908 to 1954), and 65 bp (nucleotides 2005 to 2069). The encoded predicted protein is 776 amino acids. Using the SignalP program (Nielsen et al., 1997, supra), a signal peptide of 18 residues was predicted. The predicted mature protein contains 758 amino acids.

A comparative pairwise global alignment of amino acid sequences was determined using the Needleman and Wunsch algorithm (Needleman and Wunsch, 1970, supra) with gap open penalty of 10, gap extension penalty of 0.5, and the EBLOSUM62 matrix. The alignment showed that the deduced amino acid sequence of the *Aspergillus aculeatus* gene encoding the GH3 polypeptide having beta-glucosidase activity, beta-xylosidase activity, or beta-glucosidase and beta-xylosidase activity shares 82.6% identity (excluding gaps) to the deduced amino acid sequence of a beta-glucosidase from *Aspergillus flavus* (accession number SWISSPROT:B8NJF4).

The nucleotide sequence and deduced amino acid sequence of the *Aspergillus aculeatus* GH3 gene are shown in SEQ ID NO: 5 and SEQ ID NO: 6, respectively. The coding sequence is 2633 bp including the stop codon and is interrupted by introns of 55 bp (nucleotides 128 to 182), 52 bp (nucleotides 377 to 428), 60 bp (nucleotides 482 to 541), 61 bp (nucleotides 765 to 825), 51 bp (nucleotides 1073 to 1123), and 47 bp (nucleotides 1287 to 1333). The encoded predicted protein is 768 amino acids. Using the SignalP program (Nielsen et al., 1997, supra), a signal peptide of 19 residues was predicted. The predicted mature protein contains 749 amino acids.

A comparative pairwise global alignment of amino acid sequences was determined using the Needleman and Wunsch algorithm (Needleman and Wunsch, 1970, supra) with gap open penalty of 10, gap extension penalty of 0.5, and the EBLOSUM62 matrix. The alignment showed that the deduced amino acid sequence of the *Aspergillus aculeatus* gene encoding the GH3 polypeptide having beta-glucosidase activity, beta-xylosidase activity, or beta-glucosidase and beta-xylosidase activity shares 79.8% identity (excluding gaps) to the deduced amino acid sequence of a beta-glucosidase from *Aspergillus niger* (accession number SWISSPROT:A5ABF5).

The nucleotide sequence and deduced amino acid sequence of the *Aspergillus aculeatus* GH3 gene are shown in SEQ ID NO: 7 and SEQ ID NO: 8, respectively. The coding sequence is 2346 bp including the stop codon and contains no introns. The encoded predicted protein is 781 amino acids. Using the SignalP program (Nielsen et al., 1997, supra), a signal peptide of 21 residues was predicted. The predicted mature protein contains 760 amino acids.

A comparative pairwise global alignment of amino acid sequences was determined using the Needleman and Wunsch algorithm (Needleman and Wunsch, 1970, supra) with gap open penalty of 10, gap extension penalty of 0.5, and the EBLOSUM62 matrix. The alignment showed that the deduced amino acid sequence of the *Aspergillus aculeatus* gene encoding the GH3 polypeptide having beta-glucosidase activity, beta-xylosidase activity, or beta-glucosidase and beta-xylosidase activity shares 79.2% identity (excluding gaps) to the deduced amino acid sequence of a GH3 protein from *Aspergillus niger* (accession number SWISSPROT:A2R967).

The nucleotide sequence and deduced amino acid sequence of the *Aspergillus* aculeatus GH3 gene are shown in SEQ ID NO: 9 and SEQ ID NO: 10, respectively. The coding sequence is 2436 bp including the stop codon and contains no introns. The encoded predicted protein is 811 amino acids. Using the SignalP program (Nielsen et al., 1997, supra), a signal peptide of 17 residues was predicted. The predicted mature protein contains 794 amino acids.

A comparative pairwise global alignment of amino acid sequences was determined using the Needleman and Wunsch algorithm (Needleman and Wunsch, 1970, supra) with gap open penalty of 10, gap extension penalty of 0.5, and the EBLOSUM62 matrix. The alignment showed that the deduced amino acid sequence of the *Aspergillus aculeatus* gene encoding the GH3 polypeptide having beta-glucosidase activity, beta-xylosidase activity, or beta-glucosidase and beta-xylosidase activity 76.8% identity (excluding gaps) to the deduced amino acid sequence of a GH3 protein from *Aspergillus oryzae* (accession number GENESEQP:AEX89463).

The nucleotide sequence and deduced amino acid sequence of the *Aspergillus aculeatus* GH3 gene are shown in SEQ ID NO: 11 and SEQ ID NO: 12, respectively. The coding sequence is 2412 bp including the stop codon and contains no introns. The encoded predicted protein is 803 amino acids. Using the SignalP program (Nielsen et al., 1997, supra), a signal peptide of 17 residues was predicted. The predicted mature protein contains 786 amino acids.

A comparative pairwise global alignment of amino acid sequences was determined using the Needleman and Wunsch algorithm (Needleman and Wunsch, 1970, supra) with gap open penalty of 10, gap extension penalty of 0.5, and the EBLOSUM62 matrix. The alignment showed that the deduced amino acid sequence of the *Aspergillus aculeatus* gene encoding the GH3 polypeptide having beta-glucosidase activity, beta-xylosidase activity, or beta-glucosidase and beta-xylosidase activity shares 71.4% identity (excluding gaps) to the deduced amino acid sequence of a plant degrading enzyme (accession number GENESEQP:AXR37967).

Example 5

Transformation of *Aspergillus oryzae* with Genes Encoding Polypeptides Having Beta-Glucosidase Activity, Beta-Xylosidase Activity, or Beta-Glucosidase and Beta-Xylosidase Activity from *Aspergillus aculeatus*

Protoplasts of *Aspergillus oryzae* MT3568 were prepared according to WO 95/002043. One hundred µl of protoplasts were mixed with 2.5-15 µg of the *Aspergillus* expression vectors IF250#1, IF233#1, IF234#1, IF235#1, IF244#14, IF245#1 (Example 3) and 250 µl of 60% PEG 4000 (Applichem, Darmstadt, Germany) (polyethylene glycol, molecular weight 4,000), 10 mM $CaCl_2$, and 10 mM Tris-HCl pH 7.5 and gently mixed. The mixture was incubated at 37° C. for 30 minutes and the protoplasts were spread onto COVE plates for selection. After incubation for 4-7 days at 37° C. spores of eight transformants were inoculated into 0.5 ml of YP medium supplemented with 2% maltodextrin in 96 deep well plates. After 4 days cultivation at 30° C., the culture broths were analyzed by SDS-PAGE to identify the transformants producing the largest amount of recombinant proteins from *Aspergillus aculeatus*.

Spores of the best transformants were spread on COVE sucrose plates in order to isolate single colonies. The spreading was repeated twice in total on COVE plates containing 10 mM sodium nitrate.

The present invention is described by the following numbered paragraphs:

[1] An isolated polypeptide having beta-glucosidase activity, beta-xylosidase activity, or beta-glucosidase and beta-xylosidase activity, selected from the group consisting of: (a) a polypeptide having at least 75% sequence identity to the mature polypeptide of SEQ ID NO: 2 or SEQ ID NO: 12; at least 80% sequence identity to the mature polypeptide of SEQ ID NO: 6, SEQ ID NO: 8, or SEQ ID NO: 10; or at least 85% sequence identity to the mature polypeptide of SEQ ID NO: 4; (b) a polypeptide encoded by a polynucleotide that hybridizes under at least high stringency conditions with (i) the mature polypeptide coding sequence of SEQ ID NO: 1 or the cDNA sequence thereof, SEQ ID NO: 3 or the cDNA sequence thereof, SEQ ID NO: 5 or the cDNA sequence thereof, SEQ ID NO: 7, SEQ ID NO: 9, or SEQ ID NO: 11, or (ii) the full-length complement of (i); (c) a polypeptide encoded by a polynucleotide having at least 75% sequence identity to the mature polypeptide coding sequence of SEQ ID NO: 1, or the cDNA sequence thereof, or SEQ ID NO: 11; at least 80% sequence identity to the mature polypeptide coding sequence of SEQ ID NO: 5 or the cDNA sequence thereof, SEQ ID NO: 7, or SEQ ID NO: 9; or at least 85% sequence identity to the mature polypeptide coding sequence of SEQ ID NO: 3 or the cDNA sequence thereof; (d) a variant of the mature polypeptide of SEQ ID NO: 2, SEQ ID NO: 4, SEQ ID NO: 6, SEQ ID NO: 8, SEQ ID NO: 10, or SEQ ID NO: 12 comprising a substitution, deletion, and/or insertion at one or more (e.g., several) positions; and (e) a fragment of the polypeptide of (a), (b), (c), or (d) that has beta-glucosidase activity, beta-xylosidase activity, or beta-glucosidase and beta-xylosidase activity.

[2] The polypeptide of paragraph 1, having at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to the mature polypeptide of SEQ ID NO: 2 or SEQ ID NO: 12; at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to the mature polypeptide of SEQ ID NO: 6, SEQ ID NO: 8, or SEQ ID NO: 10; or at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to the mature polypeptide of SEQ ID NO: 4.

[3] The polypeptide of paragraph 1 or 2, which is encoded by a polynucleotide that hybridizes under high or very high stringency conditions with (i) the mature polypeptide coding sequence of SEQ ID NO: 1 or the cDNA sequence thereof, SEQ ID NO: 3 or the cDNA sequence thereof, SEQ ID NO: 5 or the cDNA sequence thereof, SEQ ID NO: 7, SEQ ID NO: 9, or SEQ ID NO: 11, or (ii) the full-length complement of (i).

[4] The polypeptide of any of paragraphs 1-3, which is encoded by a polynucleotide having at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to the mature polypeptide coding sequence of SEQ ID NO: 1, or the cDNA sequence thereof, or SEQ ID NO: 11; at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to the mature polypeptide coding sequence of SEQ ID NO: 5, or the cDNA sequence thereof, SEQ ID NO: 7, or SEQ ID NO: 9; or at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to the mature polypeptide coding sequence of SEQ ID NO: 3 or the cDNA sequence thereof.

[5] The polypeptide of any of paragraphs 1-4, comprising or consisting of SEQ ID NO: 2, SEQ ID NO: 4, SEQ ID NO: 6, SEQ ID NO: 8, SEQ ID NO: 10, or SEQ ID NO: 12; or the mature polypeptide thereof.

[6] The polypeptide of paragraph 5, wherein the mature polypeptide is amino acids 22 to 782 of SEQ ID NO: 2, amino acids 19 to 776 of SEQ ID NO: 4, amino acids 20 to 768 of SEQ ID NO: 6, amino acids 22 to 781 of SEQ ID NO: 8, amino acids 18 to 811 of SEQ ID NO: 10, or amino acids 18 to 803 of SEQ ID NO: 12.

[7] The polypeptide of any of paragraphs 1-4, which is a variant of the mature polypeptide of SEQ ID NO: 2, SEQ ID NO: 4, SEQ ID NO: 6, SEQ ID NO: 8, SEQ ID NO: 10, or SEQ ID NO: 12 comprising a substitution, deletion, and/or insertion at one or more positions.

[8] The polypeptide of paragraph 1, which is a fragment of SEQ ID NO: 2, SEQ ID NO: 4, SEQ ID NO: 6, SEQ ID NO: 8, SEQ ID NO: 10, or SEQ ID NO: 12, wherein the fragment has beta-glucosidase activity, beta-xylosidase activity, or beta-glucosidase and beta-xylosidase activity.

[9] A composition comprising the polypeptide of any of paragraphs 1-8.

[10] An isolated polynucleotide encoding the polypeptide of any of paragraphs 1-8.

[11] A nucleic acid construct or expression vector comprising the polynucleotide of paragraph 10 operably linked to one or more control sequences that direct the production of the polypeptide in an expression host.

[12] A recombinant host cell comprising the polynucleotide of paragraph 10 operably linked to one or more control sequences that direct the production of the polypeptide.

[13] A method of producing the polypeptide of any of paragraphs 1-8, comprising: (a) cultivating a cell, which in its wild-type form produces the polypeptide, under conditions conducive for production of the polypeptide; and (b) recovering the polypeptide.

[14] A method of producing a polypeptide having beta-glucosidase activity, beta-xylosidase activity, or beta-glucosidase and beta-xylosidase activity, comprising: (a) cultivating the host cell of paragraph 12 under conditions conducive for production of the polypeptide; and (b) recovering the polypeptide.

[15] A transgenic plant, plant part or plant cell transformed with a polynucleotide encoding the polypeptide of any of paragraphs 1-8.

[16] A method of producing a polypeptide having beta-glucosidase activity, beta-xylosidase activity, or beta-glucosidase and beta-xylosidase activity, comprising: (a) cultivating the transgenic plant or plant cell of paragraph 15 under conditions conducive for production of the polypeptide; and (b) recovering the polypeptide.

[17] A method of producing a mutant of a parent cell, comprising inactivating a polynucleotide encoding the polypeptide of any of paragraphs 1-8, which results in the mutant producing less of the polypeptide than the parent cell.

[18] A mutant cell produced by the method of paragraph 17.

[19] The mutant cell of paragraph 18, further comprising a gene encoding a native or heterologous protein.

[20] A method of producing a protein, comprising: (a) cultivating the mutant cell of paragraph 18 or 19 under conditions conducive for production of the protein; and (b) recovering the protein.

[21] A double-stranded inhibitory RNA (dsRNA) molecule comprising a subsequence of the polynucleotide of paragraph 10, wherein optionally the dsRNA is an siRNA or an miRNA molecule.

[22] The double-stranded inhibitory RNA (dsRNA) molecule of paragraph 21, which is about 15, 16, 17, 18, 19, 20, 21, 22, 23, 24, 25 or more duplex nucleotides in length.

[23] A method of inhibiting the expression of a polypeptide having beta-glucosidase activity, beta-xylosidase activity, or beta-glucosidase and beta-xylosidase activity in a cell, comprising administering to the cell or expressing in the cell the double-stranded inhibitory RNA (dsRNA) molecule of paragraph 21 or 22.

[24] A cell produced by the method of paragraph 23.

[25] The cell of paragraph 24, further comprising a gene encoding a native or heterologous protein.

[26] A method of producing a protein, comprising: (a) cultivating the cell of paragraph 24 or 25 under conditions conducive for production of the protein; and (b) recovering the protein.

[27] An isolated polynucleotide encoding a signal peptide comprising or consisting of amino acids 1 to 21 of SEQ ID NO: 2, amino acids 1 to 18 of SEQ ID NO: 4, amino acids 1 to 19 of SEQ ID NO: 6, amino acids 1 to 21 of SEQ ID NO: 8, amino acids 1 to 17 of SEQ ID NO: 10, or amino acids 1 to 17 of SEQ ID NO: 12.

[28] A nucleic acid construct or expression vector comprising a gene encoding a protein operably linked to the polynucleotide of paragraph 27, wherein the gene is foreign to the polynucleotide encoding the signal peptide.

[29] A recombinant host cell comprising a gene encoding a protein operably linked to the polynucleotide of paragraph 27, wherein the gene is foreign to the polynucleotide encoding the signal peptide.

[30] A process of producing a protein, comprising: (a) cultivating a recombinant host cell comprising a gene encoding a protein operably linked to the polynucleotide of paragraph 27, wherein the gene is foreign to the polynucleotide encoding the signal peptide, under conditions conducive for production of the protein; and (b) recovering the protein.

[31] A whole broth formulation or cell culture composition comprising the polypeptide of any of paragraphs 1-8.

[32] A process for degrading or converting a cellulosic material or xylan-containing material, comprising: treating the cellulosic material or xylan-containing material with an enzyme composition in the presence of the polypeptide having beta-glucosidase activity, beta-xylosidase activity, or beta-glucosidase and beta-xylosidase activity of any of paragraphs 1-8.

[33] The process of paragraph 32, wherein the cellulosic material or xylan-containing material is pretreated.

[34] The process of paragraph 32 or 33, wherein the enzyme composition comprises one or more enzymes selected from the group consisting of a cellulase, a GH61 polypeptide having cellulolytic enhancing activity, a hemicellulase, an esterase, an expansin, a laccase, a ligninolytic enzyme, a pectinase, a peroxidase, a protease, and a swollenin.

[35] The process of paragraph 34, wherein the cellulase is one or more enzymes selected from the group consisting of an endoglucanase, a cellobiohydrolase, and a beta-glucosidase.

[36] The process of paragraph 34, wherein the hemicellulase is one or more enzymes selected from the group consisting of a xylanase, an acetylxylan esterase, a feruloyl esterase, an arabinofuranosidase, a xylosidase, and a glucuronidase.

[37] The process of any of paragraphs 32-36, further comprising recovering the degraded cellulosic material or xylan-containing material.

[38] The process of paragraph 37, wherein the degraded cellulosic material or xylan-containing material is a sugar.

[39] The process of paragraph 38, wherein the sugar is selected from the group consisting of glucose, xylose, mannose, galactose, and arabinose.

[40] A process for producing a fermentation product, comprising: (a) saccharifying a cellulosic material or xylan-containing material with an enzyme composition in the presence of the polypeptide having beta-glucosidase activity, beta-xylosidase activity, or beta-glucosidase and beta-xylosidase activity of any of paragraphs 1-8; (b) fermenting the saccharified cellulosic material or xylan-containing material with one or more fermenting microorganisms to produce the fermentation product; and (c) recovering the fermentation product from the fermentation.

[41] The process of paragraph 40, wherein the cellulosic material or xylan-containing material is pretreated.

[42] The process of paragraph 40 or 41, wherein the enzyme composition comprises one or more enzymes selected from the group consisting of a cellulase, a GH61 polypeptide having cellulolytic enhancing activity, a hemicellulase, an esterase, an expansin, a laccase, a ligninolytic enzyme, a pectinase, a peroxidase, a protease, and a swollenin.

[43] The process of paragraph 42, wherein the cellulase is one or more enzymes selected from the group consisting of an endoglucanase, a cellobiohydrolase, and a beta-glucosidase.

[44] The process of paragraph 42, wherein the hemicellulase is one or more enzymes selected from the group consisting of a xylanase, an acetylxylan esterase, a feruloyl esterase, an arabinofuranosidase, a xylosidase, and a glucuronidase.

[45] The process of any of paragraphs 40-44, wherein steps (a) and (b) are performed simultaneously in a simultaneous saccharification and fermentation.

[46] The process of any of paragraphs 40-45, wherein the fermentation product is an alcohol, an alkane, a cycloalkane, an alkene, an amino acid, a gas, isoprene, a ketone, an organic acid, or polyketide.

[47] A process of fermenting a cellulosic material or xylan-containing material, comprising: fermenting the cellulosic material or xylan-containing material with one or more fermenting microorganisms, wherein the cellulosic material or xylan-containing material is saccharified with an enzyme composition in the presence of a polypeptide having beta-glucosidase activity, beta-xylosidase activity, or beta-glucosidase and beta-xylosidase activity of any of paragraphs 1-8.

[48] The process of paragraph 47, wherein the fermenting of the cellulosic material or xylan-containing material produces a fermentation product.

[49] The process of paragraph 48, further comprising recovering the fermentation product from the fermentation.

[50] The process of any of paragraphs 47-49, wherein the cellulosic material or xylan-containing material is pretreated before saccharification.

[51] The process of any of paragraphs 47-50, wherein the enzyme composition comprises one or more enzymes selected from the group consisting of a cellulase, a GH61 polypeptide having cellulolytic enhancing activity, a hemicellulase, an esterase, an expansin, a laccase, a ligninolytic enzyme, a pectinase, a peroxidase, a protease, and a swollenin.

[52] The process of paragraph 51, wherein the cellulase is one or more enzymes selected from the group consisting of an endoglucanase, a cellobiohydrolase, and a beta-glucosidase.

[53] The process of paragraph 51, wherein the hemicellulase is one or more enzymes selected from the group consisting of a xylanase, an acetylxylan esterase, a feruloyl esterase, an arabinofuranosidase, a xylosidase, and a glucuronidase.

[54] The process of any of paragraphs 47-53, wherein the fermentation product is an alcohol, an alkane, a cycloalkane, an alkene, an amino acid, a gas, isoprene, a ketone, an organic acid, or polyketide.

The invention described and claimed herein is not to be limited in scope by the specific aspects herein disclosed, since these aspects are intended as illustrations of several aspects of the invention. Any equivalent aspects are intended to be within the scope of this invention. Indeed, various modifications of the invention in addition to those shown and described herein will become apparent to those skilled in the art from the foregoing description. Such modifications are also intended to fall within the scope of the appended claims. In the case of conflict, the present disclosure including definitions will control.

What is claimed is:

1. An isolated polypeptide having beta-glucosidase activity, selected from the group consisting of:
   (a) a polypeptide having at least 95% sequence identity to amino acids 22 to 782 of SEQ ID NO: 2;
   (b) a polypeptide encoded by a polynucleotide that hybridizes under at least very high stringency conditions with (i) nucleotides 64 to 2707 of SEQ ID NO: 1 or a cDNA sequence thereof, or (ii) the full-length complement of (i), wherein very high stringency conditions are defined as prehybridization and hybridization at 42° C. in 5X SSPE, 0.3% SDS, 200 μg/ml sheared and denatured salmon sperm DNA, and 50% formamide and washing three times each for 15 minutes using 2X SSC, 0.2% SDS at 70° C.;
   (c) a polypeptide encoded by a polynucleotide having at least 99% sequence identity to nucleotides 64 to 2707 of SEQ ID NO: 1 or a cDNA sequence thereof and (d) an isolated fragment of the polypeptide of (a), (b), (c), or (d) that has beta-glucosidase activity.

2. A nucleic acid construct comprising an isolated polynucleotide encoding the polypeptide of claim 1, wherein the polynucleotide is operably linked to one or more heterologous control sequences that direct the production of the polypeptide in an expression host.

3. A recombinant host cell comprising an isolated polynucleotide comprising a nucleotide sequence that encodes the polypeptide of claim 1.

4. A method of producing the polypeptide of claim 1, said method comprising:
    (a) cultivating an isolated *Aspergillus aculeatus* cell under conditions conducive for production of the polypeptide; and
    (b) recovering the polypeptide.

5. A method of producing the polypeptide having beta-glucosidase activity of claim 1, said method comprising:
    (a) cultivating a host cell comprising an isolated polynucleotide encoding the polypeptide under conditions conducive for production of the polypeptide; and
    (b) recovering the polypeptide.

6. A transgenic plant, plant part or plant cell transformed with an isolated polynucleotide encoding the polypeptide of claim 1, wherein the polypeptide comprises a signal peptide directing the polypeptide into the secretory pathway.

7. A method of producing a polypeptide having beta-glucosidase activity, said method comprising:
    (a) cultivating the transgenic plant or plant cell of claim 6 under conditions conducive for production of the polypeptide; and
    (b) recovering the polypeptide.

8. A nucleic acid construct comprising a heterologous nucleic acid operably linked to an isolated polynucleotide encoding a signal peptide comprising or consisting of amino acids 1 to 21 of SEQ ID NO: 2.

9. A recombinant host cell comprising a nucleic acid encoding a protein, wherein the nucleic acid is operably linked to an isolated polynucleotide encoding a signal peptide comprising or consisting of amino acids 1 to 21 of SEQ ID NO: 2, wherein the nucleic acid is foreign to the polynucleotide encoding the signal peptide.

10. A process of producing a protein, said process comprising:
    (a) cultivating the recombinant host cell of claim 9 under conditions conducive for production of the protein; and
    (b) recovering the protein.

11. A whole broth formulation or cell culture composition comprising the polypeptide of claim 1.

12. A process for degrading a cellulosic material or xylan-containing material, said process comprising: treating the cellulosic material or xylan-containing material with an enzyme composition in the presence of the polypeptide having beta-glucosidase activity of claim 1.

13. The process of claim 12, further comprising recovering the degraded cellulosic material or xylan-containing material.

14. A process for producing a fermentation product, said process comprising:
    (a) saccharifying a cellulosic material or xylan-containing material with an enzyme composition in the presence of the polypeptide having beta-glucosidase activity of claim 1;
    (b) fermenting the saccharified cellulosic material or xylan-containing material with one or more fermenting microorganisms to produce the fermentation product; and
    (c) recovering the fermentation product from the fermentation.

15. A process of fermenting a cellulosic material or xylan-containing material, said process comprising: fermenting the cellulosic material or xylan-containing material with one or more fermenting microorganisms, wherein the cellulosic material or xylan-containing material is saccharified with an enzyme composition in the presence of the polypeptide having beta-glucosidase activity of claim 1.

16. The process of claim 15, wherein the fermenting of the cellulosic material or xylan-containing material produces a fermentation product.

17. The process of claim 16, further comprising recovering the fermentation product from the fermentation.

18. A recombinant expression vector comprising an isolated polynucleotide comprising a nucleotide sequence that encodes the polypeptide of claim 1.

19. The polypeptide of claim 1, comprising an amino acid sequence having at least 96% sequence identity to amino acids 22 to 782 of SEQ ID NO: 2.

20. The polypeptide of claim 19, comprising an amino acid sequence having at least 97% sequence identity to amino acids 22 to 782 of SEQ ID NO: 2.

21. The polypeptide of claim 20, comprising an amino acid sequence having at least 98% sequence identity to amino acids 22 to 782 of SEQ ID NO: 2.

22. The polypeptide of claim 21, comprising an amino acid sequence having at least 99% sequence identity to amino acids 22 to 782 of SEQ ID NO: 2.

23. The polypeptide of claim 1, which is encoded by a polynucleotide comprising a nucleotide sequence having at least 99% sequence identity to nucleotides 64 to 2707 of SEQ ID NO: 1 or a cDNA sequence thereof.

24. The polypeptide of claim 1, comprising the amino acid sequence of SEQ ID NO: 2 or amino acids 22 to 782 thereof; or a fragment thereof having beta-glucosidase activity.

25. The polypeptide of claim 1, consisting of the amino acid sequence of SEQ ID NO: 2 or amino acids 22 to 782 thereof; or a fragment thereof having beta-glucosidase activity.

* * * * *

SEQUENCE LISTING

```
<160> NUMBER OF SEQ ID NOS: 40

<210> SEQ ID NO 1
<211> LENGTH: 2710
<212> TYPE: DNA
<213> ORGANISM: Aspergillus aculeatus

<400> SEQUENCE: 1
atgaccccca tctggcatta cctcgctgtt ttaacccttc tccttccagg ataccttgcg      60
gccgagcgtc accgccgcga tgatgatgcc gatgcctact cacccctat tacccagccc      120 tcctggaggc tggatctcgg actggagcgc ggcatacgca aaggctcaag ccgtggtgag      180
caacatgact cttgctgaga aagttaacct cactaccggc acgggaatgt acatgggccc      240
ttgtgtcggc caaacaggaa gcgcactgcg ttttggcatt ccaaatctct gtcttcagga      300
ctcgcctctc ggcatccgga actcggatca caacactgcc ttccctcctg gagtgactgt      360
cggggccacc tgggataagg acctgatgta ccagcgtggt gtggagctgg acaggaagc      420 tcgtggaaag ggtgtgaatg ttctcctagg tccggtggtt gggcccatgt tcaggaagcc      480
gcttggtggg cgcgggtggg agggcttcgg agcggacccc acgctgcagg cggttggagg      540
cgcgttgacg atccagggca tgcaaagcac tggtgccatt gcttgcttga agcattacat      600
tggcaatgag caggagatgt atcgcgagac ctcggtgctg accacgggtt attcgtcgaa      660
cattgatgat cgtactttgc atgagctgta tctctggccc tttgctgagg gtgttagagc      720
tggagttggg tcggtgatga ctgcatacaa taatgtgagt gtgggtatag aggtgatttg      780
ggccttctgg gctgacaagc gcaggtgaat cgttcggcgt gcagccaaaa cagcatgctc      840
atcaatggca tcctcaagga tgagttgggc tttcaaggat ttgtcatgac cgactggctg      900
gctcagcagg ggggtgtctc atctgcctta gctggacttg acatggctat gcctggcgac      960
ggcgcgattc ctttgctagg gactgccttc tggggatcgg agctgtcaac cgcaattctc     1020
aacggaacag taccgctgga ccgactcaat gatatggtgg gatatcttcc atcctgctgc     1080
tggaatcatg ctaagcccctc tcaaggtcac tcggattgta gcgacctggt atcaaatggg     1140
tcaagaccag gattaccctc tacccaactt ttcgagcaac accctcgaca aaacgggtcc     1200
tctctacccc ggtgccttat tctccccaac aggagttgtc aaccaatttg tcgacgtgca     1260
aggcaaccat aatgtcacgg cccatgcgat tgctcgggac gcgatcaccc tcctaaaaat     1320
gacaacgata ccttgcccct caaacgcaat gcttctctca aagtgtttgg taccgatgct     1380
```

```
gggccgaaca aatcaggtct caactcctgt agtgacatgg gctgcgacca gggcgttctg      1440
accatgggct ggggaagtgg cacctcacgc ctgccctctc tcgtgacgcc gcaagaagca      1500
attgccaatg tttccacatc gaacacaacc accttctata tcacagacac cttcccttcc      1560
aacctcccca cgccatcgtc atccgacatc gctgtcgtct tcatcaacgc cgactccgga      1620
gagaactaca tcaccgttga gtccaaccca ggggaccgca ccaacgccgg cctctacgcg      1680
tggcacaacg cgacgcgct cgtccaagct gcagcatcca agttcaccac agtggttgtg      1740
gtcatccata ccgtcggccc gatcctcctc gagtcattca tcgaccttcc cagcgtgaaa      1800
gccgtgctcg ttgcgcatct ccccggccaa gccgccggct attcgctcac cgacgttctc      1860
tacggcgata ccagccccag cagccacctg ccctacacca tccccgcgtc tgcgtccgac      1920
tacccatcct ccacggacat catcacctcg aacctctgt tctcccagat ccaggactgg      1980
tttgacgagg ggctctacat cgactaccgc tacttcctga aagcaaacat caccccccgct     2040 atcccttcgg ccacggcttg tcgtatacaa ccttccagta ctccgccccc gcactgacga      2100
ccgtgaccgc cctgagcagc gcatatcccg ccgcacgcgc cagcaaggcc tccgtcccca      2160
cctaccccac aaccatccct gatccgtccg aggtcgcatg gcccagcacg ttgaaccgga      2220
tctggcgtta cctatacccg taccttgatg accccgagag cgttactaac tccacgagta      2280
cctacgcgta cccgtctggc tactccacga cggcgcaccc ggccccgcgc gccggggcgg      2340
gcagggcggg aacccggcgc tgtttgagac ggccttcgag atcgacgtga ccgtcacaaa      2400
cacgggcgaa cggagtggga gggcggtggc gcagctgtat gtacagttac cggggcaggc      2460
ggttttgggc gtcgatacgc cgcagagaca gctccgggcg tttgcgaaga ccgcgacctt      2520
ggcccccagg gcgagtgagg tggtcaagtt gactgtgacg aggaaggatc tgagtgtctg      2580
ggatgttacg gtgcaggatt ggagggtgcc tgttgctggg gaggggtgg ttttctgggt       2640 aggggagagt gtcgcggagg agggtttgag ggttaggtgt gcagtggggg gtgcttgtga      2700
ggttctctag                                                             2710
```

<210> SEQ ID NO 2
<211> LENGTH: 782
<212> TYPE: PRT
<213> ORGANISM: Aspergillus aculeatus

<400> SEQUENCE: 2

```
Met Thr Pro Ile Trp His Tyr Leu Ala Val Leu Thr Leu Leu Leu Pro
1               5                   10                  15

Gly Tyr Leu Ala Ala Glu Arg His Arg Arg Asp Asp Ala Asp Ala
            20                  25                  30

Tyr Ser Pro Pro Ile Thr Gln Pro Ser Trp Arg Leu Asp Leu Gly Leu
        35                  40                  45

Glu Arg Gly Ile Arg Lys Gly Ser Ser Arg Gly Ser Ala Leu Arg Phe
    50                  55                  60

Gly Ile Pro Asn Leu Cys Leu Gln Asp Ser Pro Leu Gly Ile Arg Asn
65                  70                  75                  80

Ser Asp His Asn Thr Ala Phe Pro Pro Gly Val Thr Val Gly Ala Thr
                85                  90                  95

Trp Asp Lys Asp Leu Met Tyr Gln Arg Gly Val Glu Leu Gly Gln Glu
            100                 105                 110

Ala Arg Gly Lys Gly Val Asn Val Leu Leu Gly Pro Val Val Gly Pro
        115                 120                 125

Met Phe Arg Lys Pro Leu Gly Gly Arg Gly Trp Glu Gly Phe Gly Ala
    130                 135                 140
```

```
Asp Pro Thr Leu Gln Ala Val Gly Gly Ala Leu Thr Ile Gln Gly Met
145                 150                 155                 160

Gln Ser Thr Gly Ala Ile Ala Cys Leu Lys His Tyr Ile Gly Asn Glu
                165                 170                 175

Gln Glu Met Tyr Arg Glu Thr Ser Val Leu Thr Thr Gly Tyr Ser Ser
            180                 185                 190

Asn Ile Asp Asp Arg Thr Leu His Glu Leu Tyr Leu Trp Pro Phe Ala
        195                 200                 205

Glu Gly Val Arg Ala Gly Val Gly Ser Val Met Thr Ala Tyr Asn Asn
210                 215                 220

Val Asn Arg Ser Ala Cys Ser Gln Asn Ser Met Leu Ile Asn Gly Ile
225                 230                 235                 240

Leu Lys Asp Glu Leu Gly Phe Gln Gly Phe Val Met Thr Asp Trp Leu
                245                 250                 255

Ala Gln Gln Gly Gly Val Ser Ser Ala Leu Ala Gly Leu Asp Met Ala
            260                 265                 270

Met Pro Gly Asp Gly Ala Ile Pro Leu Leu Gly Thr Ala Phe Trp Gly
        275                 280                 285

Ser Glu Leu Ser Thr Ala Ile Leu Asn Gly Thr Val Pro Leu Asp Arg
290                 295                 300

Leu Asn Asp Met Val Thr Arg Ile Val Ala Thr Trp Tyr Gln Met Gly
305                 310                 315                 320

Gln Asp Gln Asp Tyr Pro Leu Pro Asn Phe Ser Ser Asn Thr Leu Asp
                325                 330                 335

Lys Thr Gly Pro Leu Tyr Pro Gly Ala Leu Phe Ser Pro Thr Gly Val
            340                 345                 350

Val Asn Gln Phe Val Asp Val Gln Gly Asn His Asn Val Thr Ala His
        355                 360                 365

Ala Ile Ala Arg Asp Ala Ile Thr Leu Leu Lys Met Thr Thr Ile Pro
370                 375                 380

Cys Pro Ser Asn Ala Met Leu Leu Ser Asn Asp Met Gly Cys Asp Gln
385                 390                 395                 400

Gly Val Leu Thr Met Gly Trp Gly Ser Gly Thr Ser Arg Leu Pro Ser
                405                 410                 415

Leu Val Thr Pro Gln Glu Ala Ile Ala Asn Val Ser Thr Ser Asn Thr
            420                 425                 430

Thr Thr Phe Tyr Ile Thr Asp Thr Phe Pro Ser Asn Leu Pro Thr Pro
        435                 440                 445

Ser Ser Ser Asp Ile Ala Val Val Phe Ile Asn Ala Asp Ser Gly Glu
450                 455                 460

Asn Tyr Ile Thr Val Glu Ser Asn Pro Gly Asp Arg Thr Asn Ala Gly
465                 470                 475                 480

Leu Tyr Ala Trp His Asn Gly Asp Ala Leu Val Gln Ala Ala Ala Ser
                485                 490                 495

Lys Phe Thr Thr Val Val Val Ile His Thr Val Gly Pro Ile Leu
            500                 505                 510

Leu Glu Ser Phe Ile Asp Leu Pro Ser Val Lys Ala Val Leu Val Ala
        515                 520                 525

His Leu Pro Gly Gln Ala Ala Gly Tyr Ser Leu Thr Asp Val Leu Tyr
530                 535                 540

Gly Asp Thr Ser Pro Ser Ser His Leu Pro Tyr Thr Ile Pro Ala Ser
545                 550                 555                 560

Ala Ser Asp Tyr Pro Ser Ser Thr Asp Ile Ile Thr Ser Gln Pro Leu
```

```
                        565                 570                 575
Phe Ser Gln Ile Gln Asp Cys Lys His His Pro Arg Tyr Pro Phe Gly
                580                 585                 590
His Gly Leu Ser Tyr Thr Thr Phe Gln Tyr Ser Ala Pro Ala Leu Thr
            595                 600                 605
Thr Val Thr Ala Leu Ser Ser Ala Tyr Pro Ala Ala Arg Ala Ser Lys
        610                 615                 620
Ala Ser Val Pro Thr Tyr Pro Thr Thr Ile Pro Asp Pro Ser Glu Tyr
625                 630                 635                 640
Leu Arg Val Pro Val Trp Leu Leu His Asp Gly Ala Pro Gly Pro Ala
                645                 650                 655
Arg Arg Gly Gly Gln Gly Gly Asn Pro Ala Leu Phe Glu Thr Ala Phe
            660                 665                 670
Glu Ile Asp Val Thr Val Thr Asn Thr Gly Glu Arg Ser Gly Arg Ala
        675                 680                 685
Val Ala Gln Leu Tyr Val Gln Leu Pro Gly Gln Ala Val Leu Gly Val
        690                 695                 700
Asp Thr Pro Gln Arg Gln Leu Arg Ala Phe Ala Lys Thr Ala Thr Leu
705                 710                 715                 720
Ala Pro Arg Ala Ser Glu Val Val Lys Leu Thr Val Thr Arg Lys Asp
                725                 730                 735
Leu Ser Val Trp Asp Val Thr Val Gln Asp Trp Arg Val Pro Val Ala
            740                 745                 750
Gly Glu Gly Val Val Phe Trp Val Gly Glu Ser Val Ala Glu Glu Gly
        755                 760                 765
Leu Arg Val Arg Cys Ala Val Gly Gly Ala Cys Glu Val Leu
    770                 775                 780

<210> SEQ ID NO 3
<211> LENGTH: 2560
<212> TYPE: DNA
<213> ORGANISM: Aspergillus aculeatus

<400> SEQUENCE: 3
atgagattca tttcacttgc cgtaacggca gccttgcttg gcttgacaag cgccacgaat        60
tcttcaacat tgggtctact caaggctaat ggtggtaagt agactggcca tgtatcatga       120
ttcttggaag catgctaaat aacgaatagt cacgctggga gactggaggc tgcatatga        180 aaaggcatct gccttcgttg caggactgac tactgatcag aagctggctt tgatcaccgg       240
tagcagtgtt agctcatcca atggtaactt cagtgctcta gagttccttg atggggatat       300
gggtcttcag aactatttct atgtctctgc tttcagcttg tcctccgctt ggctatgac        360 ttgggaccgc gacgccatct atgctcaagc caaagcagtt gggtcggagt ctacaacaa        420 aggcattcag gtggttgctg gtcctacttc tcagccaatg ggtcgtactc cttggggtgg       480
tcgtaatgtc gagggattcg gccctgatcc ctatctaaat ggcctggcta ctggcctgtc       540
taccaagggt tatgtcgacg ctggagtgat ccccggtggc aaagtaagat gatccatgga       600
cagtgtaact acgggcttgc tgactctaac tgcgccatct gctagcattt tctcctttac       660
gagcaagaaa ccaaccggac ttccagtggc ggcggcggtg gtggtggtgg aagtggagga       720
ggaatgcctt ccggggggaat gggctttggt ggttccaact cttcgtcgcc tgggcctcag       780
ccttccggtt cattcagtcg gcgtgctact gtctcctcgg actccgactc ggcaccctat       840
tcctccaacg cagacgacaa aaccttgcac gaaacatacc tctggccatt ctacgatgca       900
gtgaagaatg gccttggcgc cgtcatgtgc gcaatgacca aagtcaatgg cacttacagc       960
```

```
tgcgaaaact cggatctcct gatgaagacg ctcaagacag agcttggctt tccgggtctg    1020
gtctggcccg acatgaatgg gcaaaacagc gccgaaggat cagcattagg cggcgaggac    1080
tatggctcga gcagtatctg gagcacttct acaatgaaga ctcttctgtc gaatggtacc    1140
ctcaccgagg cccggttgaa cgacatggca atcagaaacc ttattgggta ttaccatgtc    1200
aatctggaca atggccttca acctgcgatg caagatcagg atgcctatgt ggacgtacga    1260
ggcaatcatt ccaagctgat ccgcgagaac ggcgccaagt cgatggcttt gttgaagaat    1320
gaaggcactc ttccgttgaa aaagccccgt gtgatgagtg ttttcggagc ccatgctggc    1380
ccggtcatgg gaggaccgaa tgctgccatg aacgtcgaag ggtctggccc gacctaccaa    1440
ggccatttgg ccaccggcac tggctctgga caggcatctg ttccttacgt gattacccct    1500
tacgttgccc taactatcag agctgcgcaa gatgcaacta tgatgcgatg gattatgaac    1560
gatacttata gctccagtgg aggatccacg ctgattcaag aaggaactga cagtaccgcc    1620
gtgtcaccct cgtatgccaa ctatgctacc aactcggatg tctgcctcgt tttcatcaat    1680
gctctgtcag gtgagggtgc tgaccgcact gagctgtata cgaggatca agacactatg    1740 ataaacacgg ttgcagacaa ctgtaacaat accgtggttg tagtcaacac cgttgggccc    1800
cgactgctgg accagtggat tgagcacgac aacgtgacgg cagttctcta cggatctatt    1860
ctgggccaag agtcgggcaa cgcaattgtg gaccttctct atgtgatgtg aacccttccg    1920
gccgtcttat ccacactatc gctaagaacg agagtgatta caaggtggag ctctgctaca    1980
ctgctcaatg caactttact gagggtaagt cgtcattgat cttcgagtat cggtgctctt    2040
tggcctataa cgctgaccg catccacagg agtctacatt gactaccgct atttcgacgc    2100
caagaacgtt actcccagat acccattcgg tcatggtctt tcttacacca ctttcaagta    2160
ctcggatctc gccatcaaga ccccttctgc cacgaccaaa gctccccggg gtaaccatac    2220
cgtcggtgga aacagtgatc tatgggacgt tgtgggaacc gtctctgcgc gcatcaccaa    2280
taatggcacg cttgcaggtg cggaaattcc ccagctctac cttggctttc cagatgccgc    2340
agatcaacct gttcgtcagc tccgcggatt cgagcgtgtt gaactacggg caggacagga    2400
gtctattgtt acgttcagcc tgcgtcgtcg cgacatttca tactgggacg tggctgctca    2460
gcaatggctt gttgcttctg ggaaatacca ggtctacgtt ggagcaagct ctcgcgactt    2520
cagattgacg ggagcattct ctttgagagt gaaggcttag                          2560
```

<210> SEQ ID NO 4
<211> LENGTH: 776
<212> TYPE: PRT
<213> ORGANISM: Aspergillus aculeatus

<400> SEQUENCE: 4

```
Met Arg Phe Ile Ser Leu Ala Val Thr Ala Ala Leu Leu Gly Leu Thr
1               5                   10                  15

Ser Ala Thr Asn Ser Ser Thr Leu Gly Leu Leu Lys Ala Asn Gly Val
            20                  25                  30

Thr Leu Gly Asp Trp Glu Ala Ala Tyr Glu Lys Ala Ser Ala Phe Val
        35                  40                  45

Ala Gly Leu Thr Thr Asp Gln Lys Leu Ala Leu Ile Thr Gly Ser Ser
    50                  55                  60

Val Ser Ser Ser Asn Gly Asn Phe Ser Ala Leu Glu Phe Leu Asp Gly
65                  70                  75                  80

Asp Met Gly Leu Gln Asn Tyr Phe Tyr Val Ser Ala Phe Ser Leu Ser
                85                  90                  95
```

-continued

Ser Ala Leu Ala Met Thr Trp Asp Arg Asp Ala Ile Tyr Ala Gln Ala
            100                 105                 110
Lys Ala Val Gly Ser Glu Phe Tyr Asn Lys Gly Ile Gln Val Val Ala
            115                 120                 125
Gly Pro Thr Ser Gln Pro Met Gly Arg Thr Pro Trp Gly Gly Arg Asn
130                 135                 140
Val Glu Gly Phe Gly Pro Asp Pro Tyr Leu Asn Gly Leu Ala Thr Gly
145                 150                 155                 160
Leu Ser Thr Lys Gly Tyr Val Asp Ala Gly Val Ile Pro Gly Gly Lys
                165                 170                 175
His Phe Leu Leu Tyr Glu Gln Glu Thr Asn Arg Thr Ser Ser Gly Gly
            180                 185                 190
Gly Gly Gly Gly Gly Ser Gly Gly Met Pro Ser Gly Gly Met
            195                 200                 205
Gly Phe Gly Gly Ser Asn Ser Ser Pro Gly Pro Gln Pro Ser Gly
210                 215                 220
Ser Phe Ser Arg Arg Ala Thr Val Ser Ser Asp Ser Asp Ser Ala Pro
225                 230                 235                 240
Tyr Ser Ser Asn Ala Asp Asp Lys Thr Leu His Glu Thr Tyr Leu Trp
                245                 250                 255
Pro Phe Tyr Asp Ala Val Lys Asn Gly Leu Gly Ala Val Met Cys Ala
            260                 265                 270
Met Thr Lys Val Asn Gly Thr Tyr Ser Cys Glu Asn Ser Asp Leu Leu
            275                 280                 285
Met Lys Thr Leu Lys Thr Glu Leu Gly Phe Pro Gly Leu Val Trp Pro
            290                 295                 300
Asp Met Asn Gly Gln Asn Ser Ala Glu Gly Ser Ala Leu Gly Gly Glu
305                 310                 315                 320
Asp Tyr Gly Ser Ser Ser Ile Trp Ser Thr Ser Thr Met Lys Thr Leu
                325                 330                 335
Leu Ser Asn Gly Thr Leu Thr Glu Ala Arg Leu Asn Asp Met Ala Ile
            340                 345                 350
Arg Asn Leu Ile Gly Tyr Tyr His Val Asn Leu Asp Asn Gly Leu Gln
            355                 360                 365
Pro Ala Met Gln Asp Gln Asp Ala Tyr Val Asp Val Arg Gly Asn His
            370                 375                 380
Ser Lys Leu Ile Arg Glu Asn Gly Ala Lys Ser Met Ala Leu Leu Lys
385                 390                 395                 400
Asn Glu Gly Thr Leu Pro Leu Lys Lys Pro Arg Val Met Ser Val Phe
                405                 410                 415
Gly Ala His Ala Gly Pro Val Met Gly Gly Pro Asn Ala Ala Met Asn
            420                 425                 430
Val Glu Gly Ser Gly Pro Thr Tyr Gln Gly His Leu Ala Thr Gly Thr
            435                 440                 445
Gly Ser Gly Gln Ala Ser Val Pro Tyr Val Ile Thr Pro Tyr Val Ala
        450                 455                 460
Leu Thr Ile Arg Ala Ala Gln Asp Ala Thr Met Met Arg Trp Ile Met
465                 470                 475                 480
Asn Asp Thr Tyr Ser Ser Gly Gly Ser Thr Leu Ile Gln Glu Gly
                485                 490                 495
Thr Asp Ser Thr Ala Val Ser Pro Ser Tyr Ala Asn Tyr Ala Thr Asn
            500                 505                 510
Ser Asp Val Cys Leu Val Phe Ile Asn Ala Leu Ser Gly Glu Gly Ala

```
                            515                 520                 525
Asp Arg Thr Glu Leu Tyr Asn Glu Asp Gln Asp Thr Met Ile Asn Thr
530                 535                 540

Val Ala Asp Asn Cys Asn Asn Thr Val Val Val Asn Thr Val Gly
545                 550                 555                 560

Pro Arg Leu Leu Asp Gln Trp Ile Glu His Asp Asn Val Thr Ala Val
                565                 570                 575

Leu Tyr Gly Ser Ile Leu Gly Gln Glu Ser Gly Asn Ala Ile Val Asp
            580                 585                 590

Leu Leu Tyr Val Ile Asp Tyr Lys Val Glu Leu Cys Tyr Thr Ala Gln
        595                 600                 605

Cys Asn Phe Thr Glu Gly Val Tyr Ile Asp Tyr Arg Tyr Phe Asp Ala
610                 615                 620

Lys Asn Val Thr Pro Arg Tyr Pro Phe Gly His Gly Leu Ser Tyr Thr
625                 630                 635                 640

Thr Phe Lys Tyr Ser Asp Leu Ala Ile Lys Thr Pro Ser Ala Thr Thr
                645                 650                 655

Lys Ala Pro Arg Gly Asn His Thr Val Gly Gly Asn Ser Asp Leu Trp
            660                 665                 670

Asp Val Val Gly Thr Val Ser Ala Arg Ile Thr Asn Asn Gly Thr Leu
        675                 680                 685

Ala Gly Ala Glu Ile Pro Gln Leu Tyr Leu Gly Phe Pro Asp Ala Ala
    690                 695                 700

Asp Gln Pro Val Arg Gln Leu Arg Gly Phe Glu Arg Val Glu Leu Arg
705                 710                 715                 720

Ala Gly Gln Glu Ser Ile Val Thr Phe Ser Leu Arg Arg Arg Asp Ile
                725                 730                 735

Ser Tyr Trp Asp Val Ala Ala Gln Gln Trp Leu Val Ala Ser Gly Lys
            740                 745                 750

Tyr Gln Val Tyr Val Gly Ala Ser Ser Arg Asp Phe Arg Leu Thr Gly
        755                 760                 765

Ala Phe Ser Leu Arg Val Lys Ala
    770                 775

<210> SEQ ID NO 5
<211> LENGTH: 2633
<212> TYPE: DNA
<213> ORGANISM: Aspergillus aculeatus

<400> SEQUENCE: 5
atgcacagct taggatcctt gatcgccctc ttgggtggtc tttctctttg ctccgccgca      60
ccaactgagc agaacatcac cagcgatata tacttctatg cgattctcc cccagtctac     120 ccctcccgta ggttttccca tgatcttctc atttgtcatt cactgctcac gcagcacttc    180
agccgagggt accggtactg gtggatgggc tgcagcgtac gagaaagcaa agagtttcgt    240
cgcccagctc acgacgagg agaaggtcaa cttcacggca ggctacagtg ccagtaatgg     300
gtgctcgggc aatattccag cagtctcccg tctaggcttt cctggctatt gtgtgtcgga    360
tgcgggaaat gggctggtat gtggacccaa gtaggattgg agttgtcttt tctaaaagct    420
gtacacagcg cggaacggac ttcgtgaatg ctgggccag tggcattcat gttggagcaa     480
ggtacgcatg ctacagcagt ctttgaatct gttgaattcc ttgctaattc ctcgcttcta    540
gctggaacaa aaccccttgct caccaacggg ctctgtacat gggacaagag tttcatcgaa    600
agggtgtcaa ccttctgctg ggccctgtgg ttggccccat cggtcgtgtc gcggaaggcg    660
```

```
gacggaactg ggaaggcttc tccactgatc cctatctcag cggggcgctg gtgtatgaga      720
cagtccaagg tgtgcaggag gccggcgttg gtgtctctgt gaaggtgtgt atactcctta      780
ctgctttatc ttaaccgcga gtgatactga ttgacacact caaagcacta catcggaaac      840
gagcaagaga ccaacagaaa ccctgagaca gagaatggag tcacagtcgc ctcggtttcc      900
tcgaatattg atgacaagac catccatgaa ctctacctct ggcccttcca agatgccgtg      960
ctggcgggca gtgtctcagt catgtgctcg tacaaccggg tcaataactc ctatgcctgt     1020
cagaacagca agacgctcaa cgggctattg aagactgaac taggtttcca aggtaagaga     1080
ctcatattac ccactactgg acaccgttgc ttatacgcag aaggctatgt tgttactgat     1140
tggggtgccc agcacgccgg gattgctggt gctaatgccg gctggacat ggtcatgcca      1200 agtaccacca catgggggttc caatctcacc acggccatag ccaatggtag tatgaagca    1260 tcgagactcg acgacatggt tactaggtaa gctaggccac cttcactagt ggttttctca     1320
ctgacccggc cagaatcatc gcttcttggt atcaaatgaa ccaagacacc gacttcccat     1380
ctcctggaat cggcatgccc gaagacgtct actccgagca cgaagttgtc atcggaactt     1440
ctgccgatga gaaagacgct ctacttcaga gcgcaattga gggccacgtt ctcgtcaaaa     1500
acgagaactc tgcgctacct ctccagtcac cccgcctcgt ctctgtattt ggatacgatg     1560
ccaaagcccc cgagtccgca agcttaaccc tttcattcga cagtgtcatg ccggccatcc     1620
agaactacac tctctgggtt ggcggcggct ccggctccaa cagcccagca tacatcatcg     1680
cgcctctcga cgccattcaa caacaagcct atgaagacaa caccgctgtc ctatgggacg     1740
tgagctccaa tgacccggac gttgaccctg cctcctccgc ctgcctggtc tttatcaaca     1800
gctacgcgtc cgaaggaggc gatcgaccag gtctcgttga tgcggacagc gacacgctcg     1860
tgaacaatgt cgccaacaaa tgcaacaaca cgatcgtcgt gatccacaac gcgggtattc     1920
gcctcgctta cgattggatc gaccatgcca acgtcaccgc cgtgattctt gcccaccttc     1980
ctggtcaaga cacgggcacg gctgtcgtcg acttgctgta cggccgtgct aacccctccg     2040
gccgactgcc ctacacggtc gccaagcagg catccgacta cggggcgatc ttgcacccgg     2100
tccagcctgt ggccccgtat ggcctctttc cacaggacga cttcaccgag gcgtctaca    2160 tcgactaccg cgccttcgac aaggagaaca tcaccccgca gttcgagttc gggttcggcc     2220
tctcgtatac caccttcaat tattccgggt tggacatcca gaggacatcg gtcgaggcga    2280
cacagtaccc accagccgca gccattcagg aaggaggcaa cccacgtctg tgggatgtgc     2340
tcgccaacgt cacggcgcag gtgcggaact ccgggaatgt ggacgggcg gaggtcgcgc     2400 agctgtacgt ggggatcccc aatgggccgg ttcggcagct gcgtgggttt gacaaggtca     2460
atgtccctgt gggcgagacg gtggctgtct cgttctctct gacgcggcgc gacctgagta     2520
cgtggagtgt cgaggcgcag gcgtgggcgc tgcagacggg agagtaccag gtgtatgtgg     2580
ggaggtcgag tcgggatctg ccgcttacgg ggacgttgac gttgaccgtg tag            2633
```

<210> SEQ ID NO 6
<211> LENGTH: 768
<212> TYPE: PRT
<213> ORGANISM: Aspergillus aculeatus

<400> SEQUENCE: 6

```
Met His Ser Leu Gly Ser Leu Ile Ala Leu Leu Gly Gly Leu Ser Leu
1               5                  10                  15

Cys Ser Ala Ala Pro Thr Glu Gln Asn Ile Thr Ser Asp Ile Tyr Phe
            20                  25                  30
```

Tyr Gly Asp Ser Pro Pro Val Tyr Pro Ser Pro Glu Gly Thr Gly Thr
            35                  40                  45

Gly Gly Trp Ala Ala Ala Tyr Glu Lys Ala Lys Ser Phe Val Ala Gln
 50                  55                  60

Leu Thr Asp Glu Glu Lys Val Asn Phe Thr Ala Gly Tyr Ser Ala Ser
 65                  70                  75                  80

Asn Gly Cys Ser Gly Asn Ile Pro Ala Val Ser Arg Leu Gly Phe Pro
             85                  90                  95

Gly Tyr Cys Val Ser Asp Ala Gly Asn Gly Leu Arg Gly Thr Asp Phe
            100                 105                 110

Val Asn Gly Trp Ala Ser Gly Ile His Val Gly Ala Ser Trp Asn Lys
            115                 120                 125

Thr Leu Ala His Gln Arg Ala Leu Tyr Met Gly Gln Glu Phe His Arg
        130                 135                 140

Lys Gly Val Asn Leu Leu Gly Pro Val Val Gly Pro Ile Gly Arg
145                 150                 155                 160

Val Ala Glu Gly Gly Arg Asn Trp Glu Gly Phe Ser Thr Asp Pro Tyr
                165                 170                 175

Leu Ser Gly Ala Leu Val Tyr Glu Thr Val Gln Gly Val Gln Glu Ala
            180                 185                 190

Gly Val Gly Val Ser Val Lys His Tyr Ile Gly Asn Glu Gln Glu Thr
            195                 200                 205

Asn Arg Asn Pro Glu Thr Glu Asn Gly Val Thr Val Ala Ser Val Ser
210                 215                 220

Ser Asn Ile Asp Asp Lys Thr Ile His Glu Leu Tyr Leu Trp Pro Phe
225                 230                 235                 240

Gln Asp Ala Val Leu Ala Gly Ser Val Ser Val Met Cys Ser Tyr Asn
            245                 250                 255

Arg Val Asn Asn Ser Tyr Ala Cys Gln Asn Ser Lys Thr Leu Asn Gly
                260                 265                 270

Leu Leu Lys Thr Glu Leu Gly Phe Gln Gly Tyr Val Thr Asp Trp
        275                 280                 285

Gly Ala Gln His Ala Gly Ile Ala Gly Ala Asn Ala Gly Leu Asp Met
290                 295                 300

Val Met Pro Ser Thr Thr Thr Trp Gly Ser Asn Leu Thr Thr Ala Ile
305                 310                 315                 320

Ala Asn Gly Ser Met Glu Ala Ser Arg Leu Asp Asp Met Val Thr Arg
                325                 330                 335

Ile Ile Ala Ser Trp Tyr Gln Met Asn Gln Asp Thr Asp Phe Pro Ser
            340                 345                 350

Pro Gly Ile Gly Met Pro Glu Asp Val Tyr Ser Glu His Glu Val Val
            355                 360                 365

Ile Gly Thr Ser Ala Asp Glu Lys Asp Ala Leu Leu Gln Ser Ala Ile
        370                 375                 380

Glu Gly His Val Leu Val Lys Asn Glu Asn Ser Ala Leu Pro Leu Gln
385                 390                 395                 400

Ser Pro Arg Leu Val Ser Val Phe Gly Tyr Asp Ala Lys Ala Pro Glu
                405                 410                 415

Ser Ala Ser Leu Thr Leu Ser Phe Asp Ser Val Met Pro Ala Ile Gln
            420                 425                 430

Asn Tyr Thr Leu Trp Val Gly Gly Ser Gly Ser Asn Ser Pro Ala
        435                 440                 445

Tyr Ile Ile Ala Pro Leu Asp Ala Ile Gln Gln Gln Ala Tyr Glu Asp
450                 455                 460

```
Asn Thr Ala Val Leu Trp Asp Val Ser Ser Asn Asp Pro Asp Val Asp
465                 470                 475                 480

Pro Ala Ser Ser Ala Cys Leu Val Phe Ile Asn Ser Tyr Ala Ser Glu
            485                 490                 495

Gly Gly Asp Arg Pro Gly Leu Val Asp Ala Asp Ser Asp Thr Leu Val
        500                 505                 510

Asn Asn Val Ala Asn Lys Cys Asn Asn Thr Ile Val Val Ile His Asn
            515                 520                 525

Ala Gly Ile Arg Leu Ala Tyr Asp Trp Ile Asp His Ala Asn Val Thr
        530                 535                 540

Ala Val Ile Leu Ala His Leu Pro Gly Gln Asp Thr Gly Thr Ala Val
545                 550                 555                 560

Val Asp Leu Leu Tyr Gly Arg Ala Asn Pro Ser Gly Arg Leu Pro Tyr
                565                 570                 575

Thr Val Ala Lys Gln Ala Ser Asp Tyr Gly Ala Ile Leu His Pro Val
            580                 585                 590

Gln Pro Val Ala Pro Tyr Gly Leu Phe Pro Gln Asp Asp Phe Thr Glu
        595                 600                 605

Gly Val Tyr Ile Asp Tyr Arg Ala Phe Asp Lys Glu Asn Ile Thr Pro
        610                 615                 620

Gln Phe Glu Phe Gly Phe Gly Leu Ser Tyr Thr Thr Phe Asn Tyr Ser
625                 630                 635                 640

Gly Leu Asp Ile Gln Arg Thr Ser Val Glu Ala Thr Gln Tyr Pro Pro
                645                 650                 655

Ala Ala Ala Ile Gln Glu Gly Gly Asn Pro Arg Leu Trp Asp Val Leu
            660                 665                 670

Ala Asn Val Thr Ala Gln Val Arg Asn Ser Gly Asn Val Asp Gly Ala
        675                 680                 685

Glu Val Ala Gln Leu Tyr Val Gly Ile Pro Asn Gly Pro Val Arg Gln
        690                 695                 700

Leu Arg Gly Phe Asp Lys Val Asn Val Pro Val Gly Glu Thr Val Ala
705                 710                 715                 720

Val Ser Phe Ser Leu Thr Arg Arg Asp Leu Ser Thr Trp Ser Val Glu
                725                 730                 735

Ala Gln Ala Trp Ala Leu Gln Thr Gly Glu Tyr Gln Val Tyr Val Gly
            740                 745                 750

Arg Ser Ser Arg Asp Leu Pro Leu Thr Gly Thr Leu Thr Leu Thr Val
                755                 760                 765

<210> SEQ ID NO 7
<211> LENGTH: 2346
<212> TYPE: DNA
<213> ORGANISM: Aspergillus aculeatus

<400> SEQUENCE: 7
atgggtgcta gtttgctaac caaggggctt gccctcctcc acctctgcgt cgggttaacg      60
gccgcaagca atggctcaac accactctac aaggacccgc atgcttcggt ggatgatcgc     120
gtcactgatc ttctgggtcg catgacgatc catgataaaa cggcgcaatt gctgcaaggt     180
gatctctcga actggatgaa caccacgact ggagcgttca actactcagg cctcgttgcg     240
aacatggagc tgaaggctgg aggattctac gttgggtatg cggtcccgtg ggactggatg     300
gtgacgaaca tcaagcatgc gcaggattac ctggttcaca acgacgct tgggattccg       360 gcgcttgttc agacggaagg tattcatgga ttcttggttc agaacgctac catcttcaac     420
```

```
tcgcctattg catatggttg ctctttcaac cgtgagttgg tctacaaaat ggccaaaatc    480
atcagtcaag aaactcttac tcttggtgtc aatcaactgt ttgctcccgt agtggatctg    540
gctcgtgagc tgcgctatgg ccgggtcgaa gagacgttct ccgaggaccc gtaccttgct    600
ggcgagattg gctacaatta cgtgaaaggc ctgcagagtc tcaatgtttc ggccaccgtc    660
aagcattttg ccggcttcag tgcacccgag caggggctga cacggcgcc ggtccaggga    720 ggcgaaagat accttcgtac cacctggcta cactccttca agcgggcaat cattgatgca    780
ggcgcatgga gtgttatgag cgcctaccac tcctatgacg gcatcccggc tgtggccgat    840
tatctcacct tgacgaagat tctaagaggt gaatggggct tcaaacactg ggtctttagc    900
gacgctggtg ctaccgatcg actctgcacg gctttcaagc tttgccaggc ttcgccgatt    960
gacatggaat cggtcactct gcaggcactc cctgctggca atgacgttga gatgggtggt   1020
ggttctttca acttccagaa gatccccgag ctcgtagagt ctggaaagct ggacatcgaa   1080
accgtcaaca ccgctgtctc gcgtattctc cgcgccaagt cgagatggg tctcttcgag   1140 aatcccttcc ctgctgctcc cgagtcgcag tggcacaagc tgattcacag ctccgaggcg   1200
gtcgagcttg ccagaacctt ggacaaggag tctatcgtcc tattggagaa ccataacaag   1260 actcttcccct tgaagaagag cggcagcatt gcggtcattg acccatggc ccacggcttc   1320 atgaactacg gagactacgt catctacaag agccagtacc gcggcgtgac ccctctggac   1380
ggcatcaagg ccgctgtcgg cgacaaggcc acggtcaact acgctcaagg ctgcgagcgc   1440
tggagcaacg accagtccgg cttcgatgag gccatcgcgg ccgccaagaa gtccgacgtc   1500
gctgtcgtcg tcgtgggtac ctggtctcgc gaccagaccg agctgtggtc cgggttcaac   1560
gcgaccaccg tgaacacat cgacctcgac aacctcgccc ttgtcggcgc ccaaggcccg   1620
ctcgtcaagg ccattctcga cactggcgtc cccacgatcg tggttctctc cagcgggaag   1680
cccatcaccg acgtgacctg gctcgccaac tcgacttcgg cgctcgtgca gcaattctat   1740
ccctccgagc aaggcggcaa cgcgctggcc gacgtgctgt tcggcgacta caacccctct   1800
ggcaagctgt ccgtcagctt cccgcgcttc gtcggcgacc tgcccatcta ctacgacttc   1860
ctcaactcgg cgcgcaacat cgggcccgcc ggccacgcct accccaacgg cacgctggac   1920
ttcgagtccc agtacgtcct gggcgacccc accgccatct acgagttcgg gtacggcaag   1980
agctacgtcg actttgcgta tgggacggtc cagctgagta agaccaacgt caccgcgtcg   2040
gacacggtga cggtcagcgt ggacgtgacc aacaccgacg ccgcccgcga cggcaccgag   2100
gtcgtgcagg tgtacgtctc ggacgtgatc gcgtcggtgg tcgtgccaaa ccgcgcgctg   2160
aagggctttg agaaggtgct catccccgcg ggcaagacca cgacggtgga atcgatctg    2220 aaggtggagg atctgggcct gtggaaccgg tcgatgcagt acgtcgtgga gccggggcg    2280 ttcacggtgc tggtcgggag cagctcgtcg gatatccggg ggaatgcgac gttctatgtt    2340
gagtag                                                              2346
```

<210> SEQ ID NO 8
<211> LENGTH: 781
<212> TYPE: PRT
<213> ORGANISM: Aspergillus aculeatus

<400> SEQUENCE: 8

Met Gly Ala Ser Leu Leu Thr Lys Gly Leu Ala Leu Leu His Leu Cys
1               5                   10                  15

Val Gly Leu Thr Ala Ala Ser Asn Gly Ser Thr Pro Leu Tyr Lys Asp
            20                  25                  30

```
Pro His Ala Ser Val Asp Asp Arg Val Thr Asp Leu Leu Gly Arg Met
         35                  40                  45

Thr Ile His Asp Lys Thr Ala Gln Leu Leu Gln Gly Asp Leu Ser Asn
 50                  55                  60

Trp Met Asn Thr Thr Thr Gly Ala Phe Asn Tyr Ser Gly Leu Val Ala
 65                  70                  75                  80

Asn Met Glu Leu Lys Ala Gly Gly Phe Tyr Val Gly Tyr Ala Val Pro
                 85                  90                  95

Trp Asp Trp Met Val Thr Asn Ile Lys His Ala Gln Asp Tyr Leu Val
                100                 105                 110

His Asn Thr Thr Leu Gly Ile Pro Ala Leu Val Gln Thr Glu Gly Ile
            115                 120                 125

His Gly Phe Leu Val Gln Asn Ala Thr Ile Phe Asn Ser Pro Ile Ala
            130                 135                 140

Tyr Gly Cys Ser Phe Asn Arg Glu Leu Val Tyr Lys Met Ala Lys Ile
145                 150                 155                 160

Ile Ser Gln Glu Thr Leu Thr Leu Gly Val Asn Gln Leu Phe Ala Pro
                165                 170                 175

Val Val Asp Leu Ala Arg Glu Leu Arg Tyr Gly Arg Val Glu Glu Thr
            180                 185                 190

Phe Ser Glu Asp Pro Tyr Leu Ala Gly Glu Ile Gly Tyr Asn Tyr Val
            195                 200                 205

Lys Gly Leu Gln Ser Leu Asn Val Ser Ala Thr Val Lys His Phe Ala
210                 215                 220

Gly Phe Ser Ala Pro Glu Gln Gly Leu Asn Thr Ala Pro Val Gln Gly
225                 230                 235                 240

Gly Glu Arg Tyr Leu Arg Thr Thr Trp Leu His Ser Phe Lys Arg Ala
                245                 250                 255

Ile Ile Asp Ala Gly Ala Trp Ser Val Met Ser Ala Tyr His Ser Tyr
            260                 265                 270

Asp Gly Ile Pro Ala Val Ala Asp Tyr Leu Thr Leu Thr Lys Ile Leu
            275                 280                 285

Arg Gly Glu Trp Gly Phe Lys His Trp Val Phe Ser Asp Ala Gly Ala
290                 295                 300

Thr Asp Arg Leu Cys Thr Ala Phe Lys Leu Cys Gln Ala Ser Pro Ile
305                 310                 315                 320

Asp Met Glu Ser Val Thr Leu Gln Ala Leu Pro Ala Gly Asn Asp Val
                325                 330                 335

Glu Met Gly Gly Gly Ser Phe Asn Phe Gln Lys Ile Pro Glu Leu Val
            340                 345                 350

Glu Ser Gly Lys Leu Asp Ile Glu Thr Val Asn Thr Ala Val Ser Arg
            355                 360                 365

Ile Leu Arg Ala Lys Phe Glu Met Gly Leu Phe Glu Asn Pro Phe Pro
370                 375                 380

Ala Ala Pro Glu Ser Gln Trp His Lys Leu Ile His Ser Ser Glu Ala
385                 390                 395                 400

Val Glu Leu Ala Arg Thr Leu Asp Lys Glu Ser Ile Val Leu Leu Glu
                405                 410                 415

Asn His Asn Lys Thr Leu Pro Leu Lys Lys Ser Gly Ser Ile Ala Val
            420                 425                 430

Ile Gly Pro Met Ala His Gly Phe Met Asn Tyr Gly Asp Tyr Val Ile
            435                 440                 445

Tyr Lys Ser Gln Tyr Arg Gly Val Thr Pro Leu Asp Gly Ile Lys Ala
450                 455                 460
```

Ala Val Gly Asp Lys Ala Thr Val Asn Tyr Ala Gln Gly Cys Glu Arg
465                 470                 475                 480

Trp Ser Asn Asp Gln Ser Gly Phe Asp Glu Ala Ile Ala Ala Lys
            485                 490                 495

Lys Ser Asp Val Ala Val Val Val Gly Thr Trp Ser Arg Asp Gln
        500                 505                 510

Thr Glu Leu Trp Ser Gly Phe Asn Ala Thr Thr Gly Glu His Ile Asp
        515                 520                 525

Leu Asp Asn Leu Ala Leu Val Gly Ala Gln Gly Pro Leu Val Lys Ala
        530                 535                 540

Ile Leu Asp Thr Gly Val Pro Thr Ile Val Val Leu Ser Ser Gly Lys
545                 550                 555                 560

Pro Ile Thr Asp Val Thr Trp Leu Ala Asn Ser Thr Ser Ala Leu Val
                565                 570                 575

Gln Gln Phe Tyr Pro Ser Glu Gln Gly Gly Asn Ala Leu Ala Asp Val
                580                 585                 590

Leu Phe Gly Asp Tyr Asn Pro Ser Gly Lys Leu Ser Val Ser Phe Pro
                595                 600                 605

Arg Phe Val Gly Asp Leu Pro Ile Tyr Tyr Asp Phe Leu Asn Ser Ala
                610                 615                 620

Arg Asn Ile Gly Pro Ala Gly His Ala Tyr Pro Asn Gly Thr Leu Asp
625                 630                 635                 640

Phe Glu Ser Gln Tyr Val Leu Gly Asp Pro Thr Ala Ile Tyr Glu Phe
                645                 650                 655

Gly Tyr Gly Lys Ser Tyr Val Asp Phe Ala Tyr Gly Thr Val Gln Leu
                660                 665                 670

Ser Lys Thr Asn Val Thr Ala Ser Asp Thr Val Thr Val Ser Val Asp
                675                 680                 685

Val Thr Asn Thr Asp Ala Ala Arg Asp Gly Thr Glu Val Val Gln Val
                690                 695                 700

Tyr Val Ser Asp Val Ile Ala Ser Val Val Pro Asn Arg Ala Leu
705                 710                 715                 720

Lys Gly Phe Glu Lys Val Leu Ile Pro Ala Gly Lys Thr Thr Thr Val
                725                 730                 735

Glu Ile Asp Leu Lys Val Glu Asp Leu Gly Leu Trp Asn Arg Ser Met
                740                 745                 750

Gln Tyr Val Val Glu Pro Gly Ala Phe Thr Val Leu Val Gly Ser Ser
                755                 760                 765

Ser Ser Asp Ile Arg Gly Asn Ala Thr Phe Tyr Val Glu
                770                 775                 780

<210> SEQ ID NO 9
<211> LENGTH: 2436
<212> TYPE: DNA
<213> ORGANISM: Aspergillus aculeatus

<400> SEQUENCE: 9
atgaagctta ccgttcccct taacggccgca gcgctgcctc tggcgggcgc agccgtcatt      60
caaccccgta cactgaacgt gaccgaccte gagcactact ggtcctacgg ccgctctgaa     120
cccgtctatc ccacaccgga gacccaaggt ctaggagact gggaagatgc cttcaccaag     180
gccaaagccc tcgtggccca gatgaccaac gaggagaaga caacctgac ctacggctac     240 tcctccacca ccaacggctg ctccggcaac acggccggcg tccccgcct gggattcccc     300 ggcatctgcc tgcaggatgc cgccagcggc gtgcgcggca ccgacatggt caacggctac     360

```
gcgtccgggc tgcacgtggg cgcctcgtgg aaccgggagc tggcctacca gcgggcgcag    420
tacatggggg ccgagttcaa gcgcaagggg gtcaacgtgg ccctgggccc cgtggccggg    480
cccctgggcc gcatcgcgcg cggcggccgc aactgggaag ggttcagcaa cgacccgtac    540
ctggccggcg cgctgacggg ggacacggtc cgcggactgc aggagtcggt gatcgcgtgc    600
gtcaagcatt tgatcggcaa cgagcaggag accaaccgca acagcccgca gatgctgacg    660
ggctcgcaca accagtcggt ctcgtccaac atcgacgaca ggaccatgca cgagctgtac    720
ctctggccgt tccaggacgc ggtcaaggcc ggcgccggct ccgtcatgtg cagctataac    780
cgcatcaaca acagctacgg ctgccagaac agcaagacca tgaacgggct gctcaagggc    840
gagctgggct tccagggctt cgtcgtctcc gactggaccg cccagcacac ggggctggcc    900
agcgccgccg ccgggctgga catggccatg ccctcctccg agtactggga cagcaaccag    960
ctggcgacgg cggtggccaa cggctccctc gccgcgaccc gactcgacga catggccacg   1020
cgcatcgtcg ccgcctggta caagtacgcc gagctagagg accccggcca cggcctgccc   1080
gtcagcctgc tggagccaca ccccctcgtt gacgcgcgcg acccagccgc caaggagacg   1140
atcttccagg gtgccgtcga gggccacgtg ctggtcaaga acacgaacca ggcccttccc   1200
ttgacctcgc cgcgcttcct ctccctcttc ggctacgacg ccatcgccgc gccgcagaac   1260
acgatggacg acctctcgtg gagcctgtgg gcgatgggct ggacgaacac gcagacgtac   1320
cccaacggca gcgcggtgga cccgacgatg ctgaagtaca tcttcctgtc gagcgccgac   1380
cccactgcca cggggcccgg catcgccctg aacggcacga tgtacaccgg ggcgggtcc   1440
gggtcgagca cgccctcgta catcgacgct cccttcgacg ccctgcagcg ccaggcgcgc   1500
gaagacaaca ccttcctagc gtgggacttc acctccgcga ccccgctcgt caacccggcc   1560
agcgaagcat gcctcgtctt catcaacgcc gccgccgccg aaggatggga ccgcccggcc   1620
ctgagcgaca gctactcgga caacctcgtc acgcacgtgg cctcgcaatg caacaacacg   1680
atcgtggtca tccacaacgc gggcatccgg cccgtcgacg cctggatcga gcaccccaac   1740
atcaccgccg tgatgtacgc ccacctgccg ggccaggaca cgggcgccgc gctggtcgag   1800
gtgctgtacg gcaagcaatc gccgtccggc cgcctgccct acaccgtcgc gcggaacgca   1860
agcgactacg cgccctgct gtccccgacc ctgccgtccg ccgagaaaga caagacggaa   1920
atctactacc cgcaggacac cttcagcgag ggcgtgtaca tcgactacaa gcacttcgag   1980
gcgcagaaca tcacgccgcg gttcccgttc gggtacggcc tcacctacac cgatttcacg   2040
tacagcaacc tcgttgtcaa caccacgacg acggcagcga caagcctcac cccgcctgat   2100
cttaatggcg ccgtcgcgga gggcggtctc ccttccctct gggacgtgtt ggtcactgtt   2160
tcgtgcaccc tggagaatac gggcagtgtg gcggccaagg aggtcgcgca gctgtatgtg   2220
gggatccccg gtgggccggc gaaggtgctg cgcgggtttg tcaaggagct ggtggagccc   2280
ggtcagaaga aggaggtcag ctttgcgttg acgaggaggg atctgagtac ctgggatgtg   2340
gaggtgcaga gttgggtgtt gcagcagggg gagtatgggt tgtttgtggg gaagaatgtc   2400
gctgatgtgc tgttgacggg gtcggtggcg ttttag                             2436
```

<210> SEQ ID NO 10
<211> LENGTH: 811
<212> TYPE: PRT
<213> ORGANISM: Aspergillus aculeatus

<400> SEQUENCE: 10

Met Lys Leu Thr Val Pro Leu Thr Ala Ala Ala Leu Pro Leu Ala Gly

-continued

```
1               5                   10                  15
Ala Ala Val Ile Gln Pro Arg Thr Leu Asn Val Thr Asp Leu Glu His
                    20                  25                  30

Tyr Trp Ser Tyr Gly Arg Ser Glu Pro Val Tyr Pro Thr Pro Glu Thr
                35                  40                  45

Gln Gly Leu Gly Asp Trp Glu Asp Ala Phe Thr Lys Ala Lys Ala Leu
    50                  55                  60

Val Ala Gln Met Thr Asn Glu Glu Lys Asn Asn Leu Thr Tyr Gly Tyr
65                  70                  75                  80

Ser Ser Thr Thr Asn Gly Cys Ser Gly Asn Thr Ala Gly Val Pro Arg
                85                  90                  95

Leu Gly Phe Pro Gly Ile Cys Leu Gln Asp Ala Ala Ser Gly Val Arg
                100                 105                 110

Gly Thr Asp Met Val Asn Gly Tyr Ala Ser Gly Leu His Val Gly Ala
                115                 120                 125

Ser Trp Asn Arg Glu Leu Ala Tyr Gln Arg Ala Gln Tyr Met Gly Ala
        130                 135                 140

Glu Phe Lys Arg Lys Gly Val Asn Val Ala Leu Gly Pro Val Ala Gly
145                 150                 155                 160

Pro Leu Gly Arg Ile Ala Arg Gly Gly Arg Asn Trp Glu Gly Phe Ser
                165                 170                 175

Asn Asp Pro Tyr Leu Ala Gly Ala Leu Thr Gly Asp Thr Val Arg Gly
                180                 185                 190

Leu Gln Glu Ser Val Ile Ala Cys Val Lys His Leu Ile Gly Asn Glu
        195                 200                 205

Gln Glu Thr Asn Arg Asn Ser Pro Gln Met Leu Thr Gly Ser His Asn
        210                 215                 220

Gln Ser Val Ser Ser Asn Ile Asp Asp Arg Thr Met His Glu Leu Tyr
225                 230                 235                 240

Leu Trp Pro Phe Gln Asp Ala Val Lys Ala Gly Ala Gly Ser Val Met
                245                 250                 255

Cys Ser Tyr Asn Arg Ile Asn Asn Ser Tyr Gly Cys Gln Asn Ser Lys
                260                 265                 270

Thr Met Asn Gly Leu Leu Lys Gly Glu Leu Gly Phe Gln Gly Phe Val
        275                 280                 285

Val Ser Asp Trp Thr Ala Gln His Thr Gly Leu Ala Ser Ala Ala Ala
        290                 295                 300

Gly Leu Asp Met Ala Met Pro Ser Ser Glu Tyr Trp Asp Ser Asn Gln
305                 310                 315                 320

Leu Ala Thr Ala Val Ala Asn Gly Ser Leu Ala Ala Thr Arg Leu Asp
                325                 330                 335

Asp Met Ala Thr Arg Ile Val Ala Ala Trp Tyr Lys Tyr Ala Glu Leu
                340                 345                 350

Glu Asp Pro Gly His Gly Leu Pro Val Ser Leu Glu Pro His Pro
        355                 360                 365

Leu Val Asp Ala Arg Asp Pro Ala Ala Lys Glu Thr Ile Phe Gln Gly
    370                 375                 380

Ala Val Glu Gly His Val Leu Val Lys Asn Thr Asn Gln Ala Leu Pro
385                 390                 395                 400

Leu Thr Ser Pro Arg Phe Leu Ser Leu Phe Gly Tyr Asp Ala Ile Ala
                405                 410                 415

Ala Pro Gln Asn Thr Met Asp Asp Leu Ser Trp Ser Leu Trp Ala Met
                420                 425                 430
```

Gly Trp Thr Asn Thr Gln Thr Tyr Pro Asn Gly Ser Ala Val Asp Pro
                435                 440                 445

Thr Met Leu Lys Tyr Ile Phe Leu Ser Ser Ala Asp Pro Thr Ala Thr
450                 455                 460

Gly Pro Gly Ile Ala Leu Asn Gly Thr Met Tyr Thr Gly Gly Gly Ser
465                 470                 475                 480

Gly Ser Ser Thr Pro Ser Tyr Ile Asp Ala Pro Phe Asp Ala Leu Gln
                485                 490                 495

Arg Gln Ala Arg Glu Asp Asn Thr Phe Leu Ala Trp Asp Phe Thr Ser
                500                 505                 510

Ala Thr Pro Leu Val Asn Pro Ser Glu Ala Cys Leu Val Phe Ile
                515                 520                 525

Asn Ala Ala Ala Glu Gly Trp Asp Arg Pro Ala Leu Ser Asp Ser
530                 535                 540

Tyr Ser Asp Asn Leu Val Thr His Val Ala Ser Gln Cys Asn Asn Thr
545                 550                 555                 560

Ile Val Val Ile His Asn Ala Gly Ile Arg Pro Val Asp Ala Trp Ile
                565                 570                 575

Glu His Pro Asn Ile Thr Ala Val Met Tyr Ala His Leu Pro Gly Gln
                580                 585                 590

Asp Ser Gly Ala Ala Leu Val Glu Val Leu Tyr Gly Lys Gln Ser Pro
                595                 600                 605

Ser Gly Arg Leu Pro Tyr Thr Val Ala Arg Asn Ala Ser Asp Tyr Gly
                610                 615                 620

Ala Leu Leu Ser Pro Thr Leu Pro Ser Ala Glu Lys Asp Lys Thr Glu
625                 630                 635                 640

Ile Tyr Tyr Pro Gln Asp Thr Phe Ser Glu Gly Val Tyr Ile Asp Tyr
                645                 650                 655

Lys His Phe Glu Ala Gln Asn Ile Thr Pro Arg Phe Pro Phe Gly Tyr
                660                 665                 670

Gly Leu Thr Tyr Thr Asp Phe Thr Tyr Ser Asn Leu Val Val Asn Thr
                675                 680                 685

Thr Thr Thr Ala Ala Thr Ser Leu Thr Pro Pro Asp Leu Asn Gly Ala
                690                 695                 700

Val Ala Glu Gly Gly Leu Pro Ser Leu Trp Asp Val Leu Val Thr Val
705                 710                 715                 720

Ser Cys Thr Leu Glu Asn Thr Gly Ser Val Ala Ala Lys Glu Val Ala
                725                 730                 735

Gln Leu Tyr Val Gly Ile Pro Gly Pro Ala Lys Val Leu Arg Gly
                740                 745                 750

Phe Val Lys Glu Leu Val Glu Pro Gly Gln Lys Lys Glu Val Ser Phe
755                 760                 765

Ala Leu Thr Arg Arg Asp Leu Ser Thr Trp Asp Val Glu Val Gln Ser
770                 775                 780

Trp Val Leu Gln Gln Gly Glu Tyr Gly Leu Phe Val Gly Lys Asn Val
785                 790                 795                 800

Ala Asp Val Leu Leu Thr Gly Ser Val Ala Phe
                805                 810

<210> SEQ ID NO 11
<211> LENGTH: 2412
<212> TYPE: DNA
<213> ORGANISM: Aspergillus aculeatus

<400> SEQUENCE: 11

-continued

```
atggctgtgg cggctcttgc tctgctggcg cttttgcctc aagctctggc ccaacataac      60
agcagctacg tggattacaa cgtcgaggcc aacccggact tgtttccgca atgtctggac     120
acaatctcct tgtccttccc cgactgccag agcggtcctc tgagcaagaa cctcgtctgc     180
gactcgaccg cctcgcccta tgaccgcgcc gcggccctga tctccctctt caccctcgag     240
gagctcattg ccaacactgg taacaccagc cccggtgtcc ctcgtctggg tctacctcca     300
taccaggtct ggagtgaggc cttgcatggc ctggaccgcg gcaatttcac cgacgagggg     360
gcttacagct gggcgacatc cttcccctcg cccattctct ccgctgctgc cttcaatcgc     420
accctgatca accagatcgc atccattatc tcaactcagg ggcgcgcctt caataacgcc     480
ggccgctacg gtctcgatgt ctacgccccc aacatcaatg ccttccgtca tcccgtctgg     540
gggcgcggac aggaaactcc gggcgaggat gcgtatactc tcacagccgc ctacgcctac     600
gaatacatca cgggtatcca gggtggcgtg gacccagagc atctgaagct cgcagcgaca     660
gccaagcact tgccggcta tgacatcgag aactgggaca ccactcccg gctggggaac     720
gatgtcaaca tcacgcagca agacctggcc gagtactaca cgccgcagtt cctcgtggcc     780
acgcgcgatg cccgcgtcca cagcgtcatg tgctcgtaca cgccgtcaa cggcgtgccc     840
agctgctcca caccttctt cctgcagacg ctcctgcgcg cacccttctc cttcgttgac     900
cacggctacg tctccggcga ttgcggtgcc gtctacggcg ttttcaaccc ccacggctac     960
gcggccaacg agtccagcgc cgccgccgac tccatcctcg ccggcaccga catcgactgc    1020
ggcacctcct accaatacca cttcaacgag tccatcacca ccagggcggt cgcccgcgac    1080
gacatcgagc gcggcctcac ccggctatac gccaacctcg tccggctagg ctacttcgag    1140
ggcaacagca gcagcagcag cccgtaccgc agcctgagct ggtccgacgt ccagaagaca    1200
gacgcatgga acatttccta cgaagcggcc gtcgagggca tcgtcctcct gaagaacgac    1260
ggcgccctcc cgcttccctc ctcctcctcc tcgggcaaga ataaatccat cgccctcatc    1320
ggccctggg ccaacgccac cacccagctc cagggcaact actacggcgc ggcgccatac    1380
ctcatcagcc cggtcgacgc cttcacggcc gccggctaca cggtccacta cgcccccggc    1440
acggagatct ccacgaactc gacggcgaac ttcagcgccg cgctctccgc cgcgcgcgcc    1500
gccgacacca tcgtattctt cggagggatc gacaacacca tcgaggcgga agcccaagac    1560
cgcagctcga tcgcctggcc cggcaaccaa ctcgagctga tctcgcaact ggccgcgcag    1620
aaatccgagt cccagcccct ggtggtgtac cagatgggcg gcgggcaggt cgactcctcc    1680
gccctgaaag cgaatccgaa ggtcaacgcc ctcctctggg gcggctaccc gggccaatcc    1740
ggcggcctcg ccctccgcga catcctcacg ggcgcccgcg ccccggccgg ccgcctcacc    1800
acgacccagt accccgccgc ctacgccgag agcttctcgg cgctcgacat gaacctgcgg    1860
cccaacacca ccaccaacaa cccaggccaa acctacatgt ggtacaccgg cgaacccgtc    1920
tacgaattcg gccacggcct cttctacacc accttcaagg ctgcccccgc agcggcgaag    1980
aagtatacct tcaacatcac agacctcacc tcctccgcgc accggacac caccaccgtc    2040
gcccaacgca ccctcttcaa cttcacgcg accatcacga actctgggc ccgggactcc    2100
gattacaccg ccctggtgtt cgccaacacc tcgagtgcgg gcccgtcccc gtacccgaac    2160
aaatggctcg tcgggttcga taggctcgct gctgtggcca aggaggggg cacgacggtg    2220
ttgaatgtgc ccgtggcggt ggatcggttg gccagggtgg atgacaatgg gaattccgtg    2280
ctgtttccgg ggcggtatga ggtggccttg aataatgagc gcgaggtcgt ggttgaggtg    2340
gagttggtgg gggaggcggt ggtgttggtg aagtggccgg aggaggtgca gggggtgcag    2400
```
ggggatgagt ag                                                        2412

<210> SEQ ID NO 12
<211> LENGTH: 803
<212> TYPE: PRT
<213> ORGANISM: Aspergillus aculeatus

<400> SEQUENCE: 12

```
Met Ala Val Ala Ala Leu Ala Leu Leu Ala Leu Leu Pro Gln Ala Leu
1               5                   10                  15

Ala Gln His Asn Ser Ser Tyr Val Asp Tyr Asn Val Glu Ala Asn Pro
            20                  25                  30

Asp Leu Phe Pro Gln Cys Leu Asp Thr Ile Ser Leu Ser Phe Pro Asp
        35                  40                  45

Cys Gln Ser Gly Pro Leu Ser Lys Asn Leu Val Cys Asp Ser Thr Ala
    50                  55                  60

Ser Pro Tyr Asp Arg Ala Ala Leu Ile Ser Leu Phe Thr Leu Glu
65                  70                  75                  80

Glu Leu Ile Ala Asn Thr Gly Asn Thr Ser Pro Gly Val Pro Arg Leu
                85                  90                  95

Gly Leu Pro Pro Tyr Gln Val Trp Ser Glu Ala Leu His Gly Leu Asp
            100                 105                 110

Arg Gly Asn Phe Thr Asp Glu Gly Ala Tyr Ser Trp Ala Thr Ser Phe
        115                 120                 125

Pro Ser Pro Ile Leu Ser Ala Ala Ala Phe Asn Arg Thr Leu Ile Asn
    130                 135                 140

Gln Ile Ala Ser Ile Ile Ser Thr Gln Gly Arg Ala Phe Asn Asn Ala
145                 150                 155                 160

Gly Arg Tyr Gly Leu Asp Val Tyr Ala Pro Asn Ile Asn Ala Phe Arg
                165                 170                 175

His Pro Val Trp Gly Arg Gly Gln Glu Thr Pro Gly Glu Asp Ala Tyr
            180                 185                 190

Thr Leu Thr Ala Ala Tyr Ala Tyr Glu Tyr Ile Thr Gly Ile Gln Gly
        195                 200                 205

Gly Val Asp Pro Glu His Leu Lys Leu Ala Ala Thr Ala Lys His Phe
    210                 215                 220

Ala Gly Tyr Asp Ile Glu Asn Trp Asp Asn His Ser Arg Leu Gly Asn
225                 230                 235                 240

Asp Val Asn Ile Thr Gln Gln Asp Leu Ala Glu Tyr Tyr Thr Pro Gln
                245                 250                 255

Phe Leu Val Ala Thr Arg Asp Ala Arg Val His Ser Val Met Cys Ser
            260                 265                 270

Tyr Asn Ala Val Asn Gly Val Pro Ser Cys Ser Asn Thr Phe Leu
        275                 280                 285

Gln Thr Leu Leu Arg Asp Thr Phe Ser Phe Val Asp His Gly Tyr Val
    290                 295                 300

Ser Gly Asp Cys Gly Ala Val Tyr Gly Val Phe Asn Pro His Gly Tyr
305                 310                 315                 320

Ala Ala Asn Glu Ser Ser Ala Ala Ala Asp Ser Ile Leu Ala Gly Thr
                325                 330                 335

Asp Ile Asp Cys Gly Thr Ser Tyr Gln Tyr His Phe Asn Glu Ser Ile
            340                 345                 350

Thr Thr Arg Ala Val Ala Arg Asp Asp Ile Glu Arg Gly Leu Thr Arg
        355                 360                 365

Leu Tyr Ala Asn Leu Val Arg Leu Gly Tyr Phe Glu Gly Asn Ser Ser
```

-continued

```
            370                 375                 380
Ser Ser Ser Pro Tyr Arg Ser Leu Ser Trp Ser Asp Val Gln Lys Thr
385                 390                 395                 400

Asp Ala Trp Asn Ile Ser Tyr Glu Ala Ala Val Glu Gly Ile Val Leu
                405                 410                 415

Leu Lys Asn Asp Gly Ala Leu Pro Leu Pro Ser Ser Ser Ser Ser Gly
                420                 425                 430

Lys Asn Lys Ser Ile Ala Leu Ile Gly Pro Trp Ala Asn Ala Thr Thr
                435                 440                 445

Gln Leu Gln Gly Asn Tyr Tyr Gly Ala Ala Pro Tyr Leu Ile Ser Pro
                450                 455                 460

Val Asp Ala Phe Thr Ala Ala Gly Tyr Thr Val His Tyr Ala Pro Gly
465                 470                 475                 480

Thr Glu Ile Ser Thr Asn Ser Thr Ala Asn Phe Ser Ala Ala Leu Ser
                485                 490                 495

Ala Ala Arg Ala Ala Asp Thr Ile Val Phe Phe Gly Gly Ile Asp Asn
                500                 505                 510

Thr Ile Glu Ala Glu Ala Gln Asp Arg Ser Ser Ile Ala Trp Pro Gly
                515                 520                 525

Asn Gln Leu Glu Leu Ile Ser Gln Leu Ala Ala Gln Lys Ser Glu Ser
                530                 535                 540

Gln Pro Leu Val Val Tyr Gln Met Gly Gly Gln Val Asp Ser Ser
545                 550                 555                 560

Ala Leu Lys Ala Asn Pro Lys Val Asn Ala Leu Leu Trp Gly Gly Tyr
                565                 570                 575

Pro Gly Gln Ser Gly Gly Leu Ala Leu Arg Asp Ile Leu Thr Gly Ala
                580                 585                 590

Arg Ala Pro Ala Gly Arg Leu Thr Thr Thr Gln Tyr Pro Ala Ala Tyr
                595                 600                 605

Ala Glu Ser Phe Ser Ala Leu Asp Met Asn Leu Arg Pro Asn Thr Thr
                610                 615                 620

Thr Asn Asn Pro Gly Gln Thr Tyr Met Trp Tyr Thr Gly Glu Pro Val
625                 630                 635                 640

Tyr Glu Phe Gly His Gly Leu Phe Tyr Thr Thr Phe Lys Ala Ala Pro
                645                 650                 655

Ala Ala Ala Lys Lys Tyr Thr Phe Asn Ile Thr Asp Leu Thr Ser Ser
                660                 665                 670

Ala His Pro Asp Thr Thr Thr Val Ala Gln Arg Thr Leu Phe Asn Phe
                675                 680                 685

Thr Ala Thr Ile Thr Asn Ser Gly Ala Arg Asp Ser Asp Tyr Thr Ala
                690                 695                 700

Leu Val Phe Ala Asn Thr Ser Ala Gly Pro Ser Pro Tyr Pro Asn
705                 710                 715                 720

Lys Trp Leu Val Gly Phe Asp Arg Leu Ala Ala Val Ala Lys Glu Gly
                725                 730                 735

Gly Thr Thr Val Leu Asn Val Pro Val Ala Val Asp Arg Leu Ala Arg
                740                 745                 750

Val Asp Asp Asn Gly Asn Ser Val Leu Phe Pro Gly Arg Tyr Glu Val
                755                 760                 765

Ala Leu Asn Asn Glu Arg Glu Val Val Val Glu Val Glu Leu Val Gly
                770                 775                 780

Glu Ala Val Val Leu Val Lys Trp Pro Glu Glu Val Gln Gly Val Gln
785                 790                 795                 800
```

Gly Asp Glu

<210> SEQ ID NO 13
<211> LENGTH: 42
<212> TYPE: DNA
<213> ORGANISM: Aspergillus aculeatus

<400> SEQUENCE: 13
acacaactgg ggatccacca tgaccccat ctggcattac ct        42

<210> SEQ ID NO 14
<211> LENGTH: 43
<212> TYPE: DNA
<213> ORGANISM: Aspergillus aculeatus

<400> SEQUENCE: 14
ggtggatccc cagttgtgtc tagagaacct cacaagcacc ccc        43

<210> SEQ ID NO 15
<211> LENGTH: 40
<212> TYPE: DNA
<213> ORGANISM: Aspergillus aculeatus

<400> SEQUENCE: 15
acacaactgg ggatccacca tgagattcat ttcacttgcc        40

<210> SEQ ID NO 16
<211> LENGTH: 37
<212> TYPE: DNA
<213> ORGANISM: Aspergillus aculeatus

<400> SEQUENCE: 16
agatctcgag aagcttacta agccttcact ctcaaag        37

<210> SEQ ID NO 17
<211> LENGTH: 37
<212> TYPE: DNA
<213> ORGANISM: Aspergillus aculeatus

<400> SEQUENCE: 17
acacaactgg ggatccacca tgcacagctt aggatcc        37

<210> SEQ ID NO 18
<211> LENGTH: 35
<212> TYPE: DNA
<213> ORGANISM: Aspergillus aculeatus

<400> SEQUENCE: 18
agatctcgag aagcttacta cacggtcaac gtcaa        35

<210> SEQ ID NO 19
<211> LENGTH: 44
<212> TYPE: DNA
<213> ORGANISM: Aspergillus aculeatus

<400> SEQUENCE: 19
acacaactgg ggatccacca tgggtgctag tttgctaacc aagg        44

<210> SEQ ID NO 20
<211> LENGTH: 46
<212> TYPE: DNA
<213> ORGANISM: Aspergillus aculeatus

<400> SEQUENCE: 20

-continued

```
ggtggatccc cagttgtgtc tactcaacat agaacgtcgc attccc          46
```

<210> SEQ ID NO 21
<211> LENGTH: 45
<212> TYPE: DNA
<213> ORGANISM: Aspergillus aculeatus

<400> SEQUENCE: 21

```
acacaactgg ggatccacca tgaagcttac cgttcccta acggc            45
```

<210> SEQ ID NO 22
<211> LENGTH: 39
<212> TYPE: DNA
<213> ORGANISM: Aspergillus aculeatus

<400> SEQUENCE: 22

```
ggtggatccc cagttgtgtc taaaacgcca ccgaccccg                  39
```

<210> SEQ ID NO 23
<211> LENGTH: 37
<212> TYPE: DNA
<213> ORGANISM: Aspergillus aculeatus

<400> SEQUENCE: 23

```
acacaactgg ggatccacca tggctgtggc ggctctt                    37
```

<210> SEQ ID NO 24
<211> LENGTH: 35
<212> TYPE: DNA
<213> ORGANISM: Aspergillus aculeatus

<400> SEQUENCE: 24

```
agatctcgag aagcttacta ctcatccccc tgcac                      35
```

<210> SEQ ID NO 25
<211> LENGTH: 19
<212> TYPE: PRT
<213> ORGANISM: Thielavia terrestris
<220> FEATURE:
<221> NAME/KEY: MISC_FEATURE
<222> LOCATION: (1)..(1)
<223> OTHER INFORMATION: X=I,L,M, OR V
<220> FEATURE:
<221> NAME/KEY: misc_feature
<222> LOCATION: (3)..(6)
<223> OTHER INFORMATION: Xaa can be any naturally occurring amino acid
<220> FEATURE:
<221> NAME/KEY: misc_feature
<222> LOCATION: (8)..(8)
<223> OTHER INFORMATION: Xaa can be any naturally occurring amino acid
<220> FEATURE:
<221> NAME/KEY: MISC_FEATURE
<222> LOCATION: (10)..(10)
<223> OTHER INFORMATION: X=I,L,M, OR V
<220> FEATURE:
<221> NAME/KEY: misc_feature
<222> LOCATION: (11)..(11)
<223> OTHER INFORMATION: Xaa can be any naturally occurring amino acid
<220> FEATURE:
<221> NAME/KEY: misc_feature
<222> LOCATION: (13)..(13)
<223> OTHER INFORMATION: Xaa can be any naturally occurring amino acid
<220> FEATURE:
<221> NAME/KEY: MISC_FEATURE
<222> LOCATION: (14)..(14)
<223> OTHER INFORMATION: X=E OR Q
<220> FEATURE:
<221> NAME/KEY: misc_feature
<222> LOCATION: (15)..(18)
<223> OTHER INFORMATION: Xaa can be any naturally occurring amino acid
<220> FEATURE:

```
<221> NAME/KEY: MISC_FEATURE
<222> LOCATION: (19)..(19)
<223> OTHER INFORMATION: X=H,N, OR Q

<400> SEQUENCE: 25

Xaa Pro Xaa Xaa Xaa Xaa Gly Xaa Tyr Xaa Xaa Arg Xaa Xaa Xaa Xaa
1               5                   10                  15

Xaa Xaa Xaa

<210> SEQ ID NO 26
<211> LENGTH: 20
<212> TYPE: PRT
<213> ORGANISM: Thielavia terrestris
<220> FEATURE:
<221> NAME/KEY: MISC_FEATURE
<222> LOCATION: (1)..(1)
<223> OTHER INFORMATION: X=I,L,M, OR V
<220> FEATURE:
<221> NAME/KEY: misc_feature
<222> LOCATION: (3)..(7)
<223> OTHER INFORMATION: Xaa can be any naturally occurring amino acid
<220> FEATURE:
<221> NAME/KEY: misc_feature
<222> LOCATION: (9)..(9)
<223> OTHER INFORMATION: Xaa can be any naturally occurring amino acid
<220> FEATURE:
<221> NAME/KEY: MISC_FEATURE
<222> LOCATION: (11)..(11)
<223> OTHER INFORMATION: X=I,L,M, OR V
<220> FEATURE:
<221> NAME/KEY: misc_feature
<222> LOCATION: (12)..(12)
<223> OTHER INFORMATION: Xaa can be any naturally occurring amino acid
<220> FEATURE:
<221> NAME/KEY: misc_feature
<222> LOCATION: (14)..(14)
<223> OTHER INFORMATION: Xaa can be any naturally occurring amino acid
<220> FEATURE:
<221> NAME/KEY: MISC_FEATURE
<222> LOCATION: (15)..(15)
<223> OTHER INFORMATION: X=E OR Q
<220> FEATURE:
<221> NAME/KEY: misc_feature
<222> LOCATION: (16)..(19)
<223> OTHER INFORMATION: Xaa can be any naturally occurring amino acid
<220> FEATURE:
<221> NAME/KEY: MISC_FEATURE
<222> LOCATION: (20)..(20)
<223> OTHER INFORMATION: X=H,N, OR Q

<400> SEQUENCE: 26

Xaa Pro Xaa Xaa Xaa Xaa Xaa Gly Xaa Tyr Xaa Xaa Arg Xaa Xaa Xaa
1               5                   10                  15

Xaa Xaa Xaa Xaa
            20

<210> SEQ ID NO 27
<211> LENGTH: 9
<212> TYPE: PRT
<213> ORGANISM: Thielavia terrestris
<220> FEATURE:
<221> NAME/KEY: misc_feature
<222> LOCATION: (2)..(2)
<223> OTHER INFORMATION: Xaa can be any naturally occurring amino acid
<220> FEATURE:
<221> NAME/KEY: misc_feature
<222> LOCATION: (5)..(7)
<223> OTHER INFORMATION: Xaa can be any naturally occurring amino acid
<220> FEATURE:
<221> NAME/KEY: MISC_FEATURE
<222> LOCATION: (8)..(8)
<223> OTHER INFORMATION: X= Y OR W
<220> FEATURE:
<221> NAME/KEY: MISC_FEATURE
```

```
<222> LOCATION: (9)..(9)
<223> OTHER INFORMATION: X= A,I,L,M OR V

<400> SEQUENCE: 27

His Xaa Gly Pro Xaa Xaa Xaa Xaa Xaa
1               5

<210> SEQ ID NO 28
<211> LENGTH: 10
<212> TYPE: PRT
<213> ORGANISM: Thielavia terrestris
<220> FEATURE:
<221> NAME/KEY: misc_feature
<222> LOCATION: (2)..(3)
<223> OTHER INFORMATION: Xaa can be any naturally occurring amino acid
<220> FEATURE:
<221> NAME/KEY: misc_feature
<222> LOCATION: (6)..(8)
<223> OTHER INFORMATION: Xaa can be any naturally occurring amino acid
<220> FEATURE:
<221> NAME/KEY: MISC_FEATURE
<222> LOCATION: (9)..(9)
<223> OTHER INFORMATION: X= Y OR W
<220> FEATURE:
<221> NAME/KEY: MISC_FEATURE
<222> LOCATION: (10)..(10)
<223> OTHER INFORMATION: X= A,I,L,M OR V

<400> SEQUENCE: 28

His Xaa Xaa Gly Pro Xaa Xaa Xaa Xaa Xaa
1               5                   10

<210> SEQ ID NO 29
<211> LENGTH: 11
<212> TYPE: PRT
<213> ORGANISM: Thielavia terrestris
<220> FEATURE:
<221> NAME/KEY: MISC_FEATURE
<222> LOCATION: (1)..(1)
<223> OTHER INFORMATION: X= E OR Q
<220> FEATURE:
<221> NAME/KEY: misc_feature
<222> LOCATION: (2)..(2)
<223> OTHER INFORMATION: Xaa can be any naturally occurring amino acid
<220> FEATURE:
<221> NAME/KEY: misc_feature
<222> LOCATION: (4)..(5)
<223> OTHER INFORMATION: Xaa can be any naturally occurring amino acid
<220> FEATURE:
<221> NAME/KEY: misc_feature
<222> LOCATION: (7)..(7)
<223> OTHER INFORMATION: Xaa can be any naturally occurring amino acid
<220> FEATURE:
<221> NAME/KEY: MISC_FEATURE
<222> LOCATION: (8)..(8)
<223> OTHER INFORMATION: X= E,H,Q OR N
<220> FEATURE:
<221> NAME/KEY: MISC_FEATURE
<222> LOCATION: (9)..(9)
<223> OTHER INFORMATION: X=F,I,L, OR V
<220> FEATURE:
<221> NAME/KEY: misc_feature
<222> LOCATION: (10)..(10)
<223> OTHER INFORMATION: Xaa can be any naturally occurring amino acid
<220> FEATURE:
<221> NAME/KEY: MISC_FEATURE
<222> LOCATION: (11)..(11)
<223> OTHER INFORMATION: X=I,L,OR V

<400> SEQUENCE: 29

Xaa Xaa Tyr Xaa Xaa Cys Xaa Xaa Xaa Xaa
1               5                   10

<210> SEQ ID NO 30
```

```
<211> LENGTH: 9
<212> TYPE: PRT
<213> ORGANISM: Thielavia terrestris
<220> FEATURE:
<221> NAME/KEY: misc_feature
<222> LOCATION: (2)..(2)
<223> OTHER INFORMATION: Xaa can be any naturally occurring amino acid
<220> FEATURE:
<221> NAME/KEY: misc_feature
<222> LOCATION: (5)..(7)
<223> OTHER INFORMATION: Xaa can be any naturally occurring amino acid
<220> FEATURE:
<221> NAME/KEY: MISC_FEATURE
<222> LOCATION: (8)..(8)
<223> OTHER INFORMATION: X= Y OR W
<220> FEATURE:
<221> NAME/KEY: MISC_FEATURE
<222> LOCATION: (9)..(9)
<223> OTHER INFORMATION: X= A,I,L,M OR V

<400> SEQUENCE: 30

His Xaa Gly Pro Xaa Xaa Xaa Xaa Xaa
1               5

<210> SEQ ID NO 31
<211> LENGTH: 10
<212> TYPE: PRT
<213> ORGANISM: Thielavia terrestris
<220> FEATURE:
<221> NAME/KEY: misc_feature
<222> LOCATION: (2)..(3)
<223> OTHER INFORMATION: Xaa can be any naturally occurring amino acid
<220> FEATURE:
<221> NAME/KEY: misc_feature
<222> LOCATION: (6)..(8)
<223> OTHER INFORMATION: Xaa can be any naturally occurring amino acid
<220> FEATURE:
<221> NAME/KEY: MISC_FEATURE
<222> LOCATION: (9)..(9)
<223> OTHER INFORMATION: X= Y OR W
<220> FEATURE:
<221> NAME/KEY: MISC_FEATURE
<222> LOCATION: (10)..(10)
<223> OTHER INFORMATION: X= A,I,L,M OR V

<400> SEQUENCE: 31

His Xaa Xaa Gly Pro Xaa Xaa Xaa Xaa Xaa
1               5                   10

<210> SEQ ID NO 32
<211> LENGTH: 11
<212> TYPE: PRT
<213> ORGANISM: Thielavia terrestris
<220> FEATURE:
<221> NAME/KEY: MISC_FEATURE
<222> LOCATION: (1)..(1)
<223> OTHER INFORMATION: X= E OR Q
<220> FEATURE:
<221> NAME/KEY: misc_feature
<222> LOCATION: (2)..(2)
<223> OTHER INFORMATION: Xaa can be any naturally occurring amino acid
<220> FEATURE:
<221> NAME/KEY: misc_feature
<222> LOCATION: (4)..(5)
<223> OTHER INFORMATION: Xaa can be any naturally occurring amino acid
<220> FEATURE:
<221> NAME/KEY: misc_feature
<222> LOCATION: (7)..(7)
<223> OTHER INFORMATION: Xaa can be any naturally occurring amino acid
<220> FEATURE:
<221> NAME/KEY: MISC_FEATURE
<222> LOCATION: (8)..(8)
<223> OTHER INFORMATION: X= E,H,Q OR N
<220> FEATURE:
<221> NAME/KEY: MISC_FEATURE
<222> LOCATION: (9)..(9)
```

<223> OTHER INFORMATION: X=F,I,L, OR V
<220> FEATURE:
<221> NAME/KEY: misc_feature
<222> LOCATION: (10)..(10)
<223> OTHER INFORMATION: Xaa can be any naturally occurring amino acid
<220> FEATURE:
<221> NAME/KEY: MISC_FEATURE
<222> LOCATION: (11)..(11)
<223> OTHER INFORMATION: X=I,L,OR V

<400> SEQUENCE: 32

Xaa Xaa Tyr Xaa Xaa Cys Xaa Xaa Xaa Xaa Xaa
1               5                   10

<210> SEQ ID NO 33
<211> LENGTH: 9
<212> TYPE: PRT
<213> ORGANISM: Thielavia terrestris
<220> FEATURE:
<221> NAME/KEY: misc_feature
<222> LOCATION: (2)..(2)
<223> OTHER INFORMATION: Xaa can be any naturally occurring amino acid
<220> FEATURE:
<221> NAME/KEY: misc_feature
<222> LOCATION: (5)..(7)
<223> OTHER INFORMATION: Xaa can be any naturally occurring amino acid
<220> FEATURE:
<221> NAME/KEY: MISC_FEATURE
<222> LOCATION: (8)..(8)
<223> OTHER INFORMATION: X= Y OR W
<220> FEATURE:
<221> NAME/KEY: MISC_FEATURE
<222> LOCATION: (9)..(9)
<223> OTHER INFORMATION: X= A,I,L,M OR V

<400> SEQUENCE: 33

His Xaa Gly Pro Xaa Xaa Xaa Xaa Xaa
1               5

<210> SEQ ID NO 34
<211> LENGTH: 10
<212> TYPE: PRT
<213> ORGANISM: Thielavia terrestris
<220> FEATURE:
<221> NAME/KEY: misc_feature
<222> LOCATION: (2)..(3)
<223> OTHER INFORMATION: Xaa can be any naturally occurring amino acid
<220> FEATURE:
<221> NAME/KEY: misc_feature
<222> LOCATION: (6)..(8)
<223> OTHER INFORMATION: Xaa can be any naturally occurring amino acid
<220> FEATURE:
<221> NAME/KEY: MISC_FEATURE
<222> LOCATION: (9)..(9)
<223> OTHER INFORMATION: X= Y OR W
<220> FEATURE:
<221> NAME/KEY: MISC_FEATURE
<222> LOCATION: (10)..(10)
<223> OTHER INFORMATION: X= A,I,L,M OR V

<400> SEQUENCE: 34

His Xaa Xaa Gly Pro Xaa Xaa Xaa Xaa Xaa
1               5                   10

<210> SEQ ID NO 35
<211> LENGTH: 11
<212> TYPE: PRT
<213> ORGANISM: Thielavia terrestris
<220> FEATURE:
<221> NAME/KEY: MISC_FEATURE
<222> LOCATION: (1)..(1)
<223> OTHER INFORMATION: X= E OR Q
<220> FEATURE:
<221> NAME/KEY: misc_feature -continued

```
<222> LOCATION: (2)..(2)
<223> OTHER INFORMATION: Xaa can be any naturally occurring amino acid
<220> FEATURE:
<221> NAME/KEY: misc_feature
<222> LOCATION: (4)..(5)
<223> OTHER INFORMATION: Xaa can be any naturally occurring amino acid
<220> FEATURE:
<221> NAME/KEY: misc_feature
<222> LOCATION: (7)..(7)
<223> OTHER INFORMATION: Xaa can be any naturally occurring amino acid
<220> FEATURE:
<221> NAME/KEY: MISC_FEATURE
<222> LOCATION: (8)..(8)
<223> OTHER INFORMATION: X= E,H,Q OR N
<220> FEATURE:
<221> NAME/KEY: MISC_FEATURE
<222> LOCATION: (9)..(9)
<223> OTHER INFORMATION: X=F,I,L, OR V
<220> FEATURE:
<221> NAME/KEY: misc_feature
<222> LOCATION: (10)..(10)
<223> OTHER INFORMATION: Xaa can be any naturally occurring amino acid
<220> FEATURE:
<221> NAME/KEY: MISC_FEATURE
<222> LOCATION: (11)..(11)
<223> OTHER INFORMATION: X=I,L,OR V

<400> SEQUENCE: 35

Xaa Xaa Tyr Xaa Xaa Cys Xaa Xaa Xaa Xaa Xaa
 1               5                  10

<210> SEQ ID NO 36
<211> LENGTH: 9
<212> TYPE: PRT
<213> ORGANISM: Thielavia terrestris
<220> FEATURE:
<221> NAME/KEY: misc_feature
<222> LOCATION: (2)..(2)
<223> OTHER INFORMATION: Xaa can be any naturally occurring amino acid
<220> FEATURE:
<221> NAME/KEY: misc_feature
<222> LOCATION: (5)..(7)
<223> OTHER INFORMATION: Xaa can be any naturally occurring amino acid
<220> FEATURE:
<221> NAME/KEY: MISC_FEATURE
<222> LOCATION: (8)..(8)
<223> OTHER INFORMATION: X= Y OR W
<220> FEATURE:
<221> NAME/KEY: MISC_FEATURE
<222> LOCATION: (9)..(9)
<223> OTHER INFORMATION: X= A,I,L,M OR

<400> SEQUENCE: 36

His Xaa Gly Pro Xaa Xaa Xaa Xaa Xaa
 1               5

<210> SEQ ID NO 37
<211> LENGTH: 10
<212> TYPE: PRT
<213> ORGANISM: Thielavia terrestris
<220> FEATURE:
<221> NAME/KEY: misc_feature
<222> LOCATION: (2)..(3)
<223> OTHER INFORMATION: Xaa can be any naturally occurring amino acid
<220> FEATURE:
<221> NAME/KEY: misc_feature
<222> LOCATION: (6)..(8)
<223> OTHER INFORMATION: Xaa can be any naturally occurring amino acid
<220> FEATURE:
<221> NAME/KEY: MISC_FEATURE
<222> LOCATION: (9)..(9)
<223> OTHER INFORMATION: X= Y OR W
<220> FEATURE:
<221> NAME/KEY: MISC_FEATURE
<222> LOCATION: (10)..(10)
<223> OTHER INFORMATION: X= A,I,L,M OR V
```

```
<400> SEQUENCE: 37

His Xaa Xaa Gly Pro Xaa Xaa Xaa Xaa Xaa
1               5                   10

<210> SEQ ID NO 38
<211> LENGTH: 11
<212> TYPE: PRT
<213> ORGANISM: Thielavia terrestris
<220> FEATURE:
<221> NAME/KEY: MISC_FEATURE
<222> LOCATION: (1)..(1)
<223> OTHER INFORMATION: X= E OR Q
<220> FEATURE:
<221> NAME/KEY: misc_feature
<222> LOCATION: (2)..(2)
<223> OTHER INFORMATION: Xaa can be any naturally occurring amino acid
<220> FEATURE:
<221> NAME/KEY: misc_feature
<222> LOCATION: (4)..(5)
<223> OTHER INFORMATION: Xaa can be any naturally occurring amino acid
<220> FEATURE:
<221> NAME/KEY: misc_feature
<222> LOCATION: (7)..(7)
<223> OTHER INFORMATION: Xaa can be any naturally occurring amino acid
<220> FEATURE:
<221> NAME/KEY: MISC_FEATURE
<222> LOCATION: (8)..(8)
<223> OTHER INFORMATION: X= E,H,Q OR N
<220> FEATURE:
<221> NAME/KEY: MISC_FEATURE
<222> LOCATION: (9)..(9)
<223> OTHER INFORMATION: X=F,I,L, OR V
<220> FEATURE:
<221> NAME/KEY: misc_feature
<222> LOCATION: (10)..(10)
<223> OTHER INFORMATION: Xaa can be any naturally occurring amino acid
<220> FEATURE:
<221> NAME/KEY: MISC_FEATURE
<222> LOCATION: (11)..(11)
<223> OTHER INFORMATION: X=I,L,OR V

<400> SEQUENCE: 38

Xaa Xaa Tyr Xaa Xaa Cys Xaa Xaa Xaa Xaa
1               5                   10

<210> SEQ ID NO 39
<211> LENGTH: 19
<212> TYPE: PRT
<213> ORGANISM: Thielavia terrestris
<220> FEATURE:
<221> NAME/KEY: MISC_FEATURE
<222> LOCATION: (1)..(1)
<223> OTHER INFORMATION: X=I,L,M OR V
<220> FEATURE:
<221> NAME/KEY: misc_feature
<222> LOCATION: (3)..(6)
<223> OTHER INFORMATION: Xaa can be any naturally occurring amino acid
<220> FEATURE:
<221> NAME/KEY: misc_feature
<222> LOCATION: (8)..(8)
<223> OTHER INFORMATION: Xaa can be any naturally occurring amino acid
<220> FEATURE:
<221> NAME/KEY: MISC_FEATURE
<222> LOCATION: (10)..(10)
<223> OTHER INFORMATION: X=I,L,M OR V
<220> FEATURE:
<221> NAME/KEY: misc_feature
<222> LOCATION: (11)..(11)
<223> OTHER INFORMATION: Xaa can be any naturally occurring amino acid
<220> FEATURE:
<221> NAME/KEY: misc_feature
<222> LOCATION: (13)..(13)
<223> OTHER INFORMATION: Xaa can be any naturally occurring amino acid
<220> FEATURE:
<221> NAME/KEY: MISC_FEATURE
```

```
<222> LOCATION: (14)..(14)
<223> OTHER INFORMATION: X= E OR Q
<220> FEATURE:
<221> NAME/KEY: misc_feature
<222> LOCATION: (15)..(17)
<223> OTHER INFORMATION: Xaa can be any naturally occurring amino acid
<220> FEATURE:
<221> NAME/KEY: MISC_FEATURE
<222> LOCATION: (19)..(19)
<223> OTHER INFORMATION: X= H,N, OR Q

<400> SEQUENCE: 39

Xaa Pro Xaa Xaa Xaa Xaa Gly Xaa Tyr Xaa Xaa Arg Xaa Xaa Xaa Xaa
1               5                   10                  15

Xaa Ala Xaa

<210> SEQ ID NO 40
<211> LENGTH: 20
<212> TYPE: PRT
<213> ORGANISM: Thielavia terrestris
<220> FEATURE:
<221> NAME/KEY: MISC_FEATURE
<222> LOCATION: (1)..(1)
<223> OTHER INFORMATION: X=I,L,M OR V
<220> FEATURE:
<221> NAME/KEY: misc_feature
<222> LOCATION: (3)..(7)
<223> OTHER INFORMATION: Xaa can be any naturally occurring amino acid
<220> FEATURE:
<221> NAME/KEY: misc_feature
<222> LOCATION: (9)..(9)
<223> OTHER INFORMATION: Xaa can be any naturally occurring amino acid
<220> FEATURE:
<221> NAME/KEY: MISC_FEATURE
<222> LOCATION: (11)..(11)
<223> OTHER INFORMATION: X=I,L,M OR V
<220> FEATURE:
<221> NAME/KEY: misc_feature
<222> LOCATION: (12)..(12)
<223> OTHER INFORMATION: Xaa can be any naturally occurring amino acid
<220> FEATURE:
<221> NAME/KEY: misc_feature
<222> LOCATION: (14)..(14)
<223> OTHER INFORMATION: Xaa can be any naturally occurring amino acid
<220> FEATURE:
<221> NAME/KEY: MISC_FEATURE
<222> LOCATION: (15)..(15)
<223> OTHER INFORMATION: X=E OR Q
<220> FEATURE:
<221> NAME/KEY: misc_feature
<222> LOCATION: (16)..(18)
<223> OTHER INFORMATION: Xaa can be any naturally occurring amino acid
<220> FEATURE:
<221> NAME/KEY: MISC_FEATURE
<222> LOCATION: (20)..(20)
<223> OTHER INFORMATION: X= H,N, OR Q

<400> SEQUENCE: 40

Xaa Pro Xaa Xaa Xaa Xaa Xaa Gly Xaa Tyr Xaa Xaa Arg Xaa Xaa Xaa
1               5                   10                  15

Xaa Xaa Ala Xaa
            20
```